(12) United States Patent
Paugh et al.

(10) Patent No.: US 11,946,053 B2
(45) Date of Patent: *Apr. 2, 2024

(54) METHODS FOR OVERCOMING GLUCOCORTICOID RESISTANCE AND FOR DETERMINING GLUCOCORTICOID RESISTANCE POTENTIAL IN CANCER

(71) Applicant: St. Jude Children's Research Hospital, Inc., Memphis, TN (US)

(72) Inventors: Steven W. Paugh, Memphis, TN (US); William E. Evans, Memphis, TN (US); Erik Bonten, Arlington, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 1042 days.

This patent is subject to a terminal disclaimer.

(21) Appl. No.: 16/590,588

(22) Filed: Oct. 2, 2019

(65) Prior Publication Data
US 2020/0102565 A1    Apr. 2, 2020

Related U.S. Application Data

(63) Continuation of application No. 15/022,464, filed as application No. PCT/US2014/055824 on Sep. 16, 2014, now Pat. No. 10,457,946.

(60) Provisional application No. 61/878,373, filed on Sep. 16, 2013.

(51) Int. Cl.
| | |
|---|---|
| A61K 48/00 | (2006.01) |
| A61K 31/197 | (2006.01) |
| A61K 31/198 | (2006.01) |
| A61K 31/401 | (2006.01) |
| A61K 31/4025 | (2006.01) |
| A61K 31/551 | (2006.01) |
| A61K 31/573 | (2006.01) |
| A61K 31/713 | (2006.01) |
| A61K 38/06 | (2006.01) |
| A61K 38/07 | (2006.01) |
| A61K 38/57 | (2006.01) |
| A61K 45/06 | (2006.01) |
| A61P 5/44 | (2006.01) |
| C12N 15/113 | (2010.01) |
| C12Q 1/6886 | (2018.01) |

(52) U.S. Cl.
CPC ........ *C12N 15/1137* (2013.01); *A61K 31/197* (2013.01); *A61K 31/198* (2013.01); *A61K 31/401* (2013.01); *A61K 31/4025* (2013.01); *A61K 31/551* (2013.01); *A61K 31/573* (2013.01); *A61K 31/713* (2013.01); *A61K 38/06* (2013.01); *A61K 38/07* (2013.01); *A61K 38/57* (2013.01); *A61K 45/06* (2013.01); *A61P 5/44* (2018.01); *C12Q 1/6886* (2013.01); *C12N 2310/14* (2013.01); *C12N 2310/531* (2013.01); *C12N 2320/31* (2013.01); *C12Q 2600/106* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,054,487 A | 4/2000 | Sekut et al. | |
| 2010/0178272 A1* | 7/2010 | Hartmann | A61P 37/02 424/85.4 |

OTHER PUBLICATIONS

Yang, X. et al., "A public genome-scale lentiviral expression library of human ORFs" Nature methods (2011) vol. 8, pp. 659-661.
Yeoh, E-J et al., "Classification, subtype discovery, and prediction of outcome in pediatric acute lymphoblastic leukemia by gene expression profiling" Cancer Cell (2002) vol. 1, pp. 133-143.
Yudt, M.R., and Cidlowski, J.A. "The glucocorticoid receptor: coding a diversity of proteins and responses through a single gene" Mol Endocrinol (2002) vol. 16, pp. 1719-1726.
Zhou, R. et al., "Thioredoxin-interacting protein links oxidative stress to inflammasome activation" Nature Immunology (2010) vol. 11, pp. 136-140.
Anderson, JP et al., "Initial Description of the Human NLRP3 Promoter" Genes and Immunity (2008) vol. 9, pp. 721-726.
Black, R.A. et al., "Activation of inlerleukin-1β by a co-induced protease" FEBS Lett (1989) vol. 247, No. 2, pp. 386-390.
Boehm, J.S. et al., "Integrative genomic approaches identify IKBKE as a breast cancer oncogene" Cell (2007) vol. 129, pp. 1065-1079.
Boxer, M.B. et al., "A small molecule inhibitor of Caspase 1" Probe Reports from the NIH Molecular Libraries Program (2010), 19 pages total.
Carie, AE et al., "A Chemical Biology Approach Identified a Beta-2 Adrenergic Receptor Agonist that Causes Human Tumor Regression by Blocking the Raf-1/Mek-1/Erk1/2 Pathway" Oncogene (2007) vol. 26, pp. 3777-3788.
Casano, F.J. et al., "The structure and complete nucleotide sequence of the murine gene encoding interleukin-1β converting Enzyme (ICE)" Genomics (1994) vol. 20, pp. 474-481.

(Continued)

*Primary Examiner* — Michael D Pak
(74) *Attorney, Agent, or Firm* — Troutman Pepper Hamilton Sanders, LLP

(57) ABSTRACT

The invention provides methods for overcoming glucocorticoid resistance of cancers by inhibition of CASP1. Also disclosed are diagnostic methods for determining glucocorticoid resistance potential by measuring expression level or promoter methylation status of CASP1 gene and/or NLRP3 gene.

22 Claims, 20 Drawing Sheets
Specification includes a Sequence Listing.

(56) References Cited

OTHER PUBLICATIONS

Charmandari, E. et al. "A novel point mutation in the amino terminal domain of the human glucocorticoid receptor (hGR) gene enhancing hGR-mediated gene expression" The Journal of Clinical Endocrinology and Metabolism (2008) vol. 93, pp. 1963-4968.
Cheok, M.H. et al., "Treatment-specific changes in gene expression discriminate in vivo drug response in human leukemia cells" Nat Genet (2003) vol. 34, pp. 85-90.
Den Boer, M.L. et al., "Patient stratification based on prednisolone-vincristine-asparaginase resistance profiles in children with acute lymphoblastic leukemia" J Clin Oncol (2003) vol. 21, pp. 3262-3268.
Dordelmann, M. et al., "Prednisone response is the strongest predictor of treatment outcome in infant acute lymphoblastic leukemia" Blood (1999) vol. 94, pp. 1209-1217.
Dunham et al. "An integrated encyclopedia of DNA elements in the human genome" Nature (2012) vol. 489, pp. 57-74.
Garcia-Calvo, M. et al., "Inhibition of human caspases by peptide-based and macromolecular inhibitors" The Journal of biological chemistry (1998) vol. 273, pp. 32608-32613.
Gautier, R.C. et al., "Bioconductor: open software development for computational biology and bioinformatics" Genome Biol (2004) vol. 5, R80, 16 pages total.
Herr, I. et al., "Glucocorticoid cotreatment induces apoptosis resistance toward cancer therapy in carcinomas" Cancer Research (2003) vol. 63, No. 12, pp. 3112-3120.
Holleman, A. et al., "Gene-expression patterns in drug-resistant acute lymphoblastic leukemia cells and response to treatment" The New England journal of medicine (2004) vol. 351, pp. 533-542.
Hubbell, E. et al., "Robust estimators for expression analysis" Bioinformatics (2002) vol. 18, pp. 1585-1592.
Communication (International Preliminary Report on Patentability) issued in PCT/US2014/055824 by the International Searching Authority dated Mar. 22, 2016, 11 pages total.
Jeru, I. et al., "Functional Consequences of a Germline Mutation in the Leucine-Rich Repeat Domain of NLRP3 Identified in an Atypical Autoinflammatory Disorder" Arthritis & Rheumatism (2010) vol. 62, No. 4, pp. 1176-1185.
Julien, O. et al., "Review: Caspases and their substrates" Cell Death and Differentiation (2017) vol. 24, pp. 1380-1389.
Kaspers, G.J.L. et al., "In vitro cellular drug resistance and prognosis in newly diagnosed childhood acute lymphoblastic leukemia" Blood (1997) vol. 90, pp. 2723-2729.
Kirkpatrick, B., "DNA Methylation and and Glucocorticoid Resistance Offers Clues to Improve Cancer Drugs" What is Epigenetics, News and Reviews (2015) 8 pages total.
Komiyama, T. et al., "Inhibition of interleukin-1β converting enzyme by the cowpox virus serpin CrmA: An example of cross-class inhibition" The Journal of biological chemistry (1994) vol. 269, pp. 19331-19337.
Kostura, M. J. et al., "Identification of a monocyte specific pre-interleukin 1β convertase activity" Proc. Natl. Acad. Sci. U.S.A. (1989) vol. 86, pp. 5227-5231.
Lewis, A.M. et al., "Interleukin-1 and cancer progression: the emerging role of inlerleukin-1 receptor antagonist as a novel therapeutic agent in cancer treatment" Journal of Translational Medicine (2006) vol. 4, No. 48, pp. 1-12.
Lin, XY et al., "Expression Analysis of the Human Caspase-1 Subfamily Receals Specific Regulation of the CASP5 Gene by Lipopolysaccharide and Interferon-γ" J. Biol. Chem. (2000) vol. 275, No. 51, pp. 39920-39926.
Mariathasan, S. et al., "Cryopyrin activates the inflammasome in response to toxins and ATP" Nature (2006) vol. 440, pp. 228-232.
Martinon, F. et al., "Gout-associated uric acid crystals activate the NALP3 inflammasome" Nature (2006) vol. 40, pp. 237-241.
McKay, L.I. et al., "Cross-talk between nuclear factor-kappa B and the steroid hormone receptors: mechanisms of mutual antagonism" Mol Endocrinol (1998) vol. 12, pp. 45-56.
Meijsing, S.H. et al., "DNA binding site sequence directs glucocorticoid receptor structure and activity" Science (2009) vol. 324, pp. 407-410.
Moreno, MB et al., "Apoptosis Signaling Pathways in Normal T Cells: Differential Activity of Bcl-2 and IL-1beta-converting Enzyme Family Protease Inhibitors on Glucocorticoid- and Fas-Mediated Cytotoxicity" J Immunol (1996) vol. 157, pp. 3845-3849.
Muzio, M. et al., "FLICE induced apoptosis in a cell-free system. Cleavage of caspase zymogens" The Journal of biological chemistry (1997) vol. 272, pp. 2952-2956.
Ogura, Y. et al., "The inflammasome: first line of the immune response to cell stress" Cell (2006) vol. 126, pp. 659-662.
Panchanathan, R. et al., "Aim2 Deficiency Stimulates the Expression of IFN-Inducible Ifi202, a Lupus Susceptibility Murine Gene within the Nba2 Autoimmune Susceptibility Locus" J. Immunol. (2010) vol. 185, pp. 7385-7393.
Paugh, S.W. et al., "NALP3 Inflammasome Up-Regulation and CASP1 Cleavage of the Glucocorticoid Receptor Causes Glucocorticoid Resistance in Leukemia Cells" Nat. Genet. (2015) vol. 47, No. 6, pp. 607-614.
Communication (PCT International Search Report and Written Opinion) dated Mar. 20, 2015 issued in corresponding PCT Application No. PCT/US14/55824 by the International Searching Authority 16 pages total.
Pui, C-H et al., "The relationship of blast cell glucocorticoid receptor levels to response to single-agent steroid trial and remission response in children with acute lymphoblastic leukemia" Leukemia research (1984) vol. 8, pp. 579-585.
Pui, C-H et al., "Treating childhood acute lymphoblastic leukemia without cranial irradiation" The New England journal of medicine (2009) vol. 360, pp. 2730-2741.
Ray, C.A. et al., "Viral inhibition of inflammation: cowpox virus encodes an inhibitor of the interleukin-1 beta converting Enzyme" Cell (1992) vol. 69, pp. 597-604.
Reddy, T.E. et al., "Genomic determination of the glucocorticoid response reveals unexpected mechanisms of gene regulation" Genome research (2009) vol. 19, pp. 2163-2171.
Pieters, R. et al., "Relation of cellular drug resistance to long-term clinical outcome in childhood acute lymphoblastic leukaemia" Lancet (1991) vol. 338, pp. 399-403.
Schlossmacher, G. et al., "Glucocorticoid Receptor-Mediated Apoptosis: Mechanisms of Resistance in Cancer Cells" J Endocrinol (2011) vol. 211, pp. 17-25.
Schroder, K., and Tschopp, J., "The inflammasomes" Cell (2010) vol. 140, pp. 821-832.
Sepulveda, A.R. et al., "CpG Methylation Analysis—Current Status of Clinical Assays and Potential Applications in Molecular Diagnostics" J. Mol. Diag. (2009) vol. 11, No. 4, pp. 266-278.
Stack, J.H. et al., "IL-Converting Enzyme.Caspase-1 Inhibitor VX-765 Blocks the Hypersensitive Response to an Inflammatory Stimulus in Monocytes from Familial Cold Autoinflammatory Syndrome Patients" J Immunol. (2005) vol. 175, pp. 2630-2634.
Teurich, S., and Angel, P., "The glucocorticoid receptor synergizes with Jun homodimers to activate AP-1-regulated promoters lacking GR binding sites" Chemical senses (1995) vol. 20, pp. 251-255.
Thornberry, N.A. et al., "A novel heterodimeric cysteine protease is required for interleukin-1~ processing in monocytes" Nature (1992) vol. 356, pp. 768-774.
Tissing, WJE et al., "Molecular Determinants of Glucocorticoid Sensitivity and Resistance in Acute Lymphoblastic Leukemia" Leukemia (2003) vol. 17, pp. 17-25.
Wang, J-C et al., "Chromatin immunoprecipitation (ChIP) scanning identifies primary glucocorticoid receptor target genes" Proceedings of the National Academy of Sciences of the United States of America (2004) vol. 101, pp. 15603-15608.
Wellington, C.L. et al., "Caspase cleavage of gene products associated with triplet expansion disorders generates truncated fragments containing the polyglutamine tract" J Biol Chem (1998) vol. 273, pp. 9158-9167.
Willingham, S.B. et al., "NLRP3 (NALP3, Cryopyrin) facilitates in vivo caspase-1 activation, necrosis, and HMGBI release via inflammasome-dependent and -independent pathways" The Journal of Immunology (2009) vol. 183, No. 3, pp. 2008-2015.

(56) References Cited

OTHER PUBLICATIONS

Zou, C., et al., CASPorter: A Novel Inducible Human CASP1/NALP3/ASC Inflammasome Biosensor, Journal of Inflammation Research, 2022, vol. 15, pp. 1183-1194.

Wang, L., et al., VX765 alleviates dextran sulfate sodium-induced colitis in mice by suppressing caspase-1-mediated pyroptosis, Elsevier, International Immunopharmacology 102, 2022, https://doi.org/10.1016/j.intimp.2021.108405.

McKenzie, B., et al., Caspase-1 inhibition prevents glial inflammasome activation and pyroptosis in models of multiple sclerosis, PNAS, 2018, www.pnas.org/lookup/suppl/doi:10.1073/pnas.1722041115/-/DCSupplemental.

Choulaki, C., et al., Enhanced activity of NLRP3 inflammasome in peripheral blood cells of patients with active rheumatoid arthritis, Arthritis Research & Therapy (2015) 17:257, DOI 10.1186/s13075-015-0775-2.

Kim, R., et al., Role for NLRP3 Inflammasome-mediated, IL-1β-Dependent Responses in Severe, Steroid-Resistant Asthma, American Journal of Respiratory and Critical Care Medicine, 2017, vol. 196, No. 3, pp. 283-297.

Chen, S., et al., Blockade of the NLRP3/Caspase-1 Axis Ameliorates Airway Neutrophilic Inflammation in a Toluene Diisocyanate-Induced Murine Asthma Model, Toxicological Sciences, 2019, 170(2), 462-475, doi: 10.1093/toxsci/kfz099.

Laganà, A., et al., Synthetic RNAs for gene regulation: design principles and computational tools, Frontiers in Bioengineering and Biotechnology, 2014, vol. 2, Article 65, doi: 10.3389/fbioe.2014.00065.

\* cited by examiner

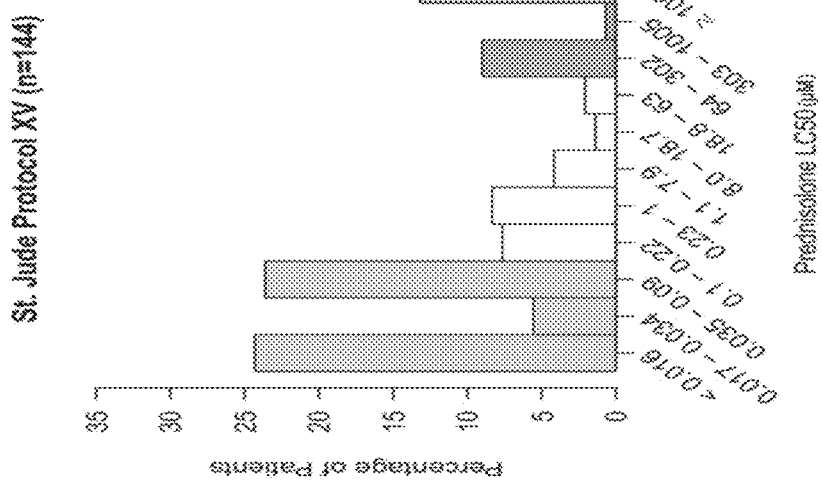
FIG. 1B
FIG. 1C
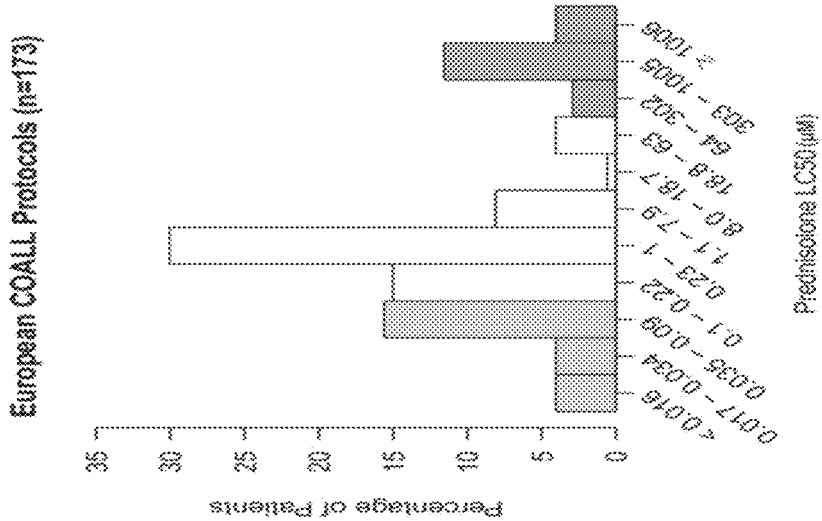
FIG. 1A

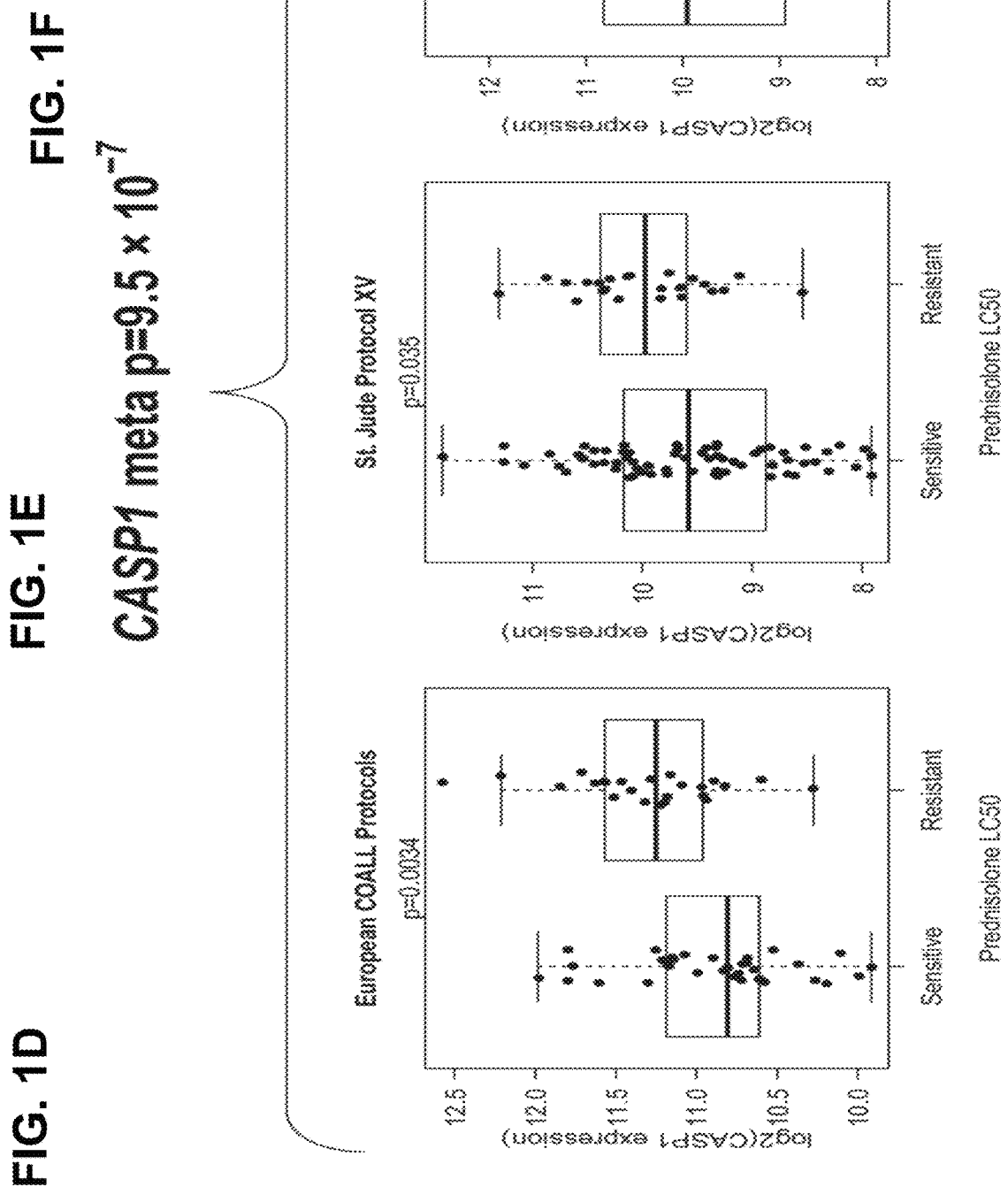

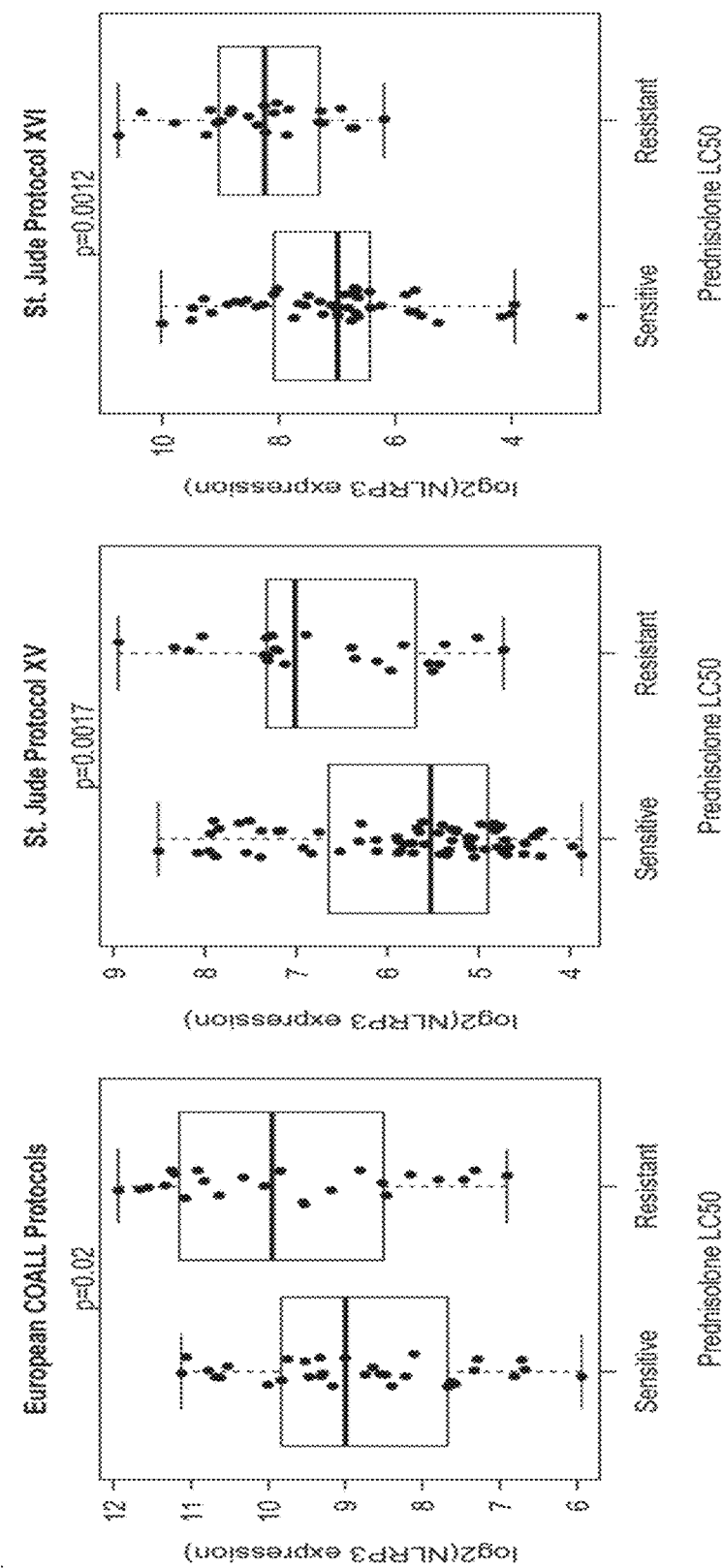

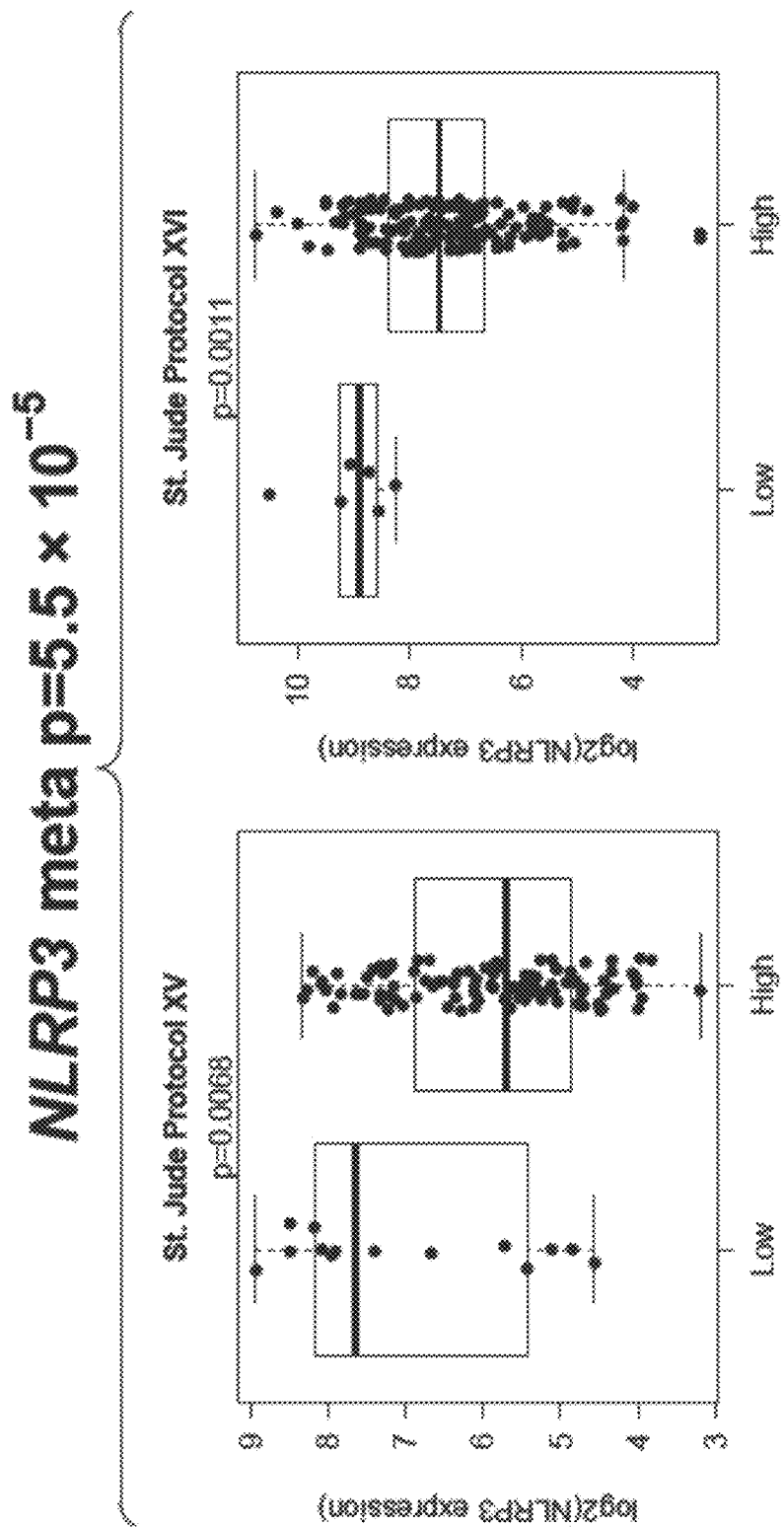

FIG. 6

NLRP3, chr1q44

NLRP3 TSS

−66

CATTAGTTG[C]CCTGTTTTT
cg21991396

CASP1, chr11q23

CASP1 TSS

−23

TCTGAGTGG[C]CGGTACCGA
cg13802966

METHODS FOR OVERCOMING GLUCOCORTICOID RESISTANCE AND FOR DETERMINING GLUCOCORTICOID RESISTANCE POTENTIAL IN CANCER

CROSS-REFERENCE TO RELATED APPLICATIONS

This application is a Continuation application of U.S. application Ser. No. 15/022,464, filed on Mar. 16, 2016, which is the U.S. National Phase application under 35 U.S.C. § 371 of International Patent Application No. PCT/US2014/055824, filed on Sep. 16, 2014, and claims the benefit of U.S. Provisional Patent Application No. 61/878,373, filed on Sep. 16, 2013, all of which applications are incorporated herein by references in their entireties.

STATEMENT AS TO FEDERALLY SPONSORED RESEARCH

This invention was made with government support under grants CA141762, CA021765, GM092666 and CA036401 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 1, 2019, is named 243734.000124_SL.txt and is 32,454 bytes in size.

FIELD OF THE INVENTION

The invention provides methods for overcoming glucocorticoid resistance of cancers by inhibition of CASP1. Also disclosed are diagnostic methods for determining glucocorticoid resistance potential by measuring expression level or promoter methylation status of CASP1 gene and/or NLRP3 gene.

BACKGROUND OF THE INVENTION

Glucocorticoids (GCs) are steroid hormones that regulate multiple physiological processes involved in inflammation, immunity, metabolism and homeostatic functions. They exert their effects by binding to the glucocorticoid receptor (GR, NR3C1), triggering its activation and translocation to the nucleus, leading to transcriptional changes responsible for diminished proliferative capacity and leukemia cell death (Yudt and Cidlowski, 2002).

Synthetic glucocorticoids (e.g., Hydrocortisone (Plenadren, Cortef), Prednisone, Dexamethasone (Intensol), Methylprednisolone (Medrol), Prednisolone (Orapred, Pediapred, Prelone)) are widely prescribed medications used to treat a variety of human diseases with an inflammatory component such as, e.g., asthma, allergies, chronic obstructive pulmonary disease (COPD), swelling, organ transplants, sarcoidosis, spinal cord injuries, ulcerative colitis, irritation, rheumatoid arthritis, chronic inflammatory demyelinating polyneuropathy, Addison's disease, multiple sclerosis (MS), and other autoimmune disorders. However, success of these glucocorticoid treatments is frequently hampered by resistance. For instance, glucocorticoid resistance in asthma has been estimated at 20% -50% (Barnes et al., Am. J. Respir. Critical Care Med., 1995, 152:5125-5142).

Glucocorticoids (e.g., prednisolone and dexamethasone) are also an essential component of curative therapy of acute lymphoblastic leukemia (ALL) and lymphomas. Advancements in the treatment of children with ALL have led to five-year disease-free survival rates exceeding 85% (Pui et al., 2009). However, children whose ALL cells show in vitro resistance to glucocorticoids have a significantly worse treatment outcome (disease-free survival) than patients whose ALL cells are sensitive to glucocorticoids (Den Boer et al., 2003; Dordelmann et al., 1999; Kaspers et al., 1997; Pieters et al., 1991). Yet, little is known about the mechanisms causing the leukemia cells from some patients to exhibit de novo resistance to glucocorticoids.

To find ways to overcome glucocorticoid resistance in acute lymphoblastic leukemia (ALL), lymphomas and other cancers is an urgent problem.

Caspase-1 (CASP1, also known as Interleukin-1β converting enzyme (ICE), apoptosis-related cysteine peptidase, IL-1β convertase, P45 and IL1B convertase, and IL1BC), is an intracellular protease that is known to cleave the precursors of IL-1β and IL-18 into active cytokines (Black et al., FEBS Lett, 247: 386-390 (1989); Kostura et al., Proc. Natl. Acad. Sci. U.S.A., 86:5227-5231 (1989)). Enzymatically active CASP1 is a heterotetramer composed of two subunits of p20 and two subunits of p10 (20 kDa and 10 kDa molecular weight, respectively). These subunits are derived from a 45 kDa proenzyme (p45) by way of a p30 form, through an activation mechanism that is autocatalytic (Thornberry et al., Nature, 356, pp.768-774 (1992)). The CASP1 proenzyme has been divided into several functional domains: a prodomain (pi 4), a p22/20 subunit, a polypeptide linker and a p10 subunit (Thornberry et al., Nature, 356, pp.768-774 (1992); Casano et al., Genomics, 20, pp. 474-481 (1994)).

CASP1 belongs to a family of cysteine proteases that cleave proteins following an aspartic acid residue. Produced as a pro-enzyme, CASP1 requires removal of its CARD (caspase activation and recruitment domain) before it becomes an active enzyme (Schroder and Tschopp, 2010). CARD cleavage is mediated by the formation of large complexes termed inflammasomes, of which the most extensively characterized is the NLRP3-containing inflammasome. NLRP3 (encoded by NLRP3 gene) can be activated by exposure to pathogen associated molecular pattern (PAMP) or damage associated molecular pattern (DAMP) molecules, or by whole pathogens or environmental irritants (Schroder and Tschopp, 2010). There is also emerging evidence that the NLRP3 inflammasome can form in response to host-derived molecules, including extracellular ATP, glucose or monosodium urate crystals (Mariathasan et al., 2006; Martinon et al., 2006; Schroder and Tschopp, 2010; Zhou et al., 2010). In vivo induction of the NLRP3 inflammasome typically results in self-oligomerization, recruitment of the ASC (PYCARD) adaptor protein, and clustering and autoactivation of CASP1.

Human CASP1 has the following sequence (SEQ ID NO: 1, corresponds to GenBank Accession No. NP_150634.1), wherein residues 1-119 of correspond to the propeptide region and residues 120-404 correspond to the mature chain. The p20 and p10 subunits correspond to residues 120-297 (p20) and residues 317-404 (p10), respectively.

(SEQ ID NO: 1)
MADKVLKEKRKLFIRSMGEGTINGLLDELLQTRVLNKEEMEKVKRENATV

MDKTRALIDSVIPKGAQACQICITYICEEDSYLAGTLGLSADQTSGNYLN

MQDSQGVLSSFPAPQAVQDNPAMPTSSGSEGNVKLCSLEEAQRIWKQKSA

EIYPIMDKSSRTRLALIICNEEFDSIPRRTGAEVDITGMTMLLQNLGYSV

DVKKNLTASDMTTELEAFAHRPEHKTSDSTFLVFMSHGIREGICGKKHSE

QVPDILQLNAIFNMLNTKNCPSLKDKPKVIIIQACRGDSPGVVWFKDSVG

VSGNLSLPTTEEFEDDAIKKAHIEKDFIAFCSSTPDNVSWRHPTMGSVFI

GRLIEHMQEYACSCDVEEIFRKVRFSFEQPDGRAQMPTTERVTLTRCFYL

FPGH

See also the following GenBank Accession Nos.:
Alpha precursor isoforms: NP_150634.1 (as above); NP_001244047.1
Beta precursor isoforms: NP_001214.1; NP_001244048.1
Gamma precursor isoforms: NP_150635.1
Delta precursor isoforms: NP_150636.1
Epsilon precursor isoforms: NP_150637.1

Human NLRP3 has the following sequence (SEQ ID NO: 2; corresponds to GenBank Accession No. NP_004886.3), wherein residues 8-93 of correspond to the pyrin death domain found in NALP proteins and residues 220-389 correspond to the NACHT domain and resides 575-891 correspond to Leucine-rich repeats (LRRs), ribonuclease inhibitor domain respectively.

(SEQ ID NO: 2)
MKMASTRCKLARYLEDLEDVDLKKFKMHLEDYPPQKGCIPLPRGQTEKAD

HVDLATLMIDFNGEEKAWAMAVWIFAAINRRDLYEKAKRDEPKWGSDNAR

VSNPTVICQEDSIEEEWMGLLEYLSRISICKMKKDYRKKYRKYVRSRFQC

IEDRNARLGESVSLNKRYTRLRLIKEHRSQQEREQELLAIGKTKTCESPV

SPIKMELLFDPDDEHSEPVHTVVFQGAAGIGKTILARKMMLDWASGTLYQ

DRFDYLFYIHCREVSLVTQRSLGDLIMSCCPDPNPPIHKIVRKPSRILFL

MDGFDELQGAFDEHIGPLCTDWQKAERGDILLSSLIRKKLLPEASLLITT

RPVALEKLQHLLDHPRHVEILGFSEAKRKEYFFKYFSDEAQARAAFSLIQ

ENEVLFTMCFIPLVCWIVCTGLKQQMESGKSLAQTSKTTTAVYVFFLSSL

LQPRGGSQEHGLCAHLWGLCSLAADGIWNQKILFEESDLRNHGLQKADVS

AFLRMNLFQKEVDCEKFYSFIHMTFQEFFAAMYYLLEEEKEGRTNVPGSR

LKLPSRDVTVLLENYGKFEKGYLIFVVRFLFGLVNQERTSYLEKKLSCKI

SQQIRLELLKWIEVKAKAKKLQIQPSQLELFYCLYEMQEEDFVQRAMDYF

PKIEINLSTRMDHMVSSFCIENCHRVESLSLGFLHNMPKEEEEEEKEGRH

LDMVQCVLPSSSHAACSHGLVNSHLTSSFCRGLFSVLSTSQSLTELDLSD

NSLGDPGMRVLCETLQHPGCNIRRLWLGRCGLSHECCFDISLVLSSNQKL

VELDLSDNALGDFGIRLLCVGLKHLLCNLKKLWLVSCCLTSACCQDLASV

LSTSHSLTRLYVGENALGDSGVAILCEKAKNPQCNLQKLGLVNSGLTSVC

CSALSSVLSTNQNLTHLYLRGNTLGDKGIKLLCEGLLHPDCKLQVLELDN

CNLTSHCCWDLSTLLTSSQSLRKLSLGNNDLGDLGVMMFCEVLKQQSCLL

QNLGLSEMYFNYETKSALETLQEEKPELTVVFEPSW

See also the following GenBank Accession Nos.:
Isoform a: NP_004886.3 (as above); NP_001073289.1
Isoform b: NP_899632.1
Isoform c: NP_001120933.1
Isoform d: NP_001120934.1
Isoform e: NP_001230062.1

SUMMARY OF THE INVENTION

As specified in the Background Section, there is a great need in the art to find ways to overcome glucocorticoid resistance in acute lymphoblastic leukemia (ALL), lymphomas and other diseases. The present invention addresses this and other needs by providing methods for overcoming glucocorticoid resistance based on inhibition of CASP1.

Specifically, in one embodiment, the invention provides a method of sensitizing a cancer cell to glucocorticoid-induced apoptosis or cell death, wherein said cell is resistant to glucocorticoid-induced apoptosis or cell death, comprising contacting the cell with an effective amount of an inhibitor of CASP1.

In another embodiment, the invention provides a method of killing a cancer cell, wherein said cell is resistant to glucocorticoid-induced apoptosis or cell death, comprising contacting the cell with an amount of an inhibitor of CASP1 that is effective to sensitize the cell to glucocorticoid-induced apoptosis or cell death and further comprising contacting the cell with an effective amount of a glucocorticoid. In one specific embodiment, the method further comprises contacting the cell with a second agent for inducing apoptosis or cell death.

In one embodiment of the above methods, the cancer cell is in a patient.

In one embodiment of the above methods, the inhibitor of CASP1 directly inhibits expression or function of CASP1. In another embodiment of the above methods, the inhibitor of CASP1 directly inhibits expression or function of NLRP3. In yet another embodiment of the above methods, the inhibitor of CASP1 inhibits NLRP3 inflammasome formation or NLRP3 inflammasome activity. In one specific embodiment of the above methods, the inhibitor of CASP1 is selected from the group consisting of z-VAD-DCB, Ac-YVAD-CHO (SEQ ID NO: 18), Ac-YVAD-chloromethylketone (SEQ ID NO: 19), cytokine response modifier A (crmA), Pralnacasan (VX-740), IDN-6556, VX-765, VRT-043198, ML132, and SNAP.

In one embodiment of the above methods, the glucocorticoid is selected from the group consisting of prednisolone, dexamethasone, hydrocortisone, prednisone, methylprednisolone, cortisol, budesonide, and combinations, enantiomers, optical isomers, diastereomers, N-oxides, crystalline forms, hydrates, metabolites or pharmaceutically acceptable salts thereof.

In a separate embodiment, the invention provides a method of treating a glucocorticoid-resistant cancer in a subject (e.g., human) in need thereof which method comprises administering to the subject (i) a therapeutically effective amount of an inhibitor of CASP1 and (ii) a therapeutically effective amount of a glucocorticoid. In one embodiment, the therapeutically effective amount of the inhibitor of CASP1 is an amount that is effective to sensitize cancer cells within the subject to glucocorticoid-induced apoptosis or cell death. In one embodiment, the cancer is selected from the group consisting of acute lymphoblastic leukemia (ALL), acute myeloblastic leukemia (AML), lymphoma, osteosarcoma, small-cell lung cancer, breast cancer, brain cancer, and multiple myeloma. In one embodiment, the method further comprises administering an additional anticancer treatment to the subject (e.g., a chemotherapy or a radiation therapy).

In another embodiment, the invention provides a method of treating a glucocorticoid-resistant asthma in a subject (e.g., human) in need thereof which method comprises administering to the subject (i) a therapeutically effective amount of an inhibitor of CASP1 and (ii) a therapeutically effective amount of a glucocorticoid.

In one embodiment of the above treatment methods, the inhibitor of CASP1 and the glucocorticoid are administered simultaneously. In one embodiment of the above treatment methods, the inhibitor of CASP1 and the glucocorticoid are administered in the same composition. In one embodiment of the above treatment methods, the inhibitor of CASP1 and the glucocorticoid are administered sequentially.

In one embodiment of the above treatment methods, the inhibitor of CASP1 directly inhibits expression or function of CASP1. In another embodiment of the above treatment methods, the inhibitor of CASP1 directly inhibits expression or function of NLRP3. In yet another embodiment of the above treatment methods, the inhibitor of CASP1 inhibits NLRP3 inflammasome formation or NLRP3 inflammasome activity. In one specific embodiment of the above treatment methods, the inhibitor of CASP1 is selected from the group consisting of z-VAD-DCB, Ac-YVAD-CHO (SEQ ID NO: 18), Ac-YVAD-chloromethylketone (SEQ ID NO: 19), cytokine response modifier A (crmA), Pralnacasan (VX-740), IDN-6556, VX-765, VRT-043198, ML132, and SNAP.

In one embodiment of the above treatment methods, the glucocorticoid is selected from the group consisting of prednisolone, dexamethasone, hydrocortisone, prednisone, methylprednisolone, cortisol, budesonide, and combinations, enantiomers, optical isomers, diastereomers, N-oxides, crystalline forms, hydrates, metabolites or pharmaceutically acceptable salts thereof.

In a separate embodiment, the invention provides a pharmaceutical composition comprising a CASP1 inhibitor, a glucocorticoid, and a pharmaceutically acceptable carrier or excipient. In one embodiment, the CASP1 inhibitor is selected from the group consisting of z-VAD-DCB, Ac-YVAD-CHO (SEQ ID NO: 18), Ac-YVAD-chloromethylketone (SEQ ID NO: 19), cytokine response modifier A (crmA), Pralnacasan (VX-740), IDN-6556, VX-765, VRT-043198, ML132, and SNAP. In one embodiment, the glucocorticoid is selected from the group consisting of prednisolone, dexamethasone, hydrocortisone, prednisone, methylprednisolone, cortisol, budesonide, and combinations, enantiomers, optical isomers, diastereomers, N-oxides, crystalline forms, hydrates, metabolites or pharmaceutically acceptable salts thereof.

In a separate embodiment, the invention provides a method for determining whether a cancer in a subject (e.g., human) is likely to be resistant to a glucocorticoid treatment, said method comprising the steps of:
(a) determining the expression level of CASP1 gene and/or NLRP3 gene in cancer cells from the subject;
(b) comparing the expression level of each gene determined in step (a) with a corresponding control expression level for that gene, and
(c) (i) identifying that the cancer in the subject is likely to be resistant to the glucocorticoid treatment when the expression level of CASP1 gene and/or NLRP3 gene in step (a) is increased by at least 1.5 fold as compared to the corresponding control expression level or (ii) identifying that the cancer in the subject is not likely to be resistant to the glucocorticoid treatment when the expression level of CASP1 gene and/or NLRP3 gene in step (a) is not increased or is increased by less than 1.5 fold as compared to the corresponding control expression level.

In one embodiment, the corresponding control expression level is the expression level of the same gene in similarly processed cancer cells of the same type which are sensitive to glucocorticoid treatment. In another embodiment, the corresponding control expression level is a predetermined standard. In one embodiment, the expression level of CASP1 gene and/or NLRP3 gene is determined using a method selected from the group consisting of amplification-based assays, hybridization-based assays, flap-endonuclease-based assays, and direct mRNA capture.

In a separate embodiment, the invention provides a method for determining whether a cancer in a subject is likely to be resistant to a glucocorticoid treatment, said method comprising the steps of:
(a) determining the methylation level of CASP1 gene promoter and/or NLRP3 gene promoter in cancer cells from the subject;
(b) comparing the methylation level of each gene promoter determined in step (a) with a corresponding control methylation level for that gene promoter, and
(c) (i) identifying that the cancer in the subject is likely to be resistant to glucocorticoid treatment when the methylation level of CASP1 gene promoter and/or NLRP3 gene promoter in step (a) is decreased by at least 1.5 fold as compared to the corresponding control methylation level or (ii) identifying that the cancer in the subject is not likely to be resistant to glucocorticoid treatment when the methylation level of CASP1 gene promoter and/or NLRP3 gene promoter in step (a) is not increased or is increased by less than 1.5 fold as compared to the corresponding control methylation level.

In one specific embodiment, the CASP1 gene promoter comprises the sequence GTCGGGGAAGGTTTTGAGAAAGAAGGGTCCCTGGACAAGAACCTTGTCATTTTCTGA GTGGCCGGTACCGAAAAGAGAGGAGGGAAGAACACACTGACTTTGACTTTCATACG AAGCGGAAG (SEQ ID NO: 3). In one specific embodiment, the NLRP3 gene promoter comprises the sequence CTCCTTTGACTTCAACTCCTTATCACTTCTCAAACAGGTTACAGTATCGGGGCATTAG TTGCCCTGTTTTTAAAAGAACGACTACCCAGTTCTACCGTAGCACTTCACCAACAAG TGGCATT (SEQ ID NO: 4). In one embodiment, the corresponding control methylation level is the methylation level of the same gene promoter in similarly processed cancer cells of the same type which are sensitive to glucocorticoid treatment. In another embodiment, the corresponding control methylation level is a predetermined standard. In one embodiment, the methylation level is determined using a method selected from the group consisting of methods based on the use of methylation-sensitive restriction endonucleases, bisulfite DNA sequencing, hybridization following bisulfite conversion, Restriction Landmark Genome Scanning (RLGS), and Methylation-Sensitive Representational Difference Analysis (MS-RDA).

In one embodiment of the above diagnostic methods, the method comprises obtaining the cancer cells from the subject prior to step (a). In one embodiment, the cancer cells are derived from peripheral blood. In another embodiment, the cancer cells are derived from bone marrow. In one embodiment, the cancer is selected from the group consisting of acute lymphoblastic leukemia (ALL), acute myeloblastic leukemia (AML), lymphoma, osteosarcoma, small-cell lung cancer, breast cancer, brain cancer, and multiple myeloma.

In one embodiment of the above diagnostic methods, the subject identified as having cancer which is likely to be resistant to glucocorticoid treatment is treated with a combination of an inhibitor of CASP1 and a glucocorticoid. In one embodiment, the inhibitor of CASP1 directly inhibits expression or function of CASP1. In another embodiment, the inhibitor of CASP1 directly inhibits expression or function of NLRP3. In yet another embodiment, the inhibitor of CASP1 inhibits NLRP3 inflammasome formation or NLRP3 inflammasome activity. In one specific embodiment, the inhibitor of CASP1 is selected from the group consisting of z-VAD-DCB, Ac-YVAD-CHO (SEQ ID NO: 18), Ac-YVAD-chloromethylketone (SEQ ID NO: 19), cytokine response modifier A (crmA), Pralnacasan (VX-740), IDN-6556, VX-765, VRT-043198, ML132, and SNAP.

In one embodiment of the above diagnostic methods, the subject identified as having cancer which is likely to be resistant to glucocorticoid treatment is treated with increased doses of a glucocorticoid (e.g., 1.5 fold increased doses of a glucocorticoid).

In another embodiment of the above diagnostic methods, the subject identified as having cancer which is likely to be resistant to glucocorticoid treatment is treated with a non-glucocorticoid chemotherapeutic and/or radiation.

In one embodiment of the above diagnostic methods, the subject identified as having cancer which is not likely to be resistant to glucocorticoid treatment is treated with a glucocorticoid.

In one embodiment of the above diagnostic methods, the glucocorticoid used for treatment is selected from the group consisting of prednisolone, dexamethasone, hydrocortisone, prednisone, methylprednisolone, cortisol, budesonide, and combinations, enantiomers, optical isomers, diastereomers, N-oxides, crystalline forms, hydrates, metabolites or pharmaceutically acceptable salts thereof.

In a separate embodiment, the invention provides a kit for diagnosing likelihood of cancer resistance to glucocorticoid treatment, said kit comprising one or more pairs of oligonucleotides directed toward CASP1 and/or NLRP3 nucleic acid, wherein said pairs of oligonucleotides can be used to determine the expression level of CASP1 gene and/or NLRP3 gene. In one embodiment, the kit further comprises a detection means. In one embodiment, the kit further comprises an amplification means. In one embodiment, the kit further comprises one or more pairs of control oligonucleotides. In one embodiment, the kit further comprises instructions for use.

In another embodiment, the invention provides a kit for diagnosing likelihood of cancer resistance to glucocorticoid treatment, said kit comprising antibodies directed toward CASP1 protein and/or NLRP3 protein, wherein said antibodies can be used to determine the expression level of CASP1 and/or NLRP3 protein. In one embodiment, the kit further comprises a detection means. In one embodiment, the kit further comprises one or more control antibodies. In one embodiment, the kit further comprises instructions for use.

In another embodiment, the invention provides a kit for diagnosing likelihood of cancer resistance to glucocorticoid treatment, said kit comprising means for detecting promoter methylation of CASP1 gene and/or NLRP3 gene. In one embodiment, the kit further comprises instructions for use.

These and other aspects of the present invention will be apparent to those of ordinary skill in the art in the following description, claims and drawings.

BRIEF DESCRIPTION OF THE DRAWINGS

FIGS. 1A-I demonstrate that glucocorticoid resistant leukemia cells have higher expression of CASP1 and NLRP3. Primary leukemia cells were obtained by bone marrow aspirates from 444 patients with newly diagnosed acute lymphoblastic leukemia, then isolated and analyzed for their sensitivity to prednisolone using the MTT assay (see Example 1, Methods) (Holleman et al., 2004). Distributions of measured LC50 values are shown for the three independent cohorts of patients; sensitive and resistant leukemias are highlighted in green and red, respectively (panels A-C). CASP1 (panels D-F) and NLRP3 (panels G-I) expression was significantly higher in glucocorticoid resistant leukemia cells from these three cohorts of newly diagnosed patients. Exact Wilcoxon Mann-Whitney Rank Sum test p-values are shown for panels D-I, with Stouffer's Z-score method meta-analysis p-values shown above panels D-F and panels G-I as described in methods section.

FIGS. 2A-G demonstrate that hypo-methylation of the CASP1 and NLRP3 promoter region is associated with higher CASP1 and NLRP3 expression in leukemia cells. In both patient cohorts for whom DNA was available for DNA methylation analysis (St. Jude Protocols XV and XVI), lower levels of CASP1 (panels A, B and C) and NLRP3 (panels D, E and F) methylation were found in leukemia cells with higher expression of CASP1 and NLRP3. For both CASP1 and NLRP3 methylation status, the DNA methylation site (CpG) was within 100 basepairs of the transcription start site (FIG. 6). k-means clustering analysis (▲ represents k-means identified group A, ● represents k-means identified group B, pink and blue squares represent k-means identified centers for group A and B respectively) utilizing only CASP1 and NLRP3 methylation status significantly discriminated sensitive leukemias (green symbols, higher methylation) from resistant leukemias (red symbols, lower methylation) in both St. Jude Protocol XV and St. Jude Protocol XVI (panel G and FIG. 5) patients. Exact Wilcoxon Mann-Whitney Rank Sum test p-values are shown for panels A, B, D, E, with Stouffer's Z-score method meta-analysis p-values shown above panels A-B and panels D-E.

FIG. 3A discloses SEQ ID NOS 23-24, respectively, in order of appearance. FIG. 3B discloses "LLID" and "AAAA" as SEQ ID NOS 20 and 25, respectively.

FIG. 6 shows DNA methylation analysis probe locations for CASP1 and NLRP3 relative to the transcription start sites of these genes. The specific base analyzed is shown in square brackets with the genomic context surrounding this site. FIG. 6 discloses SEQ ID NOS 26-27, respectively, in order of appearance.

DETAILED DESCRIPTION OF THE INVENTION

Figure 2A:
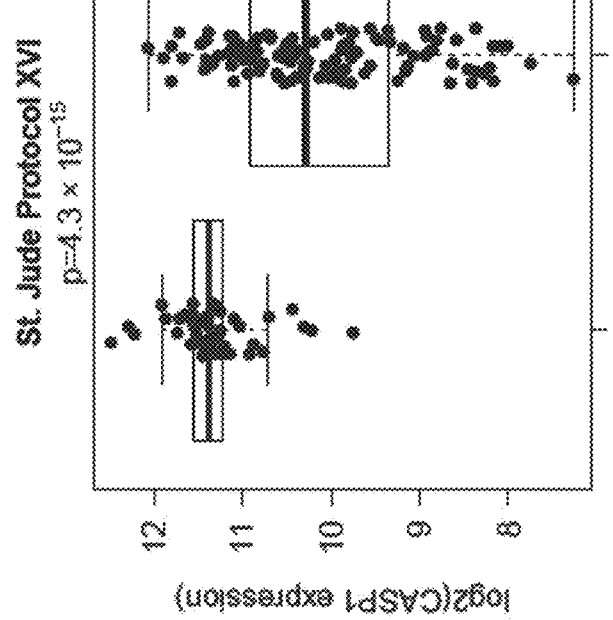

The present invention is based on an unexpected observation by the inventors that primary acute lymphoblastic leukemia (ALL) cells that exhibited de novo resistance to glucocorticoids had higher expression of CASP1 and its activator NLRP3 (NLR family, pyrin domain containing 3). The present inventors also found significantly lower promoter methylation of these two genes in leukemia cells exhibiting higher expression of CASP1 and NLRP3. As demonstrated in the Examples section, below, the mechanism involves CASP1 cleavage of the glucocorticoid receptor (GR) in its transactivation domain, thereby reducing cellular levels of functional GR and altering cellular response to glucocorticoid treatment.

Definitions

The term "glucocorticoid resistant cancer" is used herein to refer to a cancer in which the cancer cells are resistant to being killed by the concentrations of a glucocorticoid that are used to kill cells in a drug-sensitive cancer of the same type. Non-limiting examples of glucocorticoids for which resistance can occur in cancer cells include prednisolone, dexamethasone, hydrocortisone, prednisone, methylprednisolone, cortisol, budesonide, and combinations, enantiomers, optical isomers, diastereomers, N-oxides, crystalline forms, hydrates, metabolites or pharmaceutically acceptable salts thereof. Non-limiting examples of cancers in which glucocorticoid resistance is frequently observed include acute lymphoblastic leukemia (ALL, including both B- and T-lineage ALL), acute myeloblastic leukemia (AML), lymphoma, osteosarcoma, small-cell lung cancer, breast cancer, brain cancer, and multiple myeloma.

The relative resistance of a cancer cell to a glucocorticoid may be determined by calculating the drug concentration that is lethal to 50% of the cells (LC50). See, e.g., Holleman et al., 2004. As disclosed in the Example 1, below, with respect to resistance of ALL to prednisolone, glucocorticoid resistant ALL was defined as having an LC50 greater than or equal to 64 µM, whereas glucocorticoid sensitive cases were defined as having an LC50 less than 0.1 µM (for LC50 measured using the method of Holleman et al., 2004).

As used herein, the terms "CASP1 inhibitor" and "inhibitor of CASP1" encompass direct inhibitors of expression and/or function of CASP1 as well as direct inhibitors of expression and/or function of NLRP3, inhibitors of NLRP3 inflammasome formation and inhibitors of NLRP3 inflammasome activity.

The term "a control level" as used herein encompasses predetermined standards (e.g., a published value in a reference) as well as levels determined experimentally in similarly processed samples from control cancer cells of the same type which are sensitive to glucocorticoid treatment (preferably, sensitive to treatment with the same glucocorticoid predisposition to resistance to which is being tested). As used herein, the term "similarly processed" refers to samples which have been obtained using the same protocol.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. E.g., in connection with cancer the term "treat" may mean eliminate or reduce a patient's tumor burden, or prevent, delay or inhibit metastasis, etc.

As used herein the term "therapeutically effective" applied to dose or amount refers to that quantity of a compound or pharmaceutical composition that is sufficient to result in a desired activity upon administration to a subject in need thereof. Within the context of the present invention, when the term "therapeutically effective" is used in connection with a CASP1 inhibitor, it refers to an amount of said CASP1 inhibitor or a pharmaceutical composition containing such CASP1 inhibitor that is effective to sensitize cancer cells within the treated subject to glucocorticoid-induced apoptosis or cell death. When the term "therapeutically effective" is used in connection with a glucocorticoid, it refers to that quantity of the glucocorticoid or a pharmaceutical composition containing such glucocorticoid that is sufficient to delay the manifestation, arrest the progression, relieve or alleviate at least one symptom of a disorder treated by the methods of the present invention. Note that when a combination of active ingredients is administered (e.g., a combination of a CASP1 inhibitor and a glucocorticoid) the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "subject" refers to any mammal. In a preferred embodiment, the subject is human.

As used in this specification and the appended claims, the singular forms "a," "an," and "the" include plural references unless the context clearly dictates otherwise.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A practical Approach*, Volumes I and II (D. N. Glover ed. 1985); *Oligonucleotide Synthesis* (M J. Gait ed. 1984); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; B. Perbal, *A practical Guide To Molecular Cloning* (1984); F. M. Ausubel et al. (eds.), *Current Protocols in Molecular Biology*, John Wiley & Sons, Inc. (1994); among others.

Treatment/Therapeutic Methods of the Invention

In one embodiment, the invention provides a method for sensitizing a cancer cell to glucocorticoid-induced apoptosis or cell death, wherein said cell is resistant to glucocorticoid-induced apoptosis or cell death, comprising contacting the cell with an effective amount of an inhibitor of CASP1.

In another embodiment, the invention provides a method for killing a cancer cell, wherein said cell is resistant to glucocorticoid-induced apoptosis or cell death, comprising contacting the cell with an amount of an inhibitor of CASP1 that is effective to sensitize the cell to glucocorticoid-induced apoptosis or cell death and further comprising contacting the cell with an effective amount of a glucocorticoid.

In a further embodiment, the invention provides a method of treating a glucocorticoid-resistant cancer in a subject in need thereof which method comprises administering to the subject (i) a therapeutically effective amount of an inhibitor of CASP1 and (ii) a therapeutically effective amount of a glucocorticoid. In one embodiment, the therapeutically effective amount of the inhibitor of CASP1 is an amount that is effective to sensitize cancer cells within the subject to glucocorticoid-induced apoptosis or cell death. The inhibitor of CASP1 and the glucocorticoid can be administered simultaneously (in the same composition or in separate compositions) or they can be administered sequentially (preferably, with the inhibitor of CASP1 being administered prior to the glucocorticoid). In one specific embodiment, the treatment method of the invention further comprises administering an additional anti-cancer treatment to the subject.

Non-limiting examples of inhibitors of CASP1 useful in the methods of the invention are small molecules and antibodies, including inhibitors of CASP1 protein function as well as inhibitors of CASP1 expression (such as, e.g., interfering RNA, dsRNA, RNA polymerase III transcribed DNAs, ribozymes, and antisense nucleic acids). Inhibitors of CASP1 useful in the methods of the invention include (i) molecules which directly inhibit expression or function of CASP1, (ii) molecules which directly inhibit expression or function of NLRP3, and (iii) molecules which inhibit NLRP3 inflammasome formation or NLRP3 inflammasome activity. A more detailed discussion of the inhibitors is provided below.

The inhibitors of CASP1 can be used in treatment/therapeutic methods described above or can be administered to a nonhuman mammal for the purposes of obtaining preclinical data. Exemplary nonhuman mammals to be treated include nonhuman primates, dogs, cats, rodents and other mammals in which preclinical studies are performed. Such mammals may be established animal models for a disease to be treated or may be used to study toxicity of the inhibitor of interest. In each of these embodiments, dose escalation studies may be performed in the mammal.

The present invention can be used to treat any cancer which can be treated by a glucocorticoid and can acquire glucocorticoid resistance accompanied with increased expression of CASP1 and/or NLRP3. Non-limiting examples of cancers treatable by the methods of the invention include, for example, carcinomas, lymphomas, sarcomas, blastomas, and leukemias. Non-limiting specific examples, include, for example, acute lymphoblastic leukemia (ALL), acute myeloblastic leukemia (AML), lymphoma, osteosarcoma, small-cell lung cancer, breast cancer, brain cancer, and multiple myeloma. Additional examples of cancers treatable by the methods of the invention include, for example, pancreatic cancer, liver cancer, lung cancer, prostate cancer, colon cancer, renal cancer, bladder cancer, head and neck carcinoma, thyroid carcinoma, soft tissue sarcoma, ovarian cancer, primary or metastatic melanoma, squamous cell carcinoma, basal cell carcinoma, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, glioblastoma, astrocytoma, medulloblastoma, craniopharyngioma, ependymoma, pinealoma, hemangioblastoma, acoustic neuroma, oligodendroglioma, meningioma, retinoblastoma, leukemia, neuroblastoma, small cell lung carcinoma, bladder carcinoma, lymphoma, multiple myeloma, medullary carcinoma, B cell lymphoma, T cell lymphoma, myeloma, leukemia, chronic myeloid leukemia, acute myeloid leukemia, chronic lymphocytic leukemia, acute lymphocytic leukemia, hematopoietic neoplasias, thymoma, sarcoma, non-Hodgkins lymphoma, Hodgkins lymphoma, uterine cancer, renal cell carcinoma, hepatoma, etc.

The methods of the present invention can be also applicable to other diseases (e.g., inflammatory and autoimmune diseases such as, e.g., asthma) which are treated with glucocorticoids and can acquire glucocorticoid resistance accompanied with increased expression of CASP1.

It is contemplated that when used to treat various diseases, CASP1 inhibitors and glucocorticoids can be further combined with other therapeutic agents suitable for treatment of such diseases. Also, two or more CASP1 inhibitors and/or two or more glucocorticoids may be co-administered to generate additive or synergistic effects. Suitable therapeutically effective dosages for each agent may be lowered due to the additive action or synergy.

Therapeutic methods of the invention can be combined with additional anti-cancer therapies such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, VEGF antagonists, VEGF receptor antagonists (such as anti-VEGF antibodies), VEGF variants, soluble VEGF receptor fragments, aptamers capable of blocking VEGF or VEGFR, neutralizing anti-VEGFR antibodies, inhibitors of VEGFR tyrosine kinases, and any combinations thereof (e.g., anti-hVEGF antibody A4.6.1, bevacizumab or ranibizumab). See also Carmeliet and Jain (2000).

Non-limiting examples of chemotherapeutic compounds which can be used in combination treatments of the present invention include, for example, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estramnustine, etoposide, exemestane, filgrastim, fludarabine, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan); growth factor signal transduction kinase inhibitors; mitochondrial dysfunction inducers; and chromatin disruptors.

CASP1 Inhibitors of the Invention

The present invention encompasses various small molecule inhibitors of CASP1 gene expression and/or CASP1 protein function. The present invention also encompasses various small molecule inhibitors of NLRP3 gene expression and/or NLRP3 protein function.

Small molecules are a diverse group of synthetic and natural substances generally having low molecular weights (preferably less than about 2000 Daltons, less than about 1000 Daltons, or less than about 500 Daltons). Small molecules, without limitation, may be, for example, nucleic acids, peptides, polypeptides, peptide nucleic acids, peptidomimetics, carbohydrates, lipids, or other organic (carbon containing) or inorganic molecules and may be synthetic or naturally occurring or optionally derivatized. Such small molecules may be a therapeutically deliverable substance or may be further derivatized to facilitate delivery or targeting.

Many CASP1 inhibitors useful in the methods of the present invention are known in the art. Specific non-limiting examples of useful CASP1 inhibitors include, e.g., 2-valyl-alanyl-3-amino-4-oxo-5-(2,6-dichlorobenzoyl)oxopentanoic acid (z-VAD-DCB), Ac-Tyr-Val-Ala-Asp-aldehyde (Ac-YVAD-CHO) (SEQ ID NO: 18), Ac-YVAD-chloromethylketone (SEQ ID NO: 19), cytokine response modifier A (crmA), Pralnacasan (VX-740; (1S,9S)-N-[(2R,3S)-2-ethoxy-5-oxooxolan-3-yl]-9-(isoquinoline-1-carbonylamino)-6,10-dioxo-2,3,4,7,8,9-hexahydro-1H-pyridazino[1,2-a] diazepine-1-carboxamide), IDN-6556 (N-[2-(tert-butyl)phenyl]-2-oxo), VX-765 ((S)-1-((R)-2-(4-amino-3-chlorobenzamido)-3,3-dimethylbutanoyl)-N-((2S, 3S)-2-ethoxy-5-oxotetrahydro-furan-3-yl)pyrrolidine-2-carboxamide), VRT-043198 ((S)-3-((S)-1-((R)-2-(4-amino-3-chlorobenzamido)-3,3-dimethylbutanoyl)pyrrolidine-2-carboxamido)-4-oxobutanoic acid), . and ML132 (CID-4462093; NCGC-00183434), Of these, the last four agents are active site inhibitors that act through reversible (Pralnacasan and VX-765) or irreversible (IDN-6556) covalent modification of the catalytic cysteine residue. See, e.g., Boxer et al., ChemMedChem (2010), 5(5), 730-738; Eda, (2009), 251-287; Boxer et al., A small molecule inhibitor of Caspase 1. 2010 Feb. 25 [Updated 2011 Mar. 3]. In: Probe Reports from the NIH Molecular Libraries Program [Internet]. Bethesda (Md.): National Center for Biotechnology Information (US); 2010-. Available from: http://www.ncbi.nlm.nih.gov/books/NBK56241/. Additional non-limiting examples of useful inhibitors are provided, e.g., in the following documents: International Patent Publ. Nos. WO 03/103599, WO 09/083929, WO 05/115362, WO 2011/094426, WO 04/058718, WO 04/002961, WO 03/088917, WO 03/068242, WO 03/042169, WO 98/16505, WO 93/09135, WO 03/106460, WO 03/103677, WO 03/104231, WO 02/085899, WO 00/55114, WO 00/55127, WO 00/61542, WO 01/05772, WO 01/10383, WO 01/16093, WO 01/42216, WO 01/72707, WO 01/90070, WO 01/94351, WO 02/094263, WO 02/42278, WO 99/47545, WO 01/90063, WO 02/22611, WO 02/12638, WO 95/35308, WO 97/22619, WO 01/00658, WO 98/10778, WO 03/072528, WO 03/032918, WO 05/003100, WO 04/002401, WO 00/61542, WO 00/55114, WO 99/47154, WO 99/56765, WO 93/05071, WO 04/058718, WO 04/002961, WO 95/35308, WO 97/22619, WO 99/47545, WO 01/90063, WO 95/35308, WO 97/22619, WO 99/47545, WO 2002/089749, WO 99/36426, WO 98/16505, WO 98/16504, and WO 01/90063; U.S. Pat. Nos. 6,184,210; 6,184,244; 6,187,771; 6,197,750; 6,242,422; 5,716,929; 6,204,261; 7,115,654; 6,693,096; 6,610,683; 6,531,467; 6,528,506; 6,200,969; 6,716,818; 6,620,782; 6,566,338; 6,495,522; 6,355,618; 6,153,591; 6,083,981; 5,932,549; 5,919,790; 5,744,451; 6,316,415; 5,932,549; 5,919,790; 5,744,451; U.S. Patent Appl. Pub. Nos. 2002/0058630, 2004/0014753, 2004/0009966, 2003/0236296, European Patent Nos. EP 1082127, EP 1049703, EP 0932600, EP 0932598, EP 0600880, and EP 1378573.

The above compounds may be obtained by methods known to skilled practitioners and the methods disclosed in documents cited herein.

Additional CASP1 inhibitors can be isolated from natural sources (for example, plants, fungi, microbes and the like) or isolated from random or combinatorial chemical libraries of synthetic or natural compounds, or synthesized. See Werner et al., (2006) Brief Funct. Genomic Proteomic 5(1):32-6. Many random or combinatorial libraries are known in the art that can be used. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) Tib Tech 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups.

Examples of chemically synthesized libraries are described in Fodor et al., (1991) Science 251:767-773; Houghten et al., (1991) Nature 354:84-86; Lam et al., (1991) Nature 354:82-84; Medynski, (1994) BioTechnology 12:709-710; Gallop et al., (1994) J. Medicinal Chemistry 37(9):1233-1251; Ohlmeyer et al., (1993) Proc. Natl. Acad. Sci. USA 90:10922-10926; Erb et al., (1994) Proc. Natl. Acad. Sci. USA 91:11422-11426; Houghten et al., (1992) Biotechniques 13:412; Jayawickreme et al., (1994) Proc. Natl. Acad. Sci. USA 91:1614-1618; Salmon et al., (1993) Proc. Natl. Acad. Sci. USA 90:11708-11712; PCT Publication No. WO 93/20242, dated Oct. 14, 1993; and Brenner et al., (1992) Proc. Natl. Acad. Sci. USA 89:5381-5383.

Examples of phage display libraries are described in Scott et al., (1990) Science 249:386-390; Devlin et al., (1990) Science, 249:404-406; Christian, et al., (1992) J. Mol. Biol. 227:711-718; Lenstra, (1992) J. Immunol. Meth. 152:149-157; Kay et al., (1993) Gene 128:59-65; and PCT Publication No. WO 94/18318.

Screening the libraries can be accomplished by any variety of commonly known methods. See, for example, the following references, which disclose screening of peptide libraries: Parmley and Smith, (1989) Adv. Exp. Med. Biol. 251:215-218; Scott and Smith, (1990) Science 249:386-390; Fowlkes et al., (1992) BioTechniques 13:422-427; Oldenburg et al., (1992) Proc. Natl. Acad. Sci. USA 89:5393-5397; Yu et al., (1994) Cell 76:933-945; Staudt et al., (1988) Science 241:577-580; Bock et al., (1992) Nature 355:564-566; Tuerk et al., (1992) Proc. Natl. Acad. Sci. USA 89:6988-6992; Ellington et al., (1992) Nature 355:850-852; U.S. Pat. Nos. 5,096,815; 5,223,409; and 5,198,346, all to Ladner et al.; Rebar et al., (1993) Science 263:671-673; and PCT Pub. WO 94/18318.

Identification and screening of CASP1 inhibitors can be further facilitated by X-ray crystallography, neutron diffraction, nuclear magnetic resonance spectrometry, and other techniques for structure determination. These techniques provide for the rational design or identification of inhibitors.

The present invention also encompasses inhibitors of CASP1 gene expression, including inhibitors of CASP1 protein production, as well as inhibitors of NLRP3 gene expression, including inhibitors of NLRP3 protein production. Non-limiting examples of such useful expression inhibitors include, e.g., interfering RNA (e.g., siRNA or shRNA), dsRNA, RNA polymerase III transcribed DNAs, ribozymes, and antisense nucleic acids.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the target DNA sequence can be synthesized, e.g., by conventional phosphodiester techniques (Dallas et al., (2006) Med. Sci. Monit. 12(4):RA67-74; Kalota et al., (2006) Handb. Exp. Pharmacol. 173:173-96; Lutzelburger et al., (2006) Handb. Exp. Pharmacol. 173:243-59).

siRNA comprises a double stranded structure typically containing 15 to 50 base pairs and preferably 21 to 25 base pairs and having a nucleotide sequence identical or nearly identical to an expressed target gene or RNA within the cell. Antisense polynucleotides include, but are not limited to: morpholinos, 2'-O-methyl polynucleotides, DNA, RNA and the like.

RNA polymerase III transcribed DNAs contain promoters, such as the U6 promoter. These DNAs can be transcribed to produce small hairpin RNAs in the cell that can function as siRNA or linear RNAs that can function as antisense RNA. The inhibitor may be polymerized in vitro, recombinant RNA, contain chimeric sequences, or derivatives of these groups. The inhibitor may contain ribonucleotides, deoxyribonucleotides, synthetic nucleotides, or any suitable combination such that the target RNA and/or gene is inhibited. In addition, these forms of nucleic acid may be single, double, triple, or quadruple stranded. (see for example Bass (2001) Nature, 411, 428 429; Elbashir et al., (2001) Nature, 411, 494 498; and PCT Publication Nos. WO 00/44895, WO 01/36646, WO 99/32619, WO 00/01846, WO 01/29058, WO 99/07409, WO 00/44914).

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of mRNA sequences are also within the scope of the present invention. Scanning the target molecules for ribozyme cleavage sites that include the following sequences, GUA, GUU, and GUC initially identifies specific ribozyme cleavage sites within any potential RNA target. Once identified, short RNA sequences of between about 15 and 20 ribonucleotides corresponding to the region of the target gene containing the cleavage site can be evaluated for predicted structural features such as secondary structure that may render the oligonucleotide sequence unsuitable. The suitability of candidate targets can also be evaluated by testing their accessibility to hybridization with complementary oligonucleotides using, e.g., ribonuclease protection assays.

Expression inhibitors of the present invention can be prepared by known methods. These include techniques for chemical synthesis such as, e.g., by solid phase phosphoamite chemical synthesis. Alternatively, antisense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. See, e.g., Weintraub, H. et al., Antisense RNA as a molecular tool for genetic analysis, Reviews—Trends in Genetics, Vol. 1 (1) 1986.

Various modifications to the oligonucleotides can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Aptamers nucleic acid sequences are readily made that bind to a wide variety of target molecules. The aptamer nucleic acid sequences useful in the methods of the invention can be comprised entirely of RNA or partially of RNA, or entirely or partially of DNA and/or other nucleotide analogs. Aptamers are typically developed to bind particular ligands by employing known in vivo or in vitro (most typically, in vitro) selection techniques known as SELEX (Systematic Evolution of Ligands by Exponential Enrichment). Methods of making aptamers are described in, for example, Ellington and Szostak (1990) Nature 346:818, Tuerk and Gold (1990) Science 249:505, U.S. Pat. No. 5,582,981; PCT Publication No. WO 00/20040; U.S. Pat. No. 5,270,163; Lorsch and Szostak (1994) Biochem. 33:973; Mannironi et al., (1997) Biochem. 36:9726; Blind (1999) Proc. Nat'l. Acad. Sci. USA 96:3606-3610; Huizenga and Szostak (1995) Biochem. 34:656-665; PCT Publication Nos. WO 99/54506, WO 99/27133, and WO 97/42317; and U.S. Pat. No. 5,756,291.

Another class of CASP1 inhibitors useful in the methods of the invention are inhibitory antibodies. The antibodies for use in accordance with the present invention may be monoclonal or polyclonal as appropriate. The antibody fragments can be also used and include, for example, Fab, Fab', F(ab')$_2$ or Fv fragments. The antibody may be a single chain antibody. Other suitable modifications and/or agents will be apparent to those skilled in the art. Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., Proc. Natl. Acad. Sci. U.S.A. 81,6851 (1985); Takeda, et al., Nature 314,452 (1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. Additionally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

In certain embodiments, anti-idiotypic antibodies can be also used. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See, e.g., U.S. Pat. No. 4,699,880. In one embodiment, antibodies are raised against CASP1 or a portion thereof, and these antibodies are used in turn to produce an anti-idiotypic antibody.

Preferably, the CASP1 inhibitory antibodies useful in the methods of the invention provide intracellular targeting. Intracellular targeting can be accomplished, for example, through the use of intracellularly expressed antibodies referred to as intrabodies.

To screen for antibodies which bind to a particular epitope on the antigen of interest (e.g., CASP1), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al. (1995) J. Biol. Chem. 270:1388-1394, can be performed to determine whether the antibody binds an epitope of interest.

Additional antibodies useful in the methods of the present invention can be also generated and selected using phage display approach as described, e.g., in U.S. Patent Appl. Publ. No. 2008/0213268.

Antibodies can be further modified to generate antibody mutants with improved physical, chemical and or biological properties over the parent antibody. See, e.g., Amit et al. (1986) Science 233:747-753; Chothia et al. (1987) J. Mol. Biol. 196:901-917; EP 239400B; Cunningham and Wells (1989) Science 244:1081-1085.

Antibodies can be prepared by standard means. See, e.g., Kohler et al., Nature 256:495-497 (1975) and Eur. J. Immunol. 6:511-519 (1976); Milstein et al., Nature 266:550-552 (1977); Koprowski et al., U.S. Pat. No. 4,172,124; Harlow and Lane, "Antibodies: A Laboratory Manual," (Cold Spring Harbor Laboratory: Cold Spring Harbor, N.Y., 1988); and "Current Protocols In Molecular Biology," (Ausubel et al., Eds.; John Wiley & Sons: New York, N.Y., 1991); Kozbar et al., Immunology Today 4:72 (1983)), Cole et al., "Monoclonal Antibodies and Cancer Therapy" (Alan R. Liss, Inc. pp. 77-96 (1985)); Cabilly et al., U.S. Pat. No. 4,816,567; Winter, U.S. Pat. No. 5,225,539; Cabilly et al., European Patent No. 0,125,023; Boss et al., U.S. Pat. No. 4,816,397; Boss et al., European Patent No.0,120,694; Neuberger et al., WO 86/01533; Neuberger et al., European Patent No. 0,194,276; Winter, European Patent No. 0,239,400; Newman et al., BioTechnology 10:1455-1460 (1992); Ladner et al., U.S. Pat. No. 4,946,778; Bird et al., Science 242:423-426 (1988); Kamman et al., Nucl. Acids Res., 17:5404 (1989)); Sato et al., Cancer Research 53:851-856 (1993); Daugherty et al., Nucleic Acids Res. 19(9):2471-2476 (1991); Lewis and Crowe, Gene 101:297-302 (1991); Krebber et al., U.S. Pat. No. 5,514,548; and Hoogenboom et al., WO 93/06213; Jakobovits et al., Proc. Natl. Acad. Sci. USA 90:2551-2555 (1993); Jakobovits et al., Nature 362:255-258 (1993); Lonberg et al., U.S. Pat. No. 5,545,806; Surani et al., U.S. Pat. No. 5,545,807; Queen et al., European Patent No. 0,451,216; Boss et al., U.S. Pat. No. 4,816,397; Boss et al., European Patent No. 0,120,694; Neuberger et al., WO 86/01533; Padlan et al., European Patent Application No. 0,519,596; Ladner et al., U.S. Pat. No. 4,946,778; and Huston, U.S. Pat. No. 5,476,786.

"Upstream" Inhibitors of CASP1

In addition to inhibitors which directly affect expression of CASP1 gene and/or function of CASP1 protein and inhibitors which directly affect expression of NLRP3 gene and/or function of NLRP3 protein, inhibitors which are useful in the methods of the invention include inhibitors of NLRP3 inflammasome formation and inhibitors of NLRP3 inflammasome activity. Non-limiting examples of inhibitors of NLRP3 inflammasome formation and/or NLRP3 inflammasome activity useful in the methods of the invention include, e.g., small molecular weight compounds fitting in the ATP binding site of NLRP3 and nitric oxide (NO) donors (e.g., S-nitroso-N-acetylpenicillamine (SNAP)). See, e.g., Hernandez-Cuellar et al., J Immunol., 2012, 189(11):5113-5117. Other useful inhibitors include small molecular weight compounds specifically blocking HSP90, such as geldanamycin, or less toxic derivates, such as 17-AAG (17-(Allylamino)-17-demethoxygeldanamycin) or 17-DMAG (17-(Dimethylaminoethylamino)-17-demethoxygeldanamycin) and their pharmaceutically acceptable salts, have been successfully developed. These inhibitors are effective in the HSP90-dependent assembly of the NLRP3 inflammasome. See, e.g., U.S. Patent Appl. Pub. No. 2011/0262449. Other geldanamycin derivatives are known in the art such as compounds disclosed in U.S. Pat. No. 4,261,989, US 2004/0235813, WO 02/36574, WO 02/079167, WO 03/02671 and WO 2005/095347. Other inhibitors of HSP90 are also known in the art, such as compounds disclosed in WO 2006/095783, WO 2006/092202, WO 2006/090094, WO 2006/087077, WO 2006/084030, WO 2005/028434, WO 2004/072051, WO 2006/079789, US 2006-0167070, WO 2006/075095, US 2006-0148817, WO 2006/057396, WO 2006/055760, WO 02/069900, WO 2006/052795, WO 2006/050373, WO 2006/051808, WO 2006/039977, US 2006/0073151, EP 1 642 880, EP 1 631 267, EP 1 628 667, US 2006/0035837, WO 2006/008503, WO 2006/010595, WO 2006/010594, WO 2006/003384, WO 2005/115431, EP 1 620 090, WO 2005/061461, WO 2005/063222, US 2005/ 0049263, WO 2004/050087, WO 2004/024142, WO 2004/024141, WO 03/067262, WO 03/055860, WO 03/041643, WO 03/037860.

Methods for Administering Compositions Comprising CASP1 Inhibitors

The appropriate dosages of CASP1 inhibitors used in the methods of the invention will depend on the type of disease to be treated, the severity and course of the disease, previous therapy, the patient's clinical history and response to the inhibitor, and the discretion of the attending physician. A CASP1 inhibitor can be administered to the patient at one time or over a series of treatments. The progress of the therapy of the invention can be easily monitored by conventional techniques and assays.

The administration of CASP1 inhibitors according to the methods of the invention can be performed by any suitable route, including systemic administration as well as administration directly to the site of the disease (e.g., to primary tumor).

In certain embodiments, the CASP1 inhibitors are formulated in pharmaceutical compositions with a pharmaceutically acceptable carrier or excipient.

In a separate embodiment, the invention also provides pharmaceutical compositions comprising a CASP1 inhibitor, a glucocorticoid, and a pharmaceutically acceptable carrier or excipient.

The formulations used in the methods of the invention may conveniently be presented in unit dosage form and may be prepared by methods known in the art. The amount of active ingredients that can be combined with a carrier material to produce a single dosage form will vary depending upon the host being treated and the particular mode of administration. The amount of active ingredients that can be combined with a carrier material to produce a single dosage form will generally be that amount of the compound which produces a therapeutic effect.

In general, the formulations can be prepared with a liquid carrier, or a finely divided solid carrier, or both, and then, if necessary, shaping the product.

Formulations for oral administration may be in the form of capsules, cachets, pills, tablets, powders, granules, or as a solution or a suspension in an aqueous or non-aqueous liquid, or as anoil-in-water or water-in-oil liquid emulsion, and the like, each containing a predetermined amount of one or more active ingredients.

In solid dosage forms for oral administration (capsules, tablets, pills, dragees, powders, granules, and the like), one or more active ingredients can be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Suspensions, in addition to one or more active ingredients, can contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Compositions of the invention can be also administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject therapeutic agents may be mixed under sterile conditions with a pharmaceutically acceptable carrier, and with any preservatives, buffers, or propellants which may be required. The ointments, pastes, creams and gels may contain, in addition to a subject polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to one or more active ingredients, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more active ingredients in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms can be made by forming microencapsule matrices of one or more active ingredients in biodegradable polymers such as polylactide-polyglycolide. Depending on the ratio of active ingredient to polymer, and the nature of the particular polymer employed, the rate of antagonist release can be controlled. Examples of other biodegradable polymers include poly(orthoesters) and poly (anhydrides). Depot injectable formulations are also prepared by entrapping the antagonists in liposomes or microemulsions which are compatible with body tissue.

Formulations for intravaginal or rectal administration may be presented as a suppository, which may be prepared by mixing one or more active ingredients with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Diagnostic Methods of the Invention

In one embodiment, the invention provides a method for determining whether a cancer in a subject is likely to be resistant to a glucocorticoid treatment, said method comprising the steps of:

(d) determining the expression level of CASP1 gene and/or NLRP3 gene in cancer cells from the subject;

(e) comparing the expression level of each gene determined in step (a) with a corresponding control expression level for that gene, and (f) (i) identifying that the cancer in the subject is likely to be resistant to the glucocorticoid treatment when the expression level of CASP1 gene and/or NLRP3 gene in step (a) is increased by at least 1.5 fold as compared to the corresponding control expression level or (ii) identifying that the cancer in the subject is not likely to be resistant to the glucocorticoid treatment when the expression level of CASP1 gene and/or NLRP3 gene in step (a) is not increased or is increased by less than 1.5 fold as compared to the corresponding control expression level.

In one specific embodiment, the corresponding control expression level is the expression level of the same gene in similarly processed cancer cells of the same type which are sensitive to glucocorticoid treatment. In another specific embodiment, the corresponding control expression level is a predetermined standard.

For determination of CASP1 or NLRP3 expression levels, RNA can be extracted from the collected cancer cells or tumor samples and purified using a variety of standard procedures as described, for example, in *RNA Methodologies, A laboratory guide for isolation and characterization*, 2nd edition, 1998, Robert E. Farrell, Jr., Ed., Academic Press. In addition, various commercial products are available for RNA isolation.

The expression levels of CASP1 or NLRP3 can be determined using any of various techniques known in the art. Such methods include, without limitation, amplification-based assays such as RT-PCR (e.g., TAQMAN), hybridization-based assays such as DNA microarray analysis, flap-endonuclease-based assays (e.g., INVADER), and direct mRNA capture (QUANTIGENE or HYBRID CAPTURE (Digene)). See, for example, US 2010/0190173 for descriptions of representative methods that can be used to determine expression levels.

Methods of detecting and/or quantifying the level of CASP1 and/or NLRP3 gene transcripts (mRNA or cDNA made therefrom) using nucleic acid hybridization techniques are known to those of skill in the art. Non-limiting examples of useful hybridization techniques include Northern blotting, dot blotting, in situ hybridization, RNase protection, probing DNA microchip arrays, and the like.

In another embodiment, amplification-based assays are used to measure the expression level of CASP1 and/or NLRP3. In such assays, the CASP1 and/or NLRP3 nucleic acid sequences act as a template in an amplification reaction (e.g., PCR). In a quantitative amplification, the amount of amplification product will be proportional to the amount of template in the original sample. Comparison to appropriate controls provides a measure of the level of CASP1 and/or NLRP3 in the sample. Methods of quantitative amplification are well known to those of skill in the art. Detailed protocols for quantitative PCR are provided, e.g., in Innis et al. (1990) PCR Protocols, A Guide to Methods and Applications, Academic Press, Inc. N.Y.). The known nucleic acid sequences for CASP1 and/or NLRP3 enable one of skill to routinely select primers to amplify any portion of these genes. In one embodiment, a TaqMan based assay is used to quantify the CASP1 and/or NLRP3 expression. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, literature provided by Perkin-Elmer, e.g., www2.perkin-elmer.com). Other suitable amplification methods include, but are not limited to, ligase chain reaction (LCR) (see, Wu and Wallace (1989) Genomics 4:560, Landegren et al. (1988) Science 241: 1077, and Barringer et al. (1990) Gene 89:117), transcription amplification (Kwok et al. (1989) Proc. Natl. Acad. Sci. USA 86: 1173), self-sustained sequence replication (Guatelli et al. (1990) Proc. Nat. Acad. Sci. USA 87: 1874), dot PCR, and linker adapter PCR, etc.

In a separate embodiment, the expression level of CASP1 gene and/or NLRP3 gene is determined by determining the level of CASP1 and/or NLRP3 protein (using e.g., antibodies).

In a separate embodiment, the invention provides a method for determining whether a cancer in a subject is likely to be resistant to a glucocorticoid treatment, said method comprising the steps of:
(d) determining the methylation level of CASP1 gene promoter and/or NLRP3 gene promoter in cancer cells from the subject;
(e) comparing the methylation level of each gene promoter determined in step (a) with a corresponding control methylation level for that gene promoter, and
(f) (i) identifying that the cancer in the subject is likely to be resistant to glucocorticoid treatment when the methylation level of CASP1 gene promoter and/or NLRP3 gene promoter in step (a) is decreased by at least 1.5 fold as compared to the corresponding control methylation level or (ii) identifying that the cancer in the subject is not likely to be resistant to glucocorticoid treatment when the methylation level of CASP1 gene promoter and/or NLRP3 gene promoter in step (a) is not increased or is increased by less than 1.5 fold as compared to the corresponding control methylation level.

In one specific embodiment, the CASP1 gene promoter comprises the sequence (SEQ ID NO: 3)
GTCGGGGAAGGTTTTGAGAAAGAAGGGTCCCTGGACAAGAACCTTGTCAT

TTTCTGAGTGGCCGGTACCGAAAAGAGAGGAGGGAAGAACACACTGACTT

TGACTTTCATACGAAGCGGAAG

In one specific embodiment, the NLRP3 gene promoter comprises the sequence (SEQ ID NO: 4)
CTCCTTTGACTTCAACTCCTTATCACTTCTCAAACAGGTTACAGTATCGG

GGCATTAGTTGCCCTGTTTTTAAAAGAACGACTACCCAGTTCTACCGTAG

CACTTCACCAACAAGTGGCATT

In one specific embodiment, the corresponding control methylation level is the methylation level of the same gene promoter in similarly processed cancer cells of the same type which are sensitive to glucocorticoid treatment. In one specific embodiment, the corresponding control methylation level is a predetermined standard.

Promoter methylation of CASP1 gene and/or NLRP3 gene can be determined by any method known in the art. One example of a useful method is Southern blot analysis after cleavage with methylation-sensitive restriction endonucleases or PCR across the restriction sites of such enzymes. Any restriction endonuclease that includes CG as part of its recognition site and that is inhibited when the C is methylated, can be utilized for this analysis. Methylation sensitive restriction endonucleases include, for example, AciI, BsiEI, BssHII, BstUI, Eag I, FauI, HaeII, HpaI, HpaII, MspI, NarI, NotI, SacII, and SmaI. These enzymes may be used alone or in combination.

Another useful method for determining promoter methylation of CASP1 gene and/or NLRP3 gene is bisulfite DNA sequencing which is based on sodium bisulfite-induced modification of genomic DNA under conditions whereby unmethylated cytosine is converted to uracil. The bisulfite-modified sequence is then amplified by PCR with two sets of strand-specific primers to yield a pair of fragments, one from each strand, in which all uracil and thymine residues are amplified as thymine and only 5-methylcytosine residues are amplified as cytosine. The PCR products can be sequenced directly or can be cloned and sequenced to provide methylation maps of single DNA molecules (see, e.g., Frommer, et al., Proc. Natl. Acad. Sci. 89: 1827-1831, 1992). PCR can be either CD-PCR with primer pairs located outside the CpG sites or MS-PCR with primers specific for methylated (M primer) versus unmethylated (U primer) DNA (Herman et al., 1996). The difference between CD-PCR and MS-PCR is the location of primer site. In CD-PCR, primers are designed from the regions outside the CpG islands and the methylation status of the CpG islands is investigated from cloning and sequencing of the PCR product. In MS-PCR, primers are chosen from the CpG sites to discriminate between methylated and unmethylated alleles following bisulfate treatment and thus the methylation status of the CpG islands is assessed directly from the PCR product. The PCR product is expected only in samples where methylated DNA is mixed with the M primer and unmethylated DNA is mixed with U primer.

Other useful methods for determining promoter methylation of CASP1 gene and/or NLRP3 gene include Restriction Landmark Genome Scanning (RLGS) and Methylation-Sensitive Representational Difference Analysis (MS-RDA). In RLGS methylation changes are visualized as a dense cluster of "spots" on 2-dimensional gels. MS-RDA is a PCR-based technique that is biased toward short DNA fragments and against GC-rich sequences. Novel array-based hybridization methods have also been developed. Another useful method is Methylation Subtraction Analysis (MSA) which relies on the enzymatic fractionation of the human genome into its methylated and unmethylated compartments.

In the diagnostic methods of the invention, after determining the expression levels or promoter methylation levels of CASP1 and/or NLRP3, the patient's cancer can be classified as being likely or unlikely to be resistant to glucocorticoid therapy. The classification may be determined computationally based upon known methods in the art. The result of the computation may be displayed on a computer screen or presented in a tangible form, for example, as a probability (e.g., from 0 to 100%) of the patient. The report will aid a physician in determining further treatment of the patient. For example, in certain embodiments, where the patient's expression levels or promoter methylation levels of CASP1 and/or NLRP3 will be prognostic of resistance to glucocorticoid therapy, the patient will be subsequently treated with either (i) a combination of a CASP1 inhibitor and a glucocorticoid, or (ii) with increased (e.g., at least 1.5 fold more than typical) doses of a glucocorticoid, or (iii) with a non-glucocorticoid chemotherapeutic and/or radiation. In certain embodiments, where the patient's expression levels or promoter methylation levels of CASP1 and/or NLRP3 will be prognostic of lack of resistance to glucocorticoid therapy, the patient will be subsequently treated with a glucocorticoid.

In conjunction with the diagnostic methods of the invention, provided herein are various kits for diagnosing likelihood of cancer resistance to glucocorticoid treatment. In one embodiment, such kit comprises one or more pairs of oligonucleotides directed toward CASP1 and/or NLRP3, wherein said pairs of oligonucleotides can be used to determine the expression levels of CASP1 gene and/or NLRP3 gene. The oligonucleotides may be designed to detect expression levels in accordance with any assay format, including but not limited to those described herein. Such kit can further comprise a detection means and/or an amplification means and/or one or more pairs of control oligonucleotides. In another embodiment, a kit for diagnosing likelihood of cancer resistance to glucocorticoid treatment comprises antibodies directed toward CASP1 protein and/or NLRP3 protein, wherein said antibodies can be used to determine the expression levels of CASP1 and/or NLRP3 protein. Such kit can further comprise a detection means and/or one or more control antibodies.

In yet another embodiment, a kit for diagnosing likelihood of cancer resistance to glucocorticoid treatment comprises means for detecting promoter methylation of CASP1 gene and/or NLRP3 gene. In one specific embodiment, such kit includes sodium bisulfite, hydroquinone and standard components for DNA sequence determination either via Sanger sequencing, including location specific oligonucleotide primers or via next generation sequencing, or via solution bead based or solid substrate hybridization methods.

Any of the kits of the invention can optionally further comprise instructions for use.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Materials and Methods

Patient Samples

Written informed assent or consent was obtained from patients or their parents/guardians (as appropriate). The research and use of these samples were approved by the institutional review board at the host institute.

Gene Expression Analyses

Total RNA was extracted with TriReagent (Molecular Research Center, Inc., Cincinnati, OH) from cryopreserved mononuclear cell suspensions from patient bone marrow aspirates obtained at diagnosis. All gene expression microarrays were performed by the St. Jude Children's Research Hospital, Hartwell Center for Bioinformatics & Biotechnology. High-quality RNA was hybridized to the HG-U133A (GPL96) or HG-U133 Plus 2.0 (GPL570) oligonucleotide microarrays in accordance with the manufacturer's protocol (Affymetrix, Santa Clara, Calif.). These microarrays contain 22,283 or 54,675 gene probe sets, representing approximately 18,400 or 47,400 human transcripts, respectively. Gene expression data were MASS (Hubbell et al., 2002) processed using the affy (Gautier et al., 2004) Bioconductor (Gentleman et al., 2004) R-project package or using Affymetrix Microarray Suite version 5.0 (Cheok et al., 2003; Yeoh et al., 2002) as previously described (Holleman et al., 2004).

DNA Methylation Analyses

DNA was isolated at the time of diagnosis from lymphoblasts from patient bone marrow aspirates. Genome-wide DNA methylation status was determined using either an Infinium HumanMethylation27 BeadChip Kit or Infinium HumanMethylation450 BeadChip Kit in accordance with the manufacturer's protocol (Illumina, San Diego, Calif.). HumanMethylation27 BeadChips were performed at either Emory Integrated Genomics Core (EIGC) or Wellcome Trust Centre for Human Genetics Genomics Lab, Oxford, UK. HumanMethylation450 BeadChip experiments were performed at the Heflin Center for Genomic Science at the University of Alabama at Birmingham. DNA methylation status was classified as low if less than or equal to 0.25 and high if greater than 0.25.

Statistical Analyses

Analyses were performed using R software (http://www.r-project.org) unless otherwise specified. Exact Wilcoxon Mann-Whitney Rank Sum tests were used for analyses of differential gene expression and differential DNA methylation and Stouffer's Z-score method was used for meta-analysis (Stouffer et al., 1949). K-means clustering analysis with a k=2 was used for DNA methylation data and either untransformed or log-transformed gene expression data, with Fisher's exact test for determining clustering significance. Fisher's exact test was used to assess the significance of enrichment of known glucocorticoid response elements.

CASP1 Enzymatic Assays

Recombinant human CASP1 (100-200 U, where U=1 pmol/min at 30° C., 200 µM YVAD-pNA (SEQ ID NO: 21)) from a CASP1 assay kit for drug discovery (Enzo Life Sciences, Farmingdale, N.Y., catalog number BML-AK701-0001) was incubated at 30° C. with wild-type or mutated GR in the presence (10 µM unless otherwise indicated) or absence of inhibitors, (Ac-YVAD-CHO (SEQ ID NO: 18), Enzo Life Sciences, Farmingdale, N.Y., catalog number BML-P403-9090), VX765, VRT-043198). Substrates for enzyme assays were prepared in CASP1 assay buffer (Enzo Life Sciences, Farmingdale, N.Y. catalog number KI-111) consisting of 50 mM HEPES, pH7.4, 100 mM NaCl, 0.1% CHAPS, 10 mM DTT, 1 mM EDTA and 10% glycerol.

Site-Directed Mutagenesis

Site-directed mutagenesis was performed on NR3C1 using a QuikChange Site-Directed Mutagenesis Kit (Stratagene, La Jolla, Calif.). Mutagenesis of the LLID motif (SEQ ID NO: 20) was performed in 4 sequential mutagenesis reactions from Myc-DDK tagged NR3C1 (Origene, Rockville, Md., catalog #RC220189). The following mutagenesis primers were used:

```
MutF1-NR3C1:
                                        (SEQ ID NO: 5)
CCTTGGAGATCAGACCTGTTGATAGCTGAAAACTGTTTGCTTTC;

MutR1-NR3C1:
                                        (SEQ ID NO: 6)
GAAAGCAAACAGTTTTCAGCTATCAACAGGTCTGATCTCCAAGG;

MutF2-NR3C1:
                                        (SEQ ID NO: 7)
CCTTGGAGATCAGACCTGTTGGCAGCTGAAAACTGTTTGCTTTC;

MutR2-NR3C1:
                                        (SEQ ID NO: 8)
GAAAGCAAACAGTTTTCAGCTGCCAACAGGTCTGATCTCCAAGG;

MutF3-NR3C1:
                                        (SEQ ID NO: 9)
CCTTGGAGATCAGACCTGGCGGCAGCTGAAAACTGTTTGCTTTC;

MutR3-NR3C1:
                                        (SEQ ID NO: 10)
GAAAGCAAACAGTTTTCAGCTGCCGCCAGGTCTGATCTCCAAGG;

MutF4-NR3C1:
                                        (SEQ ID NO: 11)
CCTTGGAGATCAGACGCGGCGGCAGCTGAAAACTGTTTGCTTTC;

MutR4-NR3C1:
                                        (SEQ ID NO: 12)
GAAAGCAAACAGTTTTCAGCTGCCGCCGCGTCTGATCTCCAAGG.
```

Successful mutagenesis was confirmed by Sanger sequencing.

Ex Vivo Drug Sensitivity Assays

Leukemia cells were isolated at diagnosis from patient bone marrow aspirates. If the leukemia cell percentage from diagnostic bone marrow samples was less than ninety percent, magnetic activated cell sorting (Miltenyl Biotec, Auburn, Calif.) was performed to further enrich for leukemia cells. If red cell contamination was greater than thirty percent, red blood cell lysis was performed. Cells were centrifuged at 300 g for five minutes and resuspended at a concentration of two million cells per milliliter. Eighty microliters of this leukemia cell suspension was then plated into each experimental well of round-bottom 96-well plates. Twenty microliters of decreasing concentrations of prednisolone were added and the plates were incubated for ninety-six hours in a humidified incubator containing 5% $CO_2$ at 37° C. For the final six hours, ten microliters of 5 milligram per milliliter MTT (3-4,5-dimethylthiazol-2,5-diphenyl tetrazolium bromide) was added to each experimental well. Drug resistance assays in cell lines were performed using between 0.25 and 2.5 million cells per milliliter. Assays were developed and performed as for patient sample assays. LC50 values were determined as previously described (Holleman et al., 2004). Glucocorticoid resistant ALL was defined as having an LC50 greater than or equal to 64 µM, whereas glucocorticoid sensitive cases were defined as having an LC50 less than 0.1 µM. Patients classified as sensitive to prednisolone (LC50<0.1 µM) had a significantly better treatment outcome, with a 5 year event free survival of 95.6% compared to 82.7% for other patients tested for prednisolone sensitivity on the Total XV protocol (p=0.01 log rank test).

CASP1 Enforced Expression

Full-length CASP1 (Origene, Rockville, Md., catalog #RC218364; GenBank Accession No. NM_033292) was subcloned into a lentiviral backbone (System Biosciences, Mountain View, Calif., catalog number CD527A-1), in frame with a T2A linked puromycin resistance gene. Lentivirus was produced in 293T cells and the Nalm6 leukemia cell line was transduced. 72 hours post transduction, cells were selected with 2.5 micrograms per milliliter puromycin. Where indicated cells were treated with 10 µg/mL LPS (InvivoGen, San Diego, Calif.) followed 2 hours later by 5 mM ATP (Roche, Pleasanton, Calif.).

Expression of Mutant GR Without CASP1 Cleavage Sites

Doubly mutated GR (LLID (SEQ ID NO: 20) and IKQE (SEQ ID NO: 22); SEQ ID NO: 17) was subcloned into the pLX304 (Yang et al., 2011) lentiviral backbone (Addgene plasmid 25890; Sigma-Aldrich, St. Louis, Mo.). Lentivirus was produced in 293T cells and NALM-6 leukemia cell lines with CASP1 overexpression and shRNA directed towards CASP1 (SEQ ID NO: 14) or a non-targeting shRNA (SEQ ID NO: 13) were transduced. Seventy-two hours post transduction, cells were selected with blasticidin.

Expression of GFP and CrmA

Green fluorescent protein (Addgene plasmid 15301) (Boehm et al., 2007) or CrmA (Addgene plasmid 11832; SEQ ID NO: 15) (Muzio et al., 1997) was subcloned into the pLX304 (Yang et al., 2011) lentiviral backbone (Addgene plasmid 25890; Sigma-Aldrich, St. Louis, Mo.). Lentivirus was produced in 293T cells and NALM-6 leukemia cell lines with CASP1 overexpression and shRNA directed towards CASP1 (SEQ ID NO: 14) or a non-targeting shRNA (SEQ ID NO: 13) were transduced. Seventy-two hours post transduction, cells were selected with blasticidin.

Western Blotting

Cells were pelleted by centrifugation, washed once with PBS and lysed with RIPA buffer or caspase-1 assay buffer (Enzo Life Sciences, Farmingdale, N.Y. catalog number KI-111), equal amounts of proteins (1-20 µg) separated by 4-12% Novex Bis-Tris gels (Life Technologies, Grand Island, N.Y.), and then transblotted to PVDF membranes (Life Technologies, Grand Island, N.Y.). Anti-GR (1:1000-1:10,000, BD catalog number 611227), anti-DDK tubulin (1:1000, Origene catalog number TA50011), anti-Bim (1:1000, Cell Signalling catalog number 2819) or anti- Tubulin (1:1000, Santa Cruz, sc-8035) were used as primary antibodies followed by appropriate secondary HRP-conjugated IgG (1:1000, Dako) and immunocomplexes were visualized by chemiluminescence.

Glucocorticoid Induced Changes in Gene Expression

Nalm6 cells transduced with either empty vector (control) or CASP1 containing lentiviral particles, were treated with or without 0.3 mM prednisolone for 24 hours. RNA was extracted and hybridized to Affymetrix PrimeView oligonucleotide microarrays and RMA processed.

To be included as a gene that was transactivated by glucocorticoids, the level of mRNA expression had to increase in control cells by at least 1.5-fold in all four replicate experiments, by at least 2-fold in three of four replicates and by at least 3-fold in one experiment. Similarly, to be included as a gene that was transrepressed by glucocorticoids, the level of mRNA expression had to decrease by at least 33% in all four experiments, by at least 50% in three of four experiments and by at least 66% in one or more of the four replicate experiments.

Expression of CASP1 and NLRP3 in Leukemia Cells at the Time of Disease Relapse Versus at Diagnosis Gene expression was assessed at diagnosis and relapse as previously described (29). This dataset (GEO accession: GSE28460) was MASS (22) processed using the affy (23) Bioconductor (24) R-project package and then quantile normalized (30). A paired t-test was used for comparison of the matching diagnosis and relapse data.

Results

Higher Expression of CASP1 and NLRP3 in Glucocorticoid Resistant Leukemia

The de novo sensitivity of primary leukemia cells to prednisolone varied widely among patients in each of the three independent cohorts of newly diagnosed patients with ALL (FIGS. 1A-C). The present inventors found that CASP1 and NLRP3, both members of the NLRP3 inflammasome pathway, were expressed at a significantly higher level in glucocorticoid resistant primary ALL cells isolated from all three cohorts of patients (FIGS. 1D-F), with mean expression in resistant leukemia 1.6-fold higher than in sensitive leukemia cells (Stouffer's meta-analysis of exact Wilcoxon Mann-Whitney rank sum test $p=9.5\times10^{-7}$). Similarly, the expression of NLRP3 was significantly higher (by 2.4-fold) in prednisolone-resistant leukemia cells in all three independent cohorts of patients (Stouffer's meta-analysis of exact Wilcoxon Mann-Whitney rank sum test $p=7.1\times10^{-7}$; FIGS. 1G-I).

Figure 2B:
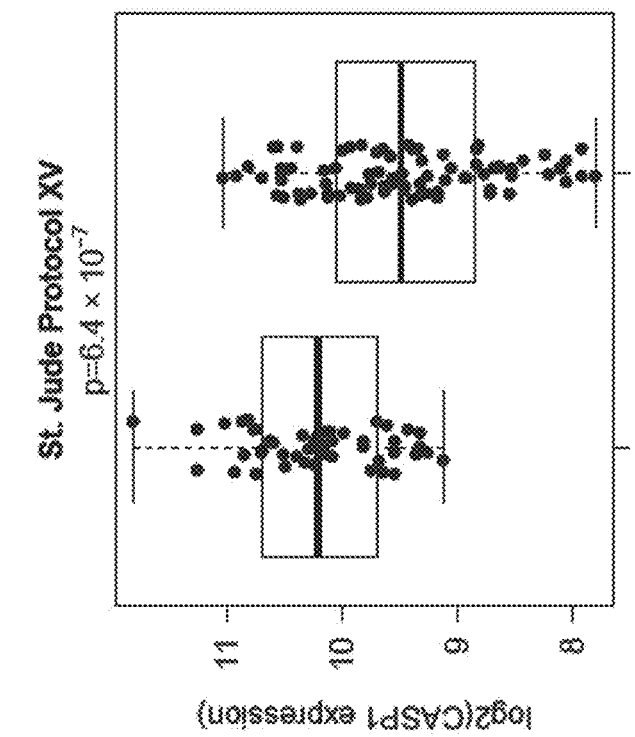
Figure 2C:
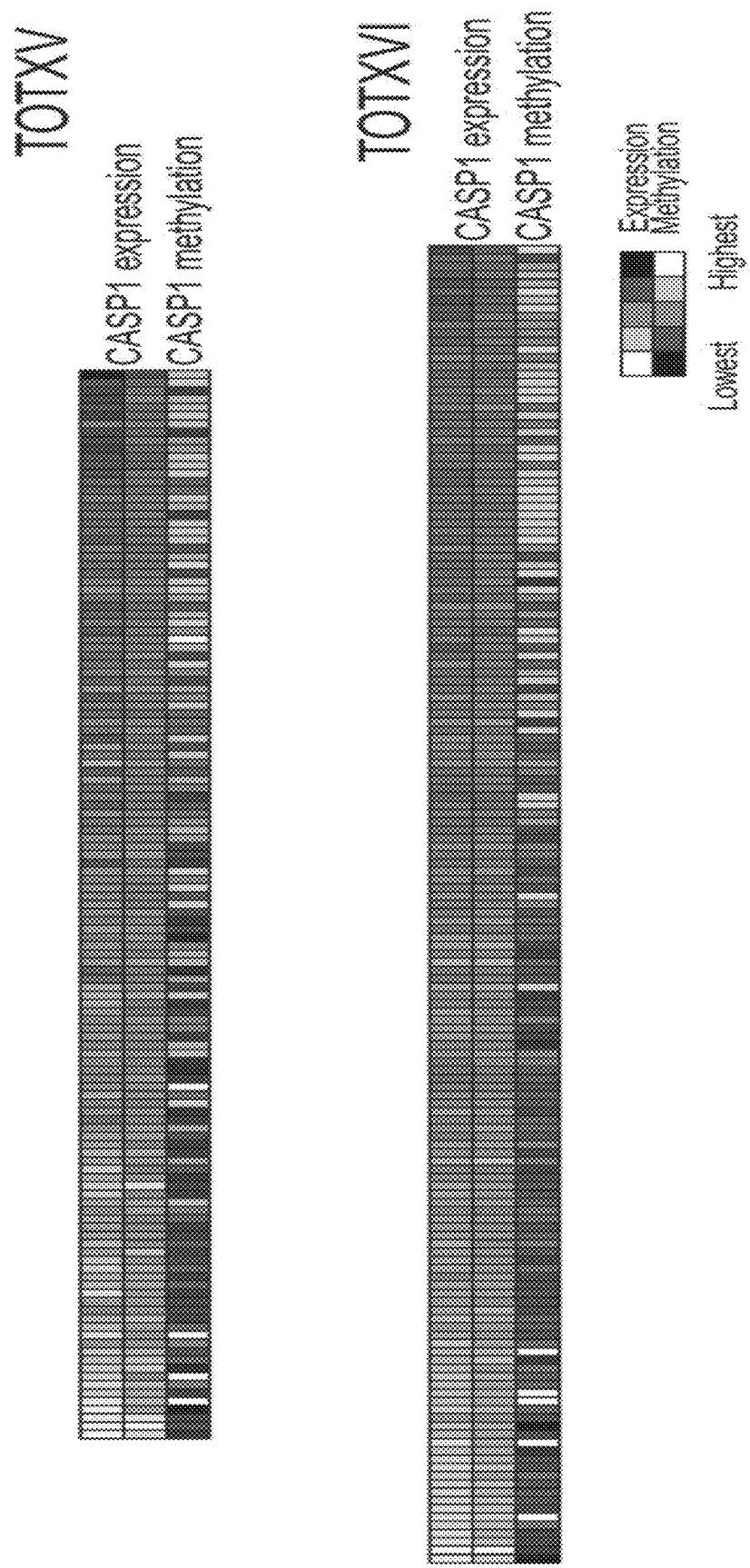
Figure 2F:
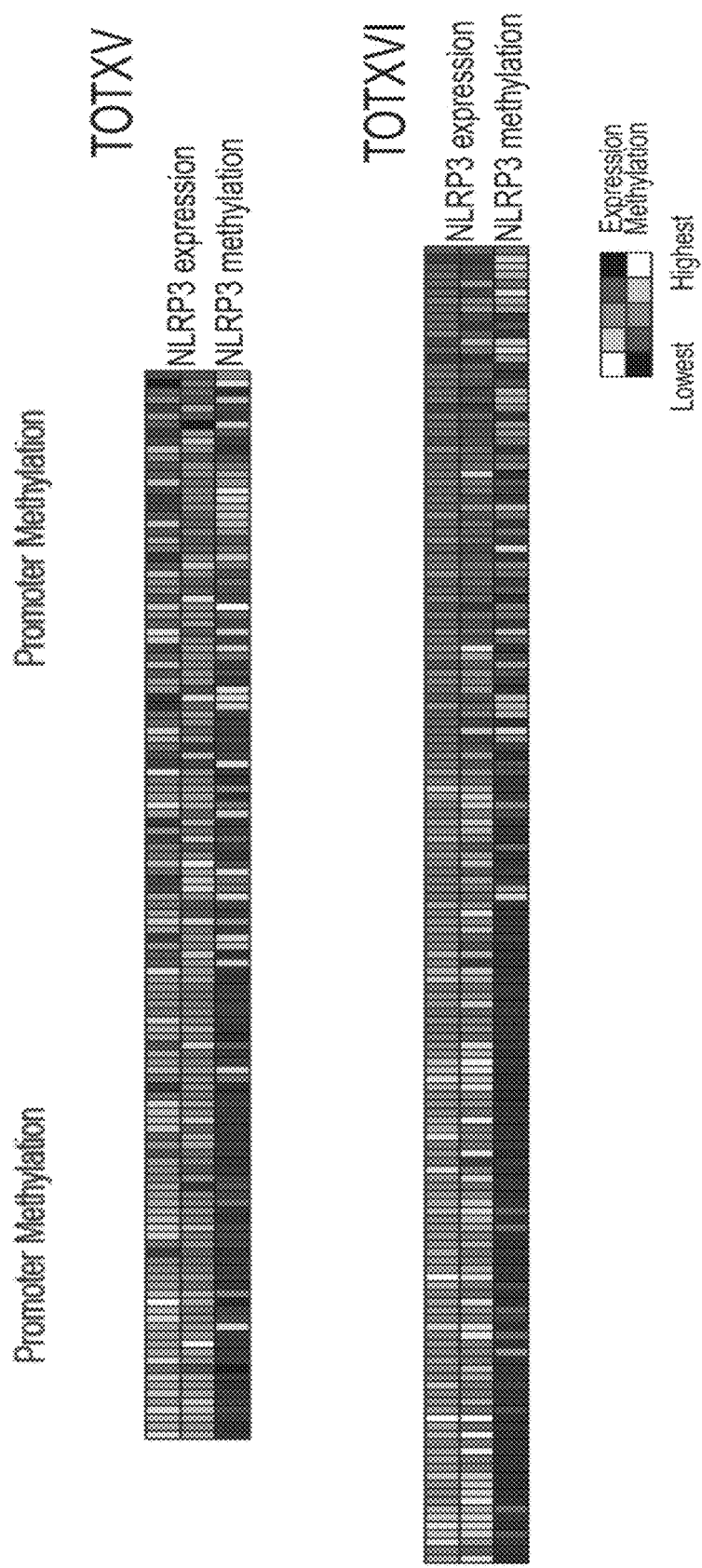
Figure 2G:
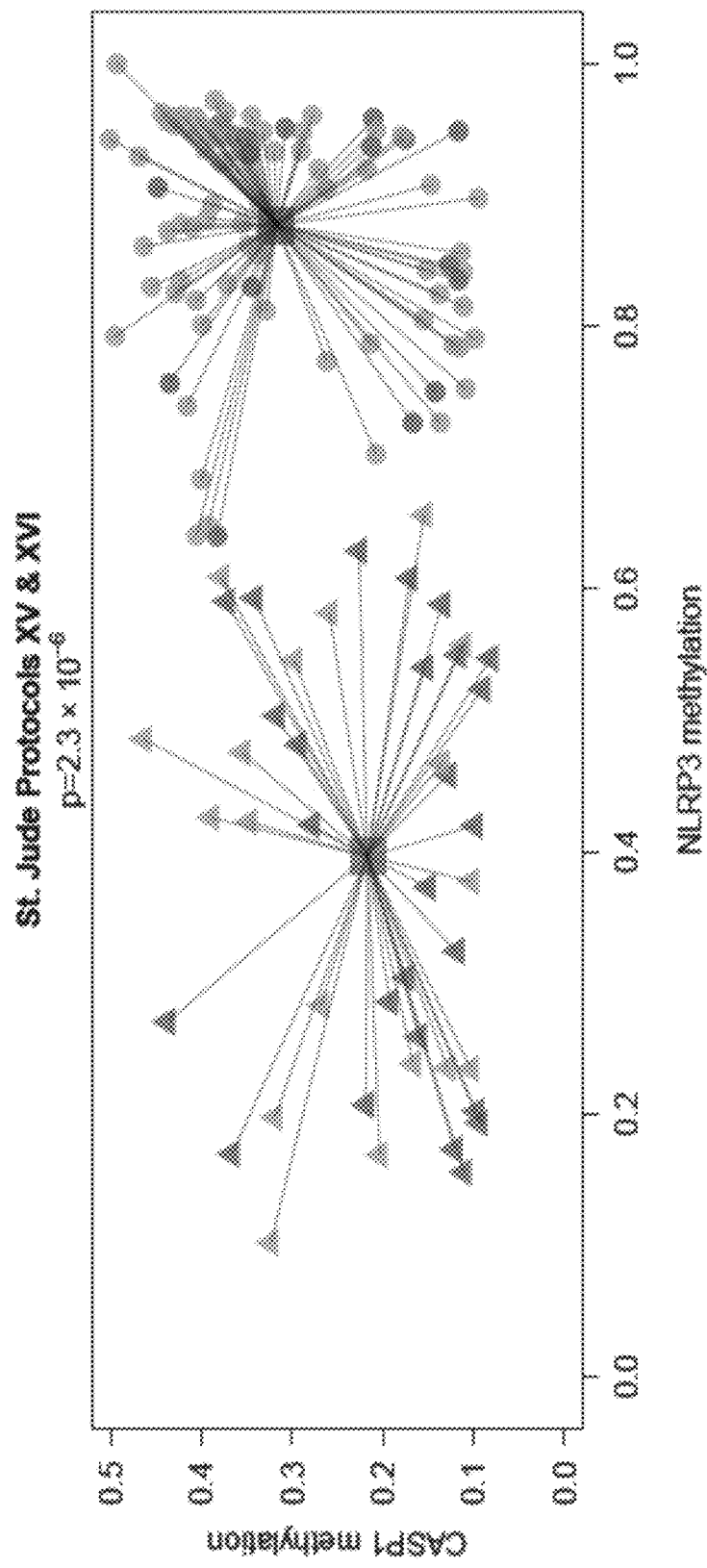

Lower Methylation of the CASP1 and NLRP3 Promoters is Associated with Higher CASP1 and NLRP3 Expression in Leukemia Cells To determine whether epigenetic mechanisms influence CASP1 and NLRP3 expression in leukemia cells, the relationship between CASP1 and NLRP3 mRNA expression and methylation of their promoter regions in leukemia cells was assessed. This revealed a highly significant relationship between the level of methylation of the CASP1 promoter and CASP1 mRNA expression in ALL cells (Stouffer's meta-analysis of exact Wilcoxon Mann-Whitney rank sum test $p=1.2\times10^{-17}$; FIGS. 2A-C). In a subset of patients where matching germline DNA methylation was analyzed (n=55), CASP1 promoter methylation did not differ significantly (Paired t-test p=0.495) in germline DNA and leukemia cell DNA, although 10 patients had significantly lower CASP1 promoter methylation in their ALL cells than their normal leukocytes, and the majority of these cases were glucocorticoid resistant (n=7, 70%) suggesting CASP1 demethylation in glucocorticoid resistant ALL cells. Methylation of the promoter region of NLRP3 was significantly greater in leukemia cell DNA than in germline DNA (Paired t-test $p=8.8\times10^{-11}$), and heterogeneity in leukemia cell methylation was significantly related to NLRP3 leukemia cell expression (Stouffer's meta-analysis of exact Wilcoxon Mann-Whitney rank sum test $p=5.5\times10^{-5}$; FIGS. 2D-F). Categorization of patients using k-means clustering of NLRP3 methylation and CASP1 methylation levels significantly distinguished prednisolone-sensitive (green symbols) from prednisolone-resistant (red symbols) leukemia cells (Fisher's Exact test for count data $p=2.3\times10^{-6}$; FIG. 2G). These results suggest that demethylation of CASP1 and NLRP3 in ALL cells leads to higher expression of these genes in glucocorticoid resistant ALL cells.

CASP1 Cleaves the Glucocorticoid Receptor

Figure 3A:
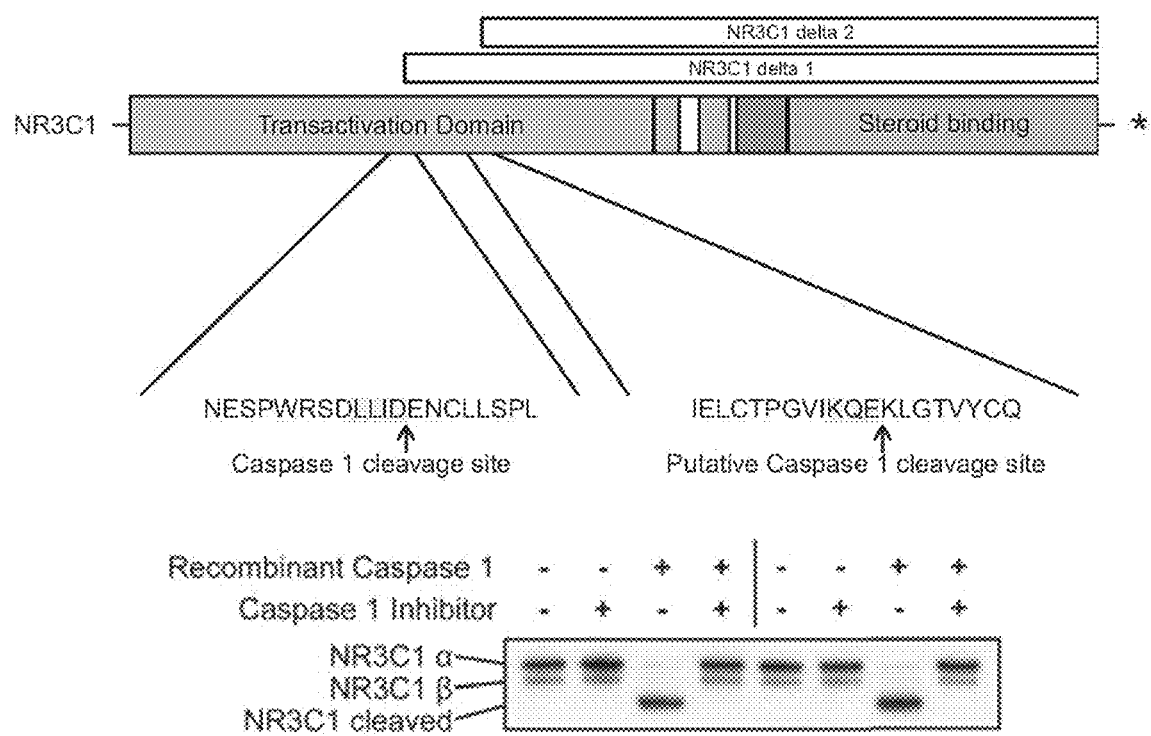
FIGS. 3A-E show that CASP1 cleaves the glucocorticoid receptor and increases resistance to glucocorticoids with an overarching schematic presented in panel D. Bioinformatic analysis of the glucocorticoid receptor (panel A, top) revealed a putative CASP1 cleavage site (LLID) (SEQ ID NO: 20) in the glucocorticoid receptor (NR3C1) transactivation domain that is similar to a previously reported CASP1 cleavage site in the androgen receptor, a close structural and functional homolog to the glucocorticoid receptor. Enzymatic assays revealed that recombinant CASP1 cleaves the GR and that this cleavage was inhibited by a CASP1 tetrapeptide inhibitor (panel A, bottom). Site directed mutagenesis of NR3C1 at the putative cleavage site (LLID motif) (SEQ ID NO: 20) blocked CASP1 cleavage at this location and revealed a secondary CASP1 cleavage site more proximal to the carboxy terminus of the protein, as evidenced by a smaller enzymatic product (panel B). Further inhibition studies showed that small molecule inhibitors VX-765 and VRT-043198 (panel C) can also inhibit CASP1 cleavage of NR3C1, with VRT-043198 having higher inhibitory activity. Enforced expression of CASP1 in a human leukemia cell line increased resistance to prednisolone and dexamethasone after activation of the NLRP3 inflammasome (by the addition of LPS and ATP). Nalm6 cells were transduced with a lentivirus containing full length CASP1 and puromycin N-acetyl-transferase or puromycin N-acetyl-transferase alone (Control). Cells were puromycin selected and then their sensitivity to prednisolone and dexamethasone (panel E) was measured using the MTT assay, in the presence(+) and absence(−) of inflammasome activation (LPS/ATP). The inset in panel E is a western blot depicting the lower GR levels in cells over expressing CASP1 (24 hours after activation of CASP1).
Figure 3B:
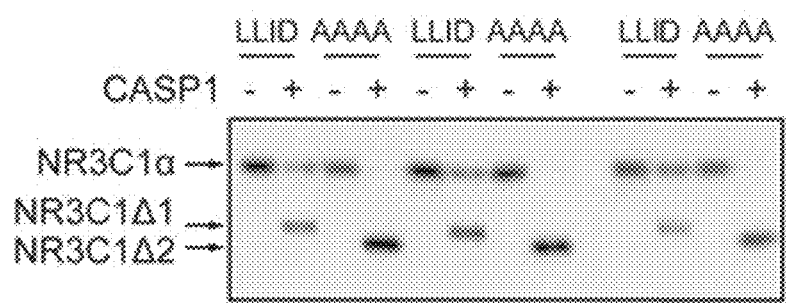
Figure 3C:
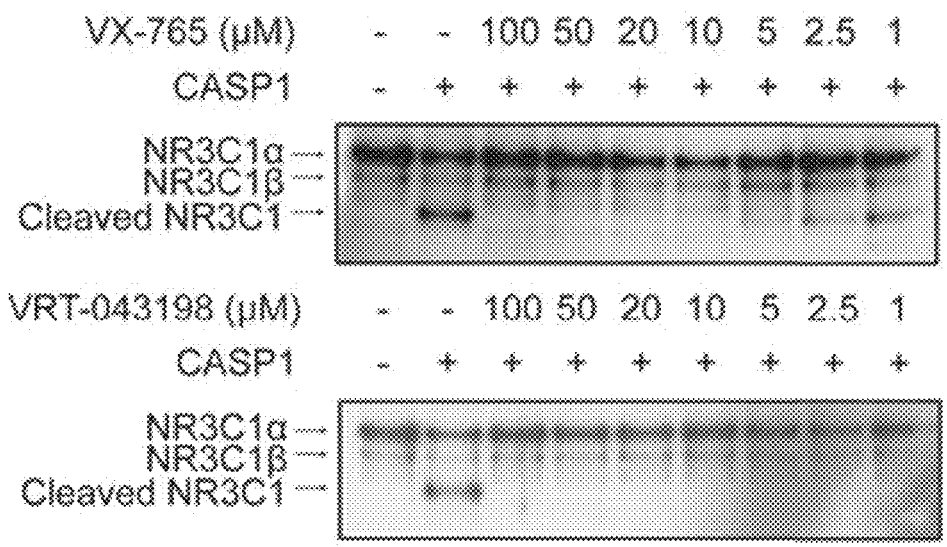
Figure 3D:
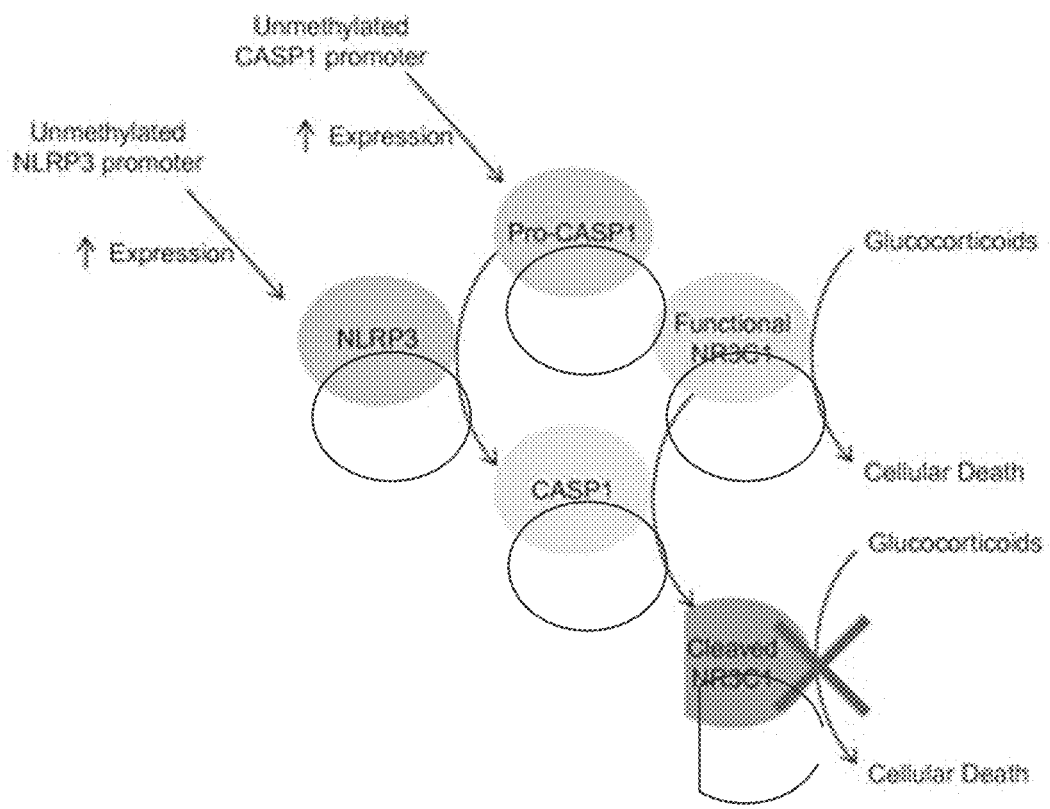

Based on a prior report of CASP1 cleavage of the androgen receptor (Wellington et al., 1998), the structural similarity between the androgen receptor and the glucocorticoid receptor, and the present identification of a putative CASP1 cleavage site (LLID) (SEQ ID NO: 20) in the transactivation domain of NR3C1 (FIG. 3A, upper panel), enzymatic assays were performed that revealed glucocorticoid receptor (NR3C1) cleavage by recombinant CASP1 (FIG. 3A, lower panel). Site-directed mutagenesis of the LLID motif (SEQ ID NO: 20) ablated cleavage of the glucocorticoid receptor at this location (FIG. 3B) and revealed a secondary CASP1 cleavage site in the GR (FIG. 3A, top). CASP1-induced cleavage of the glucocorticoid receptor was inhibited by both tetrapeptide inhibitors (FIG. 3A, lower panel) and small molecule inhibitors (VX765 and VRT043198) of CASP1 (Boxer et al., 2010) (FIG. 3C).

Figure 3E:
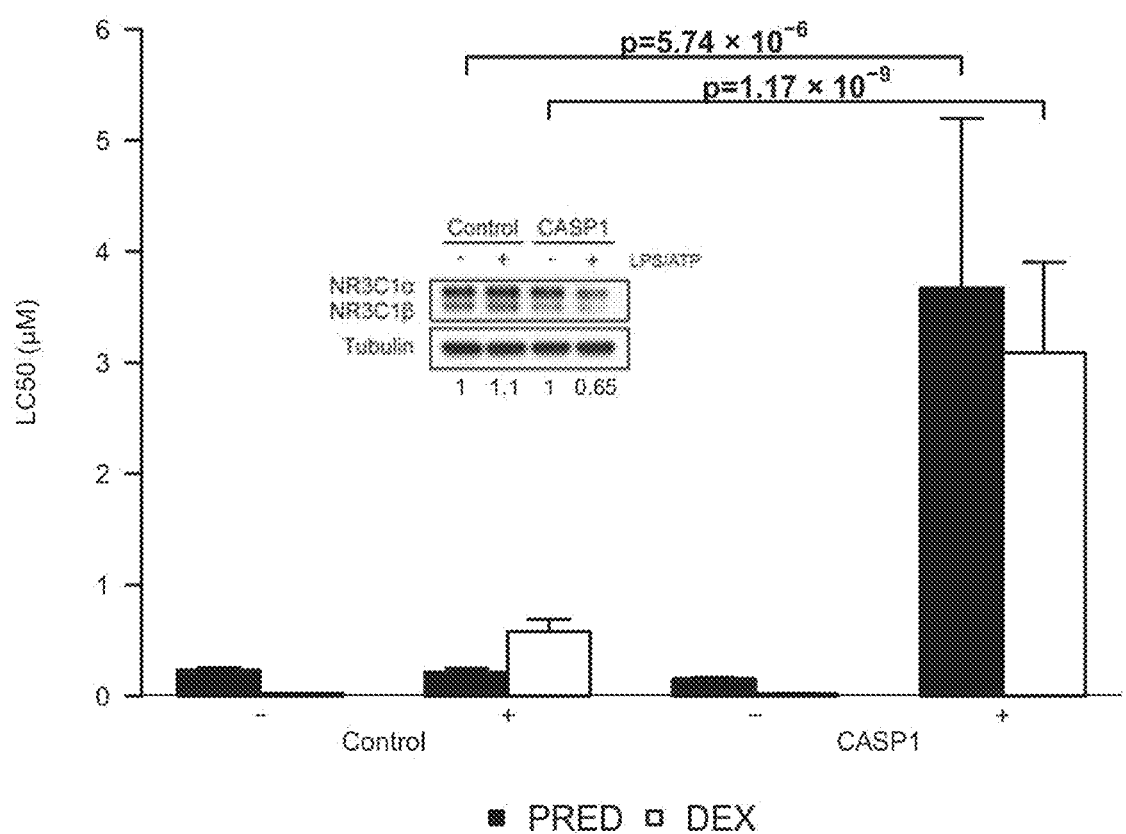

Full-length CASP1 was expressed in a human leukemia cell line (Nalm6) to determine whether CASP1 over-expression increases resistance to glucocorticoids. Under standard conditions for activation of the NLRP3 inflammasome and CASP1 (Ogura et al., 2006), cells transduced with empty vector control virus showed no difference in their sensitivity to prednisolone, whereas cells transduced with CASP1-containing virus showed markedly higher LC50 for prednisolone and dexamethasone (FIG. 3E). On average, CASP1 over-expression increased resistance to prednisolone by 16.9-fold (Student's t-test $p=5.7\times10^{-6}$) and dexamethasone by 5.3-fold (Student's t-test $p=1.2\times10^{-9}$), with a 35% reduction in GR levels by 24 hours.

CASP1 Blunts Glucocorticoid-Induced Transcriptional Response

Figure 4A:
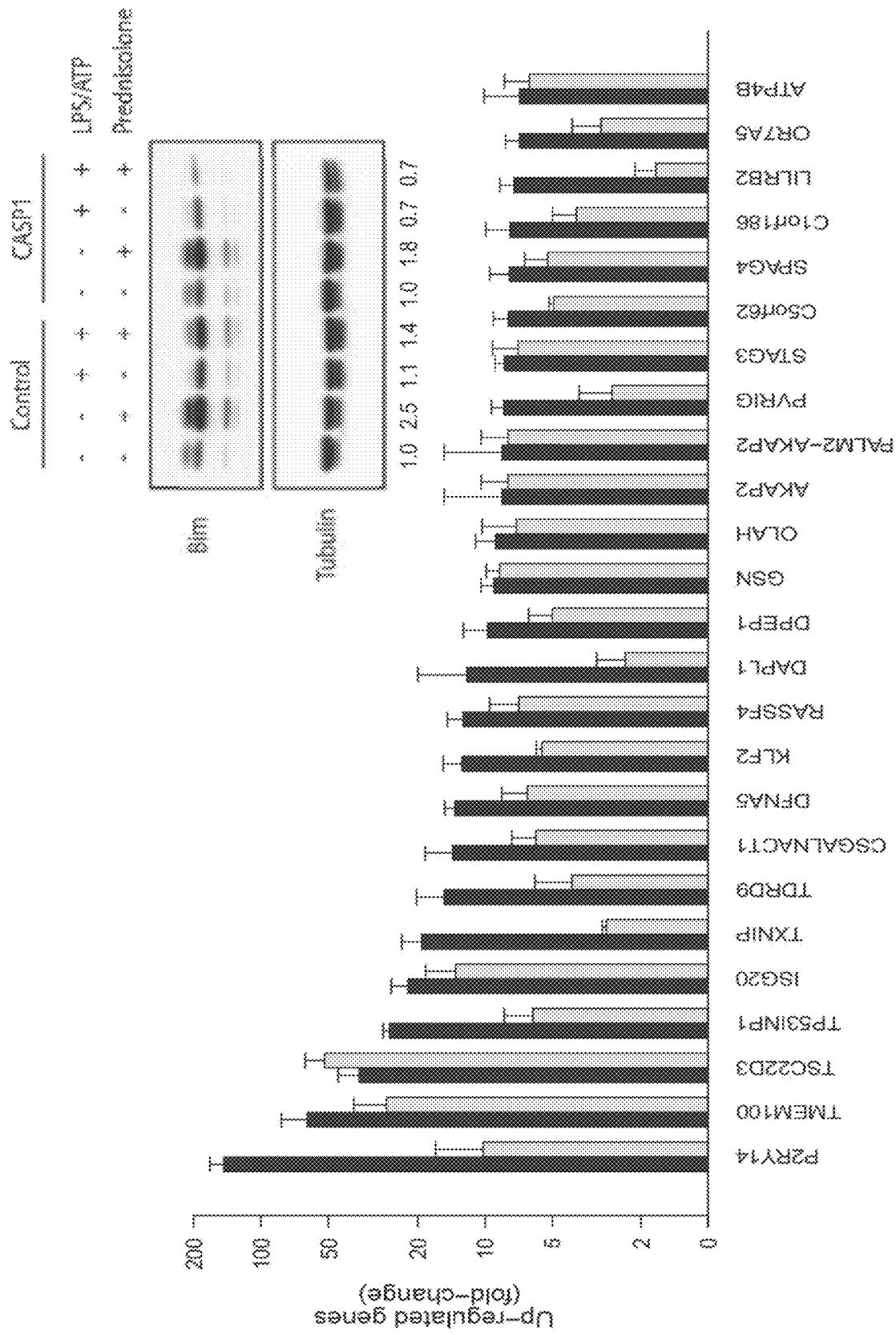
FIGS. 4A-B show that transcriptional modulation induced by glucocorticoids is blunted by CASP1. Cells expressing CASP1 or the empty vector (control cells) were treated with or without prednisolone to determine if CASP1 expression and activation alters transcriptional activation or repression of glucocorticoid response genes. Genome-wide gene expression was measured (panels A and B) and fold-differences in the expression of individual genes (with or without prednisolone treatment) were compared between control cells treated with prednisolone compared to the same cells not treated with prednisolone or in cells with enforced expression and activation of CASP1 treated with prednisolone or not. The top 25 genes activated (blue bars) and the top 25 repressed (green bars) by prednisolone in untreated control cells are shown, with the fold-change in CASP1 overexpressing cells also shown by the adjacent gold bars. Additionally, control and CASP1 overexpressing cells were treated with and without prednisolone and LPS/ATP and protein lysates were collected for determination of Bim protein levels, a known glucocorticoid response gene (panel A inset).
Figure 4B:
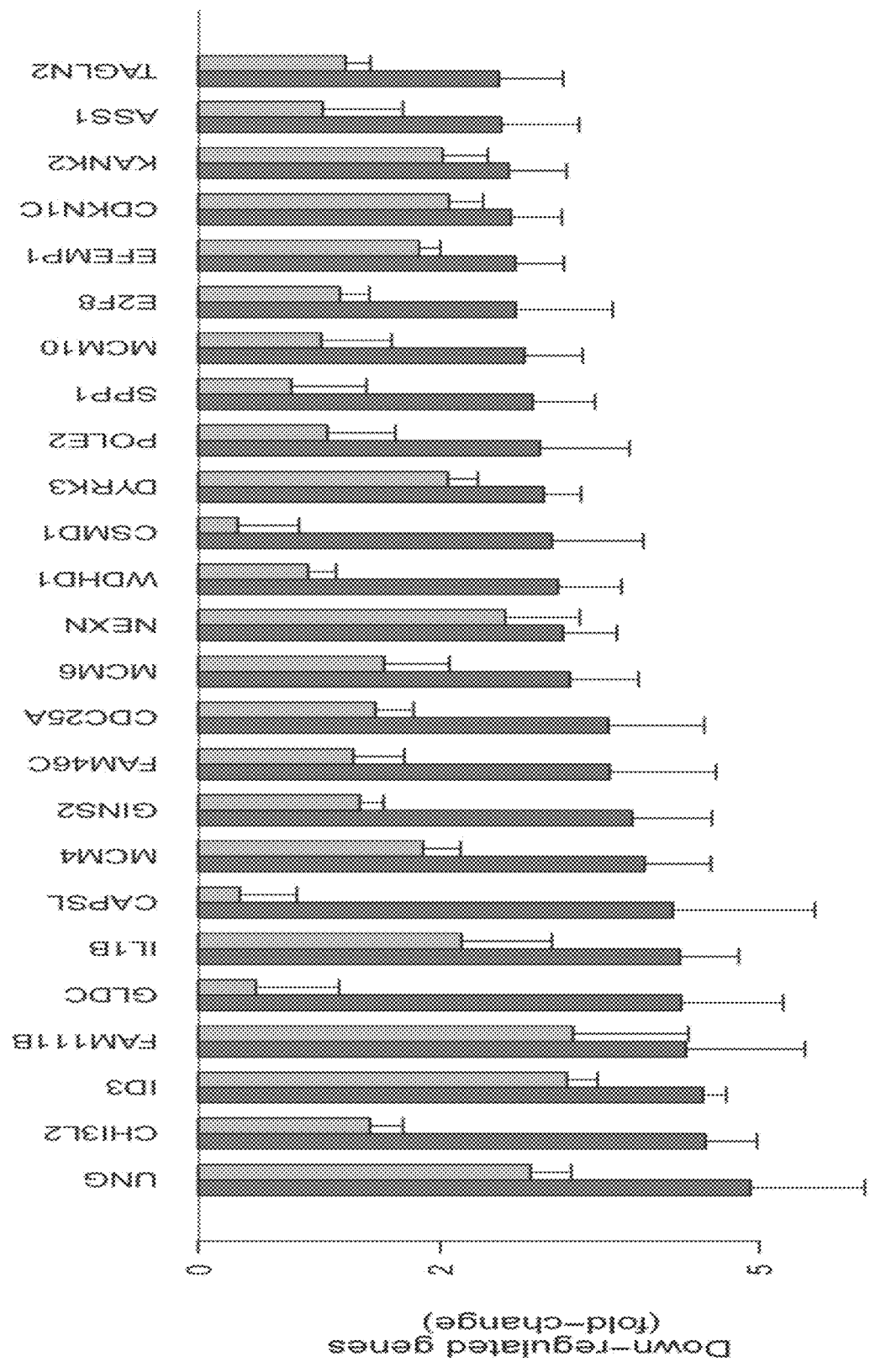
Figure 5:
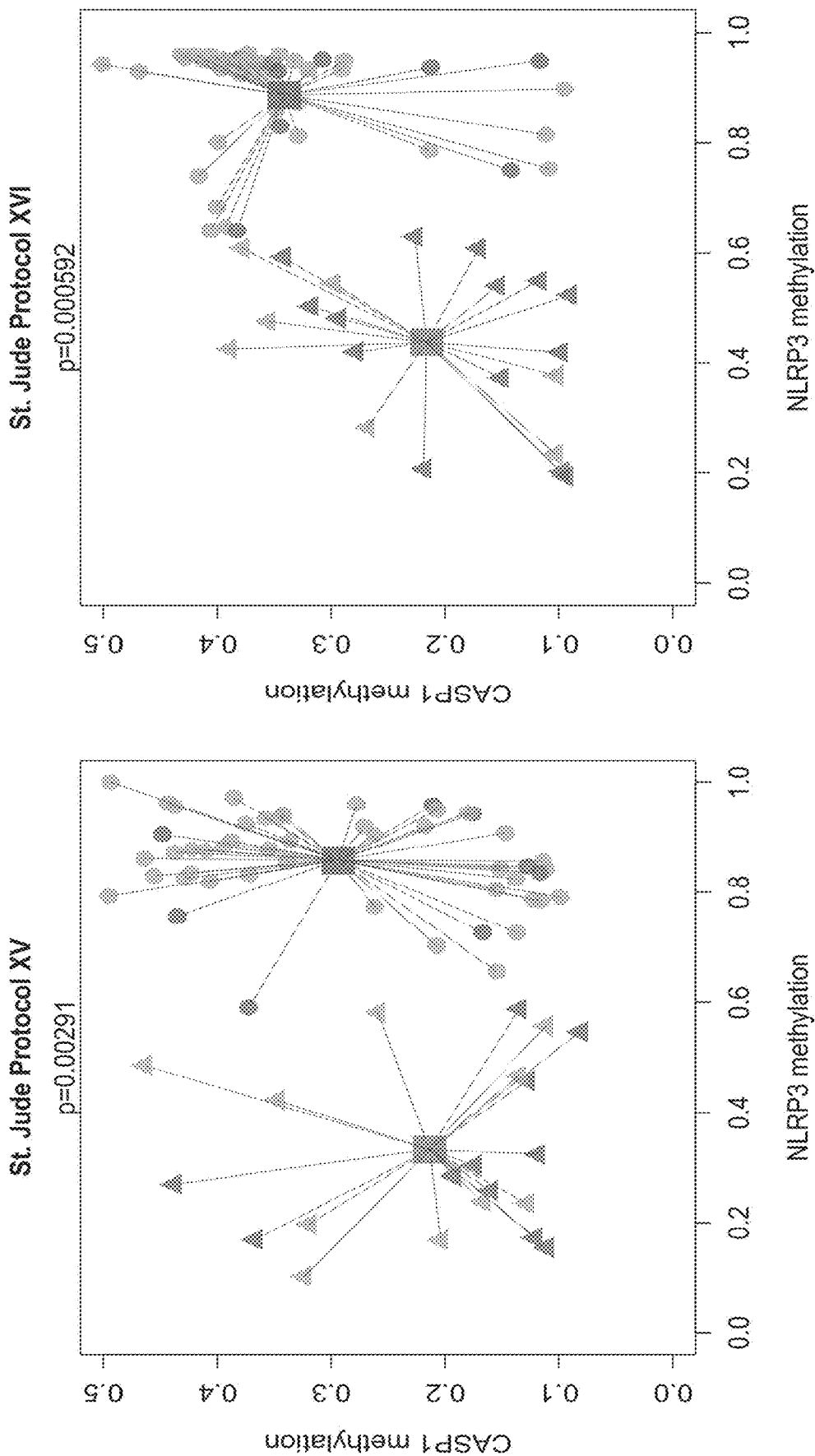
FIG. 5 shows that k-means clustering analysis (▲ represents k-means identified group A, ● represents k-means identified group B, pink and blue squares represent k-means identified centers for group A and B respectively) utilizing only CASP1 and NLRP3 methylation status significantly discriminated sensitive leukemias (green symbols, higher methylation) from resistant leukemias (red symbols, lower methylation) in both St. Jude Protocol XV and St. Jude Protocol XVI patients.
Figure 7:
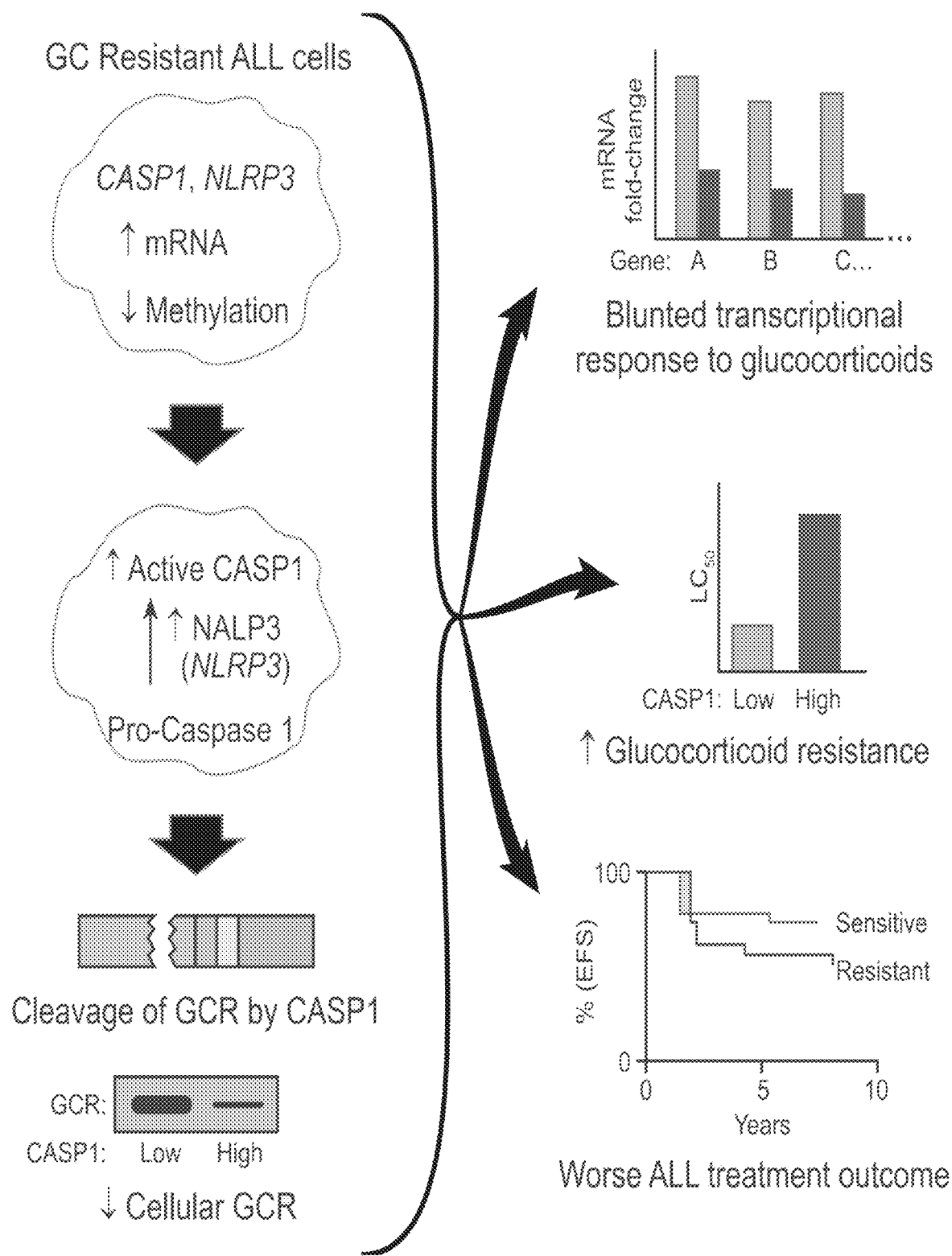
FIG. 7 is a schematic diagram depicting overarching pathway and phenotypic consequences in patients.

Because glucocorticoids regulate expression of target genes by binding to the glucocorticoid receptor, triggering translocation into the nucleus and association with a glucocorticoid response element to increase or decrease gene transcription, the present inventors assessed the ability of glucocorticoids to influence gene expression in the presence and absence of CASP1 enforced over-expression (FIGS. 4A, 4B). This revealed markedly diminished glucocorticoid-induced changes in gene expression in cells with CASP1 enforced over-expression compared to controls. Additionally, induction of Bim protein levels, a known glucocorticoid response gene was markedly blunted in CASP1 overexpressing cells (FIG. 4A inset). Genome-wide assessment of changes in gene expression after glucocorticoid treatment, revealed 104 genes that were induced following glucocorticoid treatment of control cells, 64 (62%) of which had lower (by at least 25%) induction in CASP1 over-expressing cells. Among these genes, the mean induction in control cells was 7.8-fold, compared to only 4.4-fold in CASP1 over-expressing cells (Paired t-test p=0.015). Analysis of the sequences of these 104 genes (including 5 kilobases up and downstream of each), revealed a significant enrichment in these genes (54/104, 52%) of known glucocorticoid response elements (GR binding motif, Table 1, motifs 1-9, (Dunham et al., 2012; Meijsing et al., 2009; Reddy et al., 2009)) or a genomic region shown by CHiP-seq to bind the GR (Reddy et al., 2009), as compared to only 28% (1409/5000) of the randomly selected unchanged genes (Fisher's Exact Test p=4.9×10$^{-7}$). Inclusion of an additional motif containing the top two most frequent bases at each position of a previously reported motif (Dunham et al., 2012) (motif 10, Table 1) increased the percentage of up-regulated genes with a glucocorticoid response element to 64% (67/104) among the transactivated genes.

Of the 28 genes whose expression was down-regulated following glucocorticoid treatment of control cells, 23 (82%) of these genes had lower (by at least 25%) down-regulation in CASP1 over-expressing cells. Among these genes, the mean reduction in control cells was 3.1-fold, compared to only 1.7-fold in CASP1 over-expressing cells (Paired t-test p=7.5×10$^{-11}$). Analysis of the sequence of these 28 genes, including 5 kilobases up and downstream, revealed a significant enrichment (9/28, 32%) of NF-κB binding motifs (a transcription factor known to interact with an activated glucocorticoid receptor, Table 1, motif 11) or a genomic region shown by CHiP-seq to bind to the GR (Reddy et al., 2009), as compared to randomly selected unchanged genes (849/5000, 17%; Fisher's Exact Test p=0.04). The top 25 up-regulated and down-regulated genes in control cells and their changes in cells with CASP1 enforced over-expression are depicted in FIG. 4, with the complete list of glucocorticoid-modulated genes provided in the supplement (Tables 2-4).

CASP1 and NLRP3 Expression are Higher in Leukemia Cells at Relapse

Figure 8A:
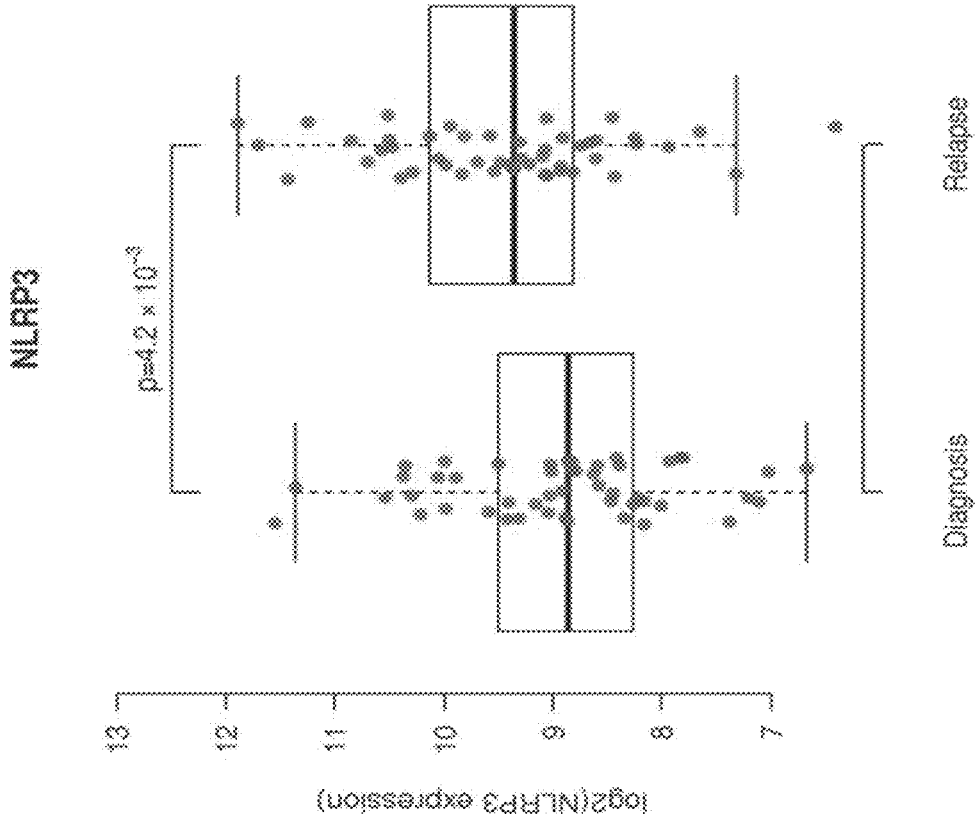
FIG. 8 shows that CASP1 and NLRP3 expression is higher in leukemia cells at the time of disease relapse. Expression levels of CASP1 (panel A) and NLRP3 (panel B) in leukemia cells were obtained from 49 patients at diagnosis and at the time of relapse. Quantile normalized measures of gene expression revealed significantly higher expression of NLRP3 and CASP1 at relapse. Paired t-test values are shown for panels A and B.
Figure 8B:
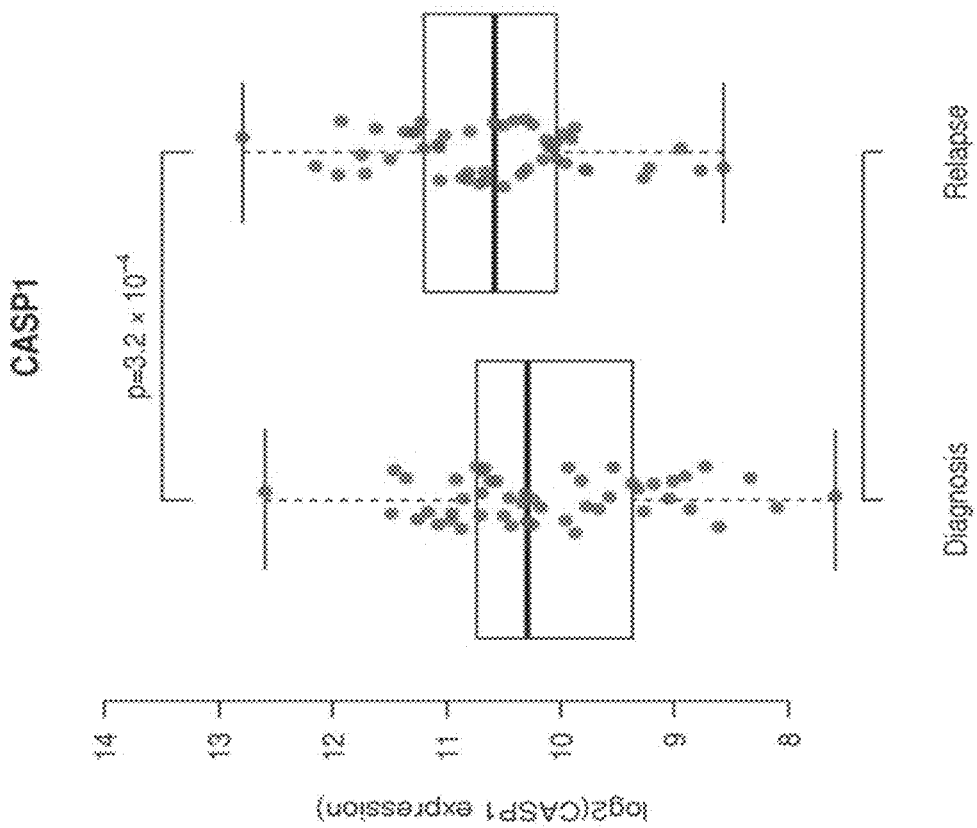

To determine whether CASP1 and NLRP3 expression differed in leukemia cells at the time of disease recurrence, we examined the expression levels of CASP1 and NLRP3 in paired ALL cells obtained at diagnosis and relapse from 49 patients (FIG. 8). This revealed significantly higher expression of both CASP1 and NLRP3 in ALL cells at the time of relapse when compared to the corresponding samples obtained from the same patients at diagnosis (Paired t-test p=3.2×10$^{-4}$ and 4.2×10$^{-3}$ respectively).

Figure 9A:
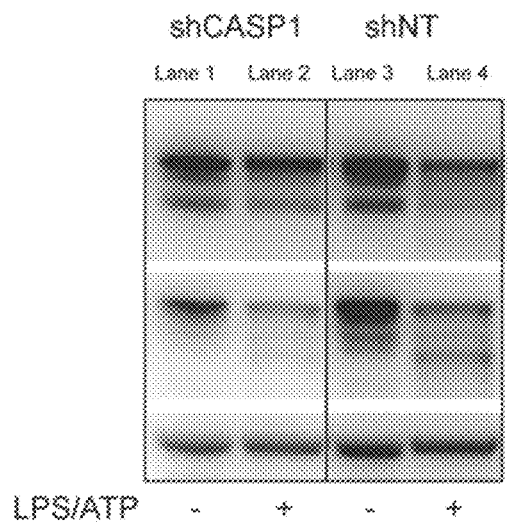
FIGS. 9A-D show that knockdown or inhibition of CASP1 reverses GR cleavage and prednisolone resistance. NALM-6 cells overexpressing CASP1 were stably transduced with lentiviral vectors (Sigma-Aldrich, St. Louis, Mo.) containing non-targeting scrambled hairpin (shNT, Sequence: CCGGCAACAAGATGAAGAGCAC-CAACTCGAGTTGGTGCTCTTCATCTTGTTGTTTTT (SEQ ID NO: 13)) or shRNA hairpins targeting CASP1 (shCASP1, Sequence: CCGGCTACAACT-CAATGCAATCTTTCTCGAGAAAGATTGCATT-GAGTTGTAGTTTTT (SEQ ID NO: 14)). The two cell lines were cultured for 48 hours in the presence and absence of LPS/ATP to allow for the activation of CASP1, and subsequently analyzed on Western blot for the expression levels of CASP1 and glucocorticoid receptor (GR) (Panel A). The quantified signal intensities of 90-kDa GR and 20-kDa active CASP1 normalized for the loading control HSP90, are shown in the bar graph (Panel A). After activation of CASP1 (Panel A, lane 2 and 4), the level of the GR is approximately 2-fold lower in scrambled hairpin cells (Panel A, lane 4), whereas cells in which CASP1 had been knocked down via the shCASP1 showed minimal degradation of the GR (Panel A, lane 2). The sensitivity (LC50) of shCASP1 and shNT cells to prednisolone was determined by MTT assays (Panel B). In the absence of CASP1 activation (−LPS/ATP), the PRED-LC50 of shCASP1 and shNT cells were comparable (Panel B, brown and blue bars). However, upon activation of CASP1 (+LPS/ATP), shCASP1 cells were 44-fold more sensitive to prednisolone (lower LC50) compared to shNT cells (Panel B, light brown and teal bars). Error bars represent S.E.M; n=4 replicate experiments. Transduction of CrmA (catalytic inhibitor of CASP1 protein; nucleotide sequence shown in SEQ ID NO: 15) or GFP in CASP1 overexpressing cells showed effects similar to knockdown of CASP1 by shRNA. In the absence of LPS/ATP33 induced CASP1 activation, the PRED-LC50 for CrmA-expressing cells and GFP-expressing cells were comparable (Panel D, brown and blue bars). However, upon activation of CASP1 by LPS/ATP, CrmA blocked CASP1 induced GR cleavage (Panel C) and increased GC sensitivity by 43-fold compared to the GFP expressing control cells (Panel D, light brown and teal bars).
Figure 9C:
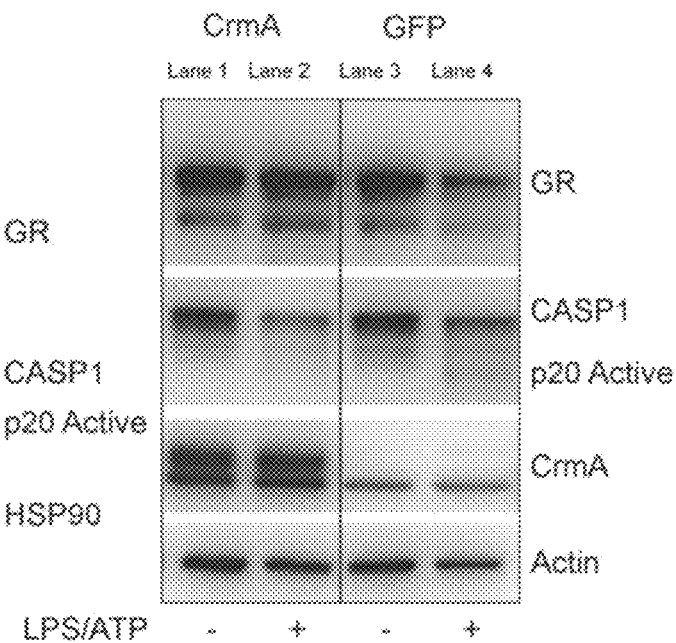
Figure 9C:
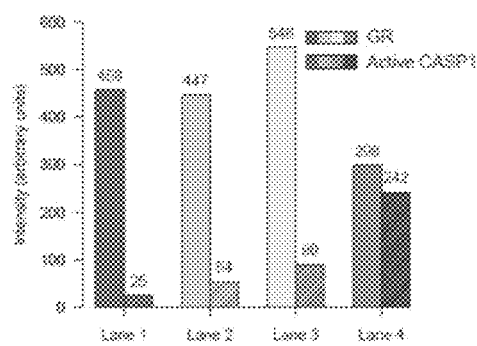
Figure 9C:
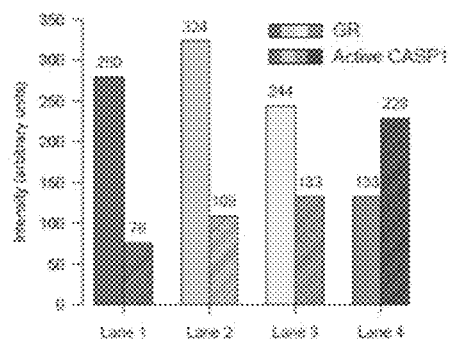
Figure 9B:
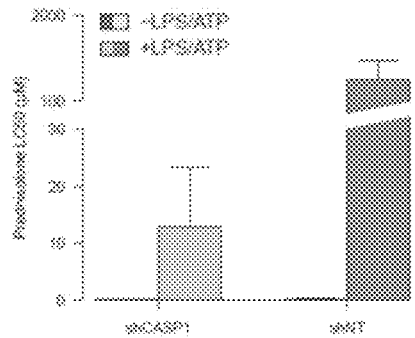

CASP1 Inhibition Reverses CASP1-Induced GR-Cleavage and Glucocorticoid Resistance To determine whether inhibition of CASP1 could diminish CASP1-induced glucocorticoid receptor cleavage and increase sensitivity to glucocorticoid treatment, shRNA (SEQ ID NO: 14) was used to knockdown overexpressed CASP1. This revealed that knockdown of CASP1 expression by ~50% (FIG. 9A, shCASP1) reduced CASP1-induced GR cleavage (FIG. 9A, shCASP1), and markedly enhanced glucocorticoid sensitivity (12.8±4.7 μM vs. 570±423.2 μM, mean±S.E.M., 44-fold reduction in LC50, t-test p=0.028) (FIG. 9B, shCASP1) in CASP1 overexpressing ALL cells when compared to cells transduced with scrambled non-targeting shRNA hairpin (FIG. 9A, shNT; SEQ ID NO: 13).

Figure 9D:
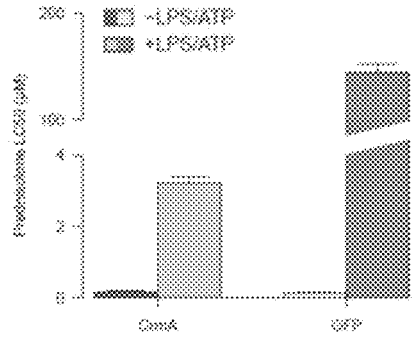

Likewise, when CASP1 overexpressing NALM-6 cells were transduced with the gene encoding CrmA (cytokine response modifier A; SEQ ID NO: 15), a known inhibitor of CASP1 catalytic activity (Garcia-Calvo et al., 1998; Komiyama et al., 1994; Ray et al., 1992), this blocked CASP1 induced GR cleavage (FIG. 9C) and markedly increased sensitivity to glucocorticoid treatment (3.2±0.2 μM vs. 137.3±24.3 μM, mean±S.E.M., 43-fold reduction in LC50, t-test p=0.011, FIG. 9D) when compared to GFP transfected controls.

Figure 10:
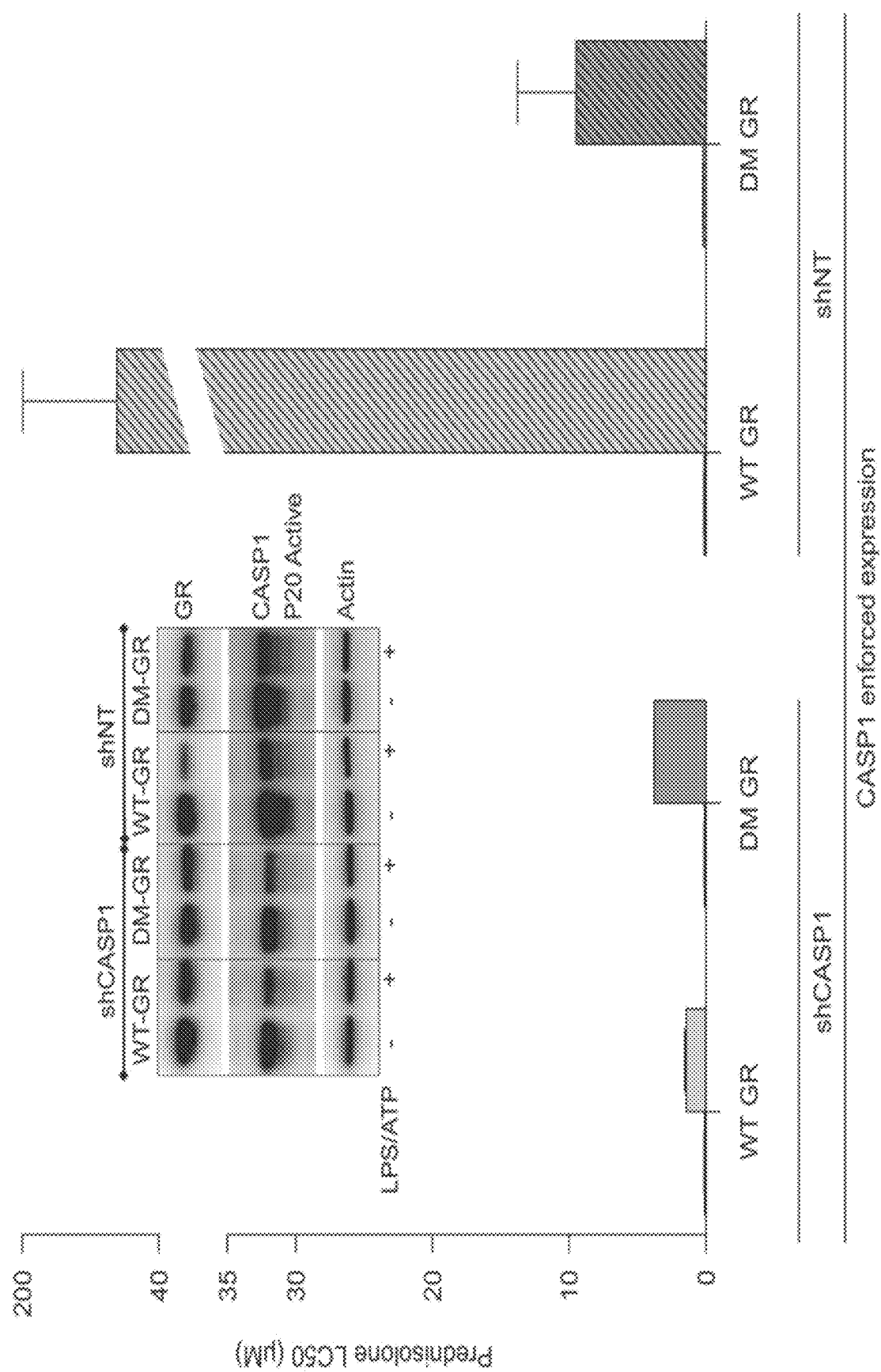
FIG. 10 shows that expression of CASP1 cleavage site double mutagenized GR reverses CASP1-induced prednisolone resistance. NALM-6 cells overexpressing CASP1 co-transfected with either non-targeting scrambled hairpin (shNT; SEQ ID NO: 13) or shRNA hairpins targeting CASP1 (shCASP1; SEQ ID NO: 14) were stably transduced with lentiviral vectors (Addgene plasmid 25890; Sigma-Aldrich, St. Louis, Mo.) containing a wild-type glucocorticoid receptor (SEQ ID NO: 16) or a glucocorticoid receptor in which both CASP1 cleavage sites had been eliminated (double mutagenized GR, DM-GR (SEQ ID NO: 17)). The sensitivity (LC50) of these cells to prednisolone was determined by MTT assays, revealing that cells overexpressing a GR without CASP1 cleavage sites remained sensitive to glucocorticoids when CASP1 was over-expressed. The inset is a western blot depicting recombinant GR protein levels (wild-type, or double mutagenized), in cells at time of MTT drug sensitivity assays.
Figure 11:
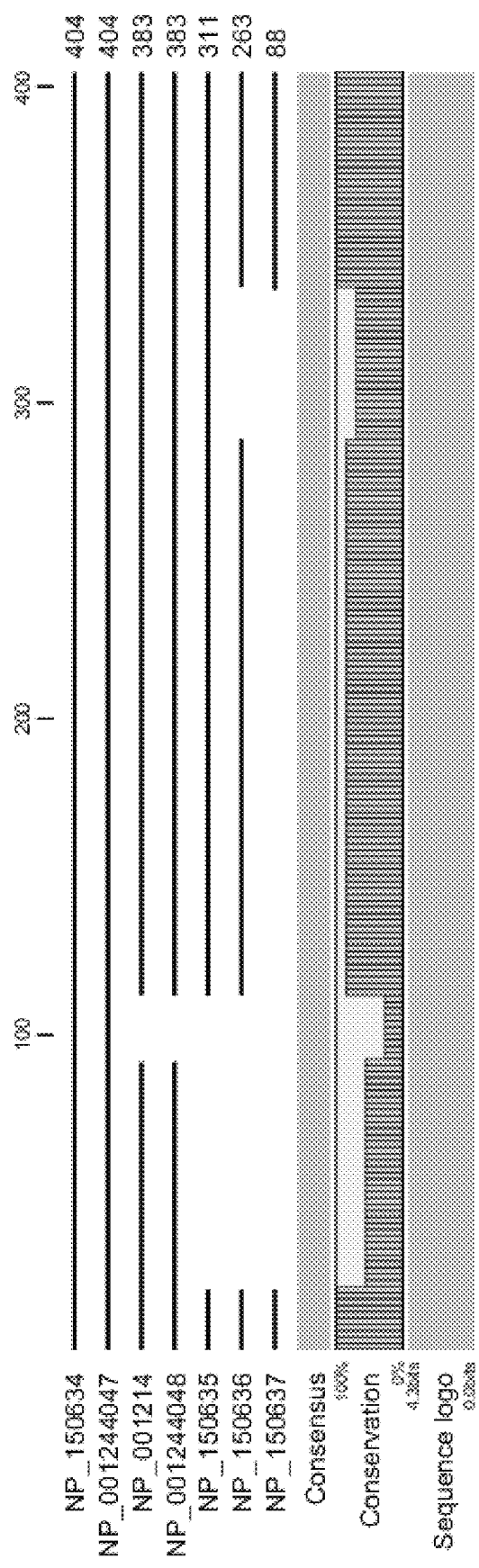
FIG. 11 depicts GenBank Accession Nos.: Alpha precursor isoforms: NP_150634.1; NP_001244047.1; Beta precursor isoforms: NP_001214.1, NP_001244048.1; Gamma precursor isoforms: NP_150635.1; Delta precursor isoforms: NP_150636.1; and Epsilon precursor isoforms: NP_150637.1.

Expression of a Glucocorticoid Receptor Mutated to Eliminate CASP Cleavage Sites Markedly Attenuated CASP1 Induced Resistance to Glucocorticoids Full-length wild-type GR (SEQ ID NO: 16) or a GR that had been mutated to eliminate the CASP1 cleavage sites (i.e., alanines substituted for the LLID (SEQ ID NO: 20) and IKQE (SEQ ID NO: 22) motifs identified in in vitro enzymatic assays; SEQ ID NO: 17), were overexpressed in leukemia cells overexpressing CASP1 in combination with either shRNA-based knockdown of overexpressed CASP1 or non-targeting shRNA control. Enforced expression of wild-type GR was unable to reverse CASP1-induced glucocorticoid resistance, whereas expression of a GR without the CASP1 cleavage sites markedly attenuated CASP1-induced glucocorticoid resistance (9.4-fold reduction in LC50), restoring sensitivity to levels similar to cells with shRNA-based knockdown of overexpressed CASP1 (FIG. 10).

Discussion

The experiments disclosed herein have revealed a novel mechanism by which CASP1 and its activator NLRP3 modulate the biological and pharmacological effects of glucocorticoids via cleavage of the glucocorticoid receptor (GR). Glucocorticoids mediate their effects by binding to the GR, causing it to translocate into the nucleus where it modulates the expression of genes that contain a glucocorticoid response element (GRE). Low cellular levels of functional GR, due either to siRNA knockdown (Reddy et al., 2009; Wang et al., 2004), rare mutations in the human NR3C1 gene encoding the GR (Charmandari et al., 2008) or heterogeneity in the cellular levels of GR in leukemia cells by undefined mechanisms (Pui et al., 1984), have all been shown to alter response to glucocorticoids (i.e., lower functional GR associated with less response). However, prior to the current work, it was not known that CASP1 can cleave the GR and thereby reduce functional receptor levels and modulate cellular response to glucocorticoids. The present inventors have identified this new mechanism after first observing that primary leukemia cells that express high levels of CASP1 and NLRP3 are relatively resistant to glucocorticoids. The present example also shows hypomethylation of the CASP1 and NLRP3 genes in leukemia cells expressing higher levels of their messenger RNAs. As further demonstrated herein, recombinant CASP1 cleaves the GR in its transactivation domain, and forced overexpression of CASP1 coupled with its activation via the NLRP3 inflammasome causes human leukemia cells to become more resistant to glucocorticoids. The present example also shows that over-expression of CASP1 significantly alters the transcriptional response of human lymphoblasts to glucocorticoid treatment, causing lower induction of gene expression for 64 of 104 genes that were induced in control cells after steroid treatment. Likewise, demonstrated herein is markedly lower repression of gene expression for 23 of 28 genes that were down-regulated after glucocorticoid treatment of control cells. The fact that not all GR-responsive genes were affected by CASP1 over-expression likely reflects differences among genes in their sensitivity to activated GR as a transcription factor and because there was only a partial reduction in GR levels in CASP1 over-expressing cells. Whether glucocorticoids cause transactivation or transrepression of a given gene is determined in part by the presence or absence of either a positive glucocorticoid response element, leading to transactivation or a negative GRE leading to transrepression, although these GREs have not been fully elucidated. Glucocorticoids may also repress gene expression via binding of the activated GR to transcription factors such as NF-κB and AP1 (McKay and Cidlowski, 1998; Teurich and Angel, 1995). Although the present inventors found a significant enrichment of positive GREs among transactivated genes and negative GREs in transrepressed gene, failure to find GREs in all genes likely reflects their current state of incomplete definition. The broad spectrum of genes affected in CASP1 over-expressing cells indicates that these findings likely have broader implications, beyond the modulation of the antileukemic effects of glucocorticoids.

It is demonstrated herein that activation of the NLRP3 inflammasome is likewise required to activate over-expressed CASP1 in human leukemia cells, but that in a role distinct from its promotion of inflammation, activated CASP1 modulates the level of GR and cellular response to glucocorticoids. CASP1 is known to have pro-inflammatory effects, including the activation of inflammatory cytokines (e.g., interleukin 1β and interleukin 18). The findings disclosed herein raise the possibility that during inflammatory processes, CASP1 negatively regulates anti-inflammatory GC signaling to further amplify its pro-inflammatory effects. Taken together, these results reveal a novel mechanism whereby leukemia cells develop resistance to glucocorticoids via epigenetic changes that cause over-expression of CASP1 and NLRP3, leading to enhanced CASP1-mediated cleavage of the GR, and diminished cellular response to glucocorticoids.

As further shown herein, overexpression of a glucocorticoid receptor that was mutated to eliminate the CASP1 cleavage sites mitigated the effects of CASP1 over-expression on leukemia cell sensitivity to glucocorticoids. Additionally, when CASP1 expression was knocked down in CASP1 over-expressing cells using shRNA, the present inventors were able to reverse CASP1-induced GR cleavage and markedly increase sensitivity to glucocorticoids, suggesting CASP1 inhibition as a novel therapeutic strategy. The present experiments showing that CrmA inhibition of CASP1 catalytic activity restores sensitivity to glucocorticoids in CASP1 over-expressing leukemia cells provide a further proof of principle for this strategy.

REFERENCES

Boehm, J. S., Zhao, J. J., Yao, J., Kim, S. Y., Firestein, R., Dunn, I. F., Sjostrom, S. K., Garraway, L. A., Weremowicz, S., Richardson, A. L., et al. (2007). Integrative genomic approaches identify IKBKE as a breast cancer oncogene. Cell 129, 1065-1079.

Boxer, M. B., Shen, M., Auld, D. S., Wells, J. A., and Thomas, C. J. (2010). A small molecule inhibitor of Caspase 1. In Probe Reports from the NIH Molecular Libraries Program, (Bethesda (Md.)).

Charmandari, E., Ichijo, T., Jubiz, W., Baid, S., Zachman, K., Chrousos, G. P., and Kino, T. (2008). A novel point mutation in the amino terminal domain of the human glucocorticoid receptor (hGR) gene enhancing hGR-mediated gene expression. The Journal of clinical endocrinology and metabolism 93, 4963-4968.

Cheok, M. H., Yang, W., Pui, C. H., Downing, J. R., Cheng, C., Naeve, C. W., Relling, M. V., and Evans, W. E. (2003). Treatment-specific changes in gene expression discriminate in vivo drug response in human leukemia cells. Nat Genet 34, 85-90.

Den Boer, M. L., Harms, D. O., Pieters, R., Kazemier, K. M., Gobel, U., Korholz, D., Graubner, U., Haas, R. J., Jorch, N., Spaar, H. J., et al. (2003). Patient stratification based on prednisolone-vincristine-asparaginase resistance profiles in children with acute lymphoblastic leukemia. J Clin Oncol 21, 3262-3268.

Dordelmann, M., Reiter, A., Borkhardt, A., Ludwig, W. D., Gotz, N., Viehmann, S., Gadner, H., Riehm, H., and Schrappe, M. (1999). Prednisone response is the strongest predictor of treatment outcome in infant acute lymphoblastic leukemia. Blood 94, 1209-1217.

Dunham, I., Kundaje, A., Aldred, S. F., Collins, P. J., Davis, C. A., Doyle, F., Epstein, C. B., Frietze, S., Harrow, J., Kaul, R., et al. (2012). An integrated encyclopedia of DNA elements in the human genome. Nature 489, 57-74.

Garcia-Calvo, M., Peterson, E. P., Leiting, B., Ruel, R., Nicholson, D. W., and Thornberry, N. A. (1998). Inhibition of human caspases by peptide-based and macromolecular inhibitors. The Journal of biological chemistry 273, 32608-32613.

Gautier, L., Cope, L., Bolstad, B. M., and Irizarry, R. A. (2004). affy-analysis of Affymetrix GeneChip data at the probe level. Bioinformatics 20, 307-315.

Gentleman, R. C., Carey, V. J., Bates, D. M., Bolstad, B., Dettling, M., Dudoit, S., Ellis, B., Gautier, L., Ge, Y., Gentry, J., et al. (2004). Bioconductor: open software development for computational biology and bioinformatics. Genome Biol 5, R80.

Holleman, A., Cheok, M. H., den Boer, M. L., Yang, W., Veerman, A. J., Kazemier, K. M., Pei, D., Cheng, C., Pui, C. H., Relling, M. V., et al. (2004). Gene-expression patterns in drug-resistant acute lymphoblastic leukemia cells and response to treatment. The New England journal of medicine 351, 533-542.

Hubbell, E., Liu, W. M., and Mei, R. (2002). Robust estimators for expression analysis. Bioinformatics 18, 1585-1592.

Kaspers, G. J., Veerman, A. J., Pieters, R., Van Zantwijk, C. H., Smets, L. A., Van Wering, E. R., and Van Der Does-Van Den Berg, A. (1997). In vitro cellular drug resistance and prognosis in newly diagnosed childhood acute lymphoblastic leukemia. Blood 90, 2723-2729.

Komiyama, T., Ray, C. A., Pickup, D. J., Howard, A. D., Thornberry, N. A., Peterson, E. P., and Salvesen, G. (1994). Inhibition of interleukin-1 beta converting enzyme by the cowpox virus serpin CrmA. An example of cross-class inhibition. The Journal of biological chemistry 269, 19331-19337.

Mariathasan, S., Weiss, D. S., Newton, K., McBride, J., O'Rourke, K., Roose-Girma, M., Lee, W. P., Weinrauch, Y., Monack, D. M., and Dixit, V. M. (2006). Cryopyrin activates the inflammasome in response to toxins and ATP. Nature 440, 228-232.

Martinon, F., Petrilli, V., Mayor, A., Tardivel, A., and Tschopp, J. (2006). Gout-associated uric acid crystals activate the NALP3 inflammasome. Nature 440, 237-241.

McKay, L. I., and Cidlowski, J. A. (1998). Cross-talk between nuclear factor-kappa B and the steroid hormone receptors: mechanisms of mutual antagonism. Mol Endocrinol 12, 45-56.

Meijsing, S. H., Pufall, M. A., So, A. Y., Bates, D. L., Chen, L., and Yamamoto, K. R. (2009). DNA binding site sequence directs glucocorticoid receptor structure and activity. Science 324, 407-410.

Muzio, M., Salvesen, G. S., and Dixit, V. M. (1997). FLICE induced apoptosis in a cell-free system. Cleavage of caspase zymogens. The Journal of biological chemistry 272, 2952-2956.

Ogura, Y., Sutterwala, F. S., and Flavell, R. A. (2006). The inflammasome: first line of the immune response to cell stress. Cell 126, 659-662.

Pieters, R., Huismans, D. R., Loonen, A. H., Hahlen, K., van der Does-van den Berg, A., van Wering, E. R., and Veerman, A. J. (1991). Relation of cellular drug resistance to long-term clinical outcome in childhood acute lymphoblastic leukaemia. Lancet 338, 399-403.

Pui, C. H., Campana, D., Pei, D., Bowman, W. P., Sandlund, J. T., Kaste, S. C., Ribeiro, R. C., Rubnitz, J. E., Raimondi, S. C., Onciu, M., et al. (2009). Treating childhood acute lymphoblastic leukemia without cranial irradiation. The New England journal of medicine 360, 2730-2741.

Pui, C. H., Dahl, G. V., Rivera, G., Murphy, S. B., and Costlow, M. E. (1984). The relationship of blast cell glucocorticoid receptor levels to response to single-agent steroid trial and remission response in children with acute lymphoblastic leukemia. Leukemia research 8, 579-585.

Ray, C. A., Black, R. A., Kronheim, S. R., Greenstreet, T. A., Sleath, P. R., Salvesen, G. S., and Pickup, D. J. (1992). Viral inhibition of inflammation: cowpox virus encodes an inhibitor of the interleukin-1 beta converting enzyme. Cell 69, 597-604.

Reddy, T. E., Pauli, F., Sprouse, R. O., Neff, N. F., Newberry, K. M., Garabedian, M. J., and Myers, R. M. (2009). Genomic determination of the glucocorticoid response reveals unexpected mechanisms of gene regulation. Genome research 19, 2163-2171.

Schroder, K., and Tschopp, J. (2010). The inflammasomes. Cell 140, 821-832.

Stouffer, S. A., Suchman, E. A., DeVinney, L. C., Star, S. A., and Williams Jr, R. M. (1949). The American soldier: adjustment during army life. (Studies in social psychology in World War II, Vol. 1.).

Teurich, S., and Angel, P. (1995). The glucocorticoid receptor synergizes with Jun homodimers to activate AP-1-regulated promoters lacking GR binding sites. Chemical senses 20, 251-255.

Wang, J. C., Derynck, M. K., Nonaka, D. F., Khodabakhsh, D. B., Haqq, C., and Yamamoto, K. R. (2004). Chromatin immunoprecipitation (ChIP) scanning identifies primary glucocorticoid receptor target genes. Proceedings of the National Academy of Sciences of the United States of America 101, 15603-15608.

Wellington, C. L., Ellerby, L. M., Hackam, A. S., Margolis, R. L., Trifiro, M. A., Singaraja, R., McCutcheon, K., Salvesen, G. S., Propp, S. S., Bromm, M., et al. (1998). Caspase cleavage of gene products associated with triplet expansion disorders generates truncated fragments containing the polyglutamine tract. J Biol Chem 273, 9158-9167.

Yeoh, E. J., Ross, M. E., Shurtleff, S. A., Williams, W. K., Patel, D., Mahfouz, R., Behm, F. G., Raimondi, S. C., Relling, M. V., Patel, A., et al. (2002). Classification, subtype discovery, and prediction of outcome in pediatric acute lymphoblastic leukemia by gene expression profiling. Cancer Cell 1, 133-143.

Yang, X., Boehm, J. S., Salehi-Ashtiani, K., Hao, T., Shen, Y., Lubonja, R., Thomas, S. R., Alkan, O, Bhimdi, T., Green, T. M., et al. (2011). A public genome-scale lentiviral expression library of human ORFS. Nature methods 8, 659-661.

Yudt, M. R., and Cidlowski, J. A. (2002). The glucocorticoid receptor: coding a diversity of proteins and responses through a single gene. Mol Endocrinol 16, 1719-1726.

Zhou, R., Tardivel, A., Thorens, B., Choi, I., and Tschopp, J. (2010). Thioredoxin-interacting protein links oxidative stress to inflammasome activation. Nature immunology 11, 136-140.

LIST OF SEQUENCES:

| SEQ ID | SEQUENCE | organism |
|---|---|---|
| 1 | MADKVLKEKRKLFIRSMGEGTINGLLDELLQTRVLNKEEMEKVKRENATVMDK TRALIDSVIPKGAQACQICITYICEEDSYLAGTLGLSADQTSGNYLNMQDSQGVLS SFPAPQAVQDNPAMPTSSGSEGNVKLCSLEEAQRIWKQKSAEIYPIMDKSSRTRL ALIICNEEFDSIPRRTGAEVDITGMTMLLQNLGYSVDVKKNLTASDMTTELEAFA HRPEHKTSDSTFLVFMSHGIREGICGKKHSEQVPDILQLNAIFNMLNTKNCPSLKD KPKVIIIQACRGDSPGVVWFKDSVGVSGNLSLPTTEEFEDDAIKKAHIEKDFIAFCS STPDNVSWRHPTMGSVFIGRLIEHMQEYACSCDVEEIFRKVRFSFEQPDGRAQMP TIERVTLTRCFYLFPGH | Homo sapiens |
| 2 | MKMASTRCKLARYLEDLEDVDLKKFKMHLEDYPPQKGCIPLPRGQTEKADHVD LATLMIDFNGEEKAWAMAVWIFAAINRRDLYEKAKRDEPKWGSDNARVSNPTV ICQEDSIEEEWMGLLEYLSRISICKMKKDYRKKYRKYVRSRFQCIEDRNARLGES VSLNKRYTRLRLIKEHRSQQEREQELLAIGKTKTCESPVSPIKMELLFDPDDEHSE PVHTVVFQGAAGIGKTILARKMMLDWASGTLYQDRFDYLFYIHCREVSLVTQRS LGDLIMSCCPDPNPPIHKIVRKPSRILFLMDGFDELQGAFDEHIGPLCTDWQKAER GDILLSSLIRKKLLPEASLLITTRPVALEKLQHLLDHPRHVEILGFSEAKRKEYFFK YFSDEAQARAAFSLIQENEVLFTMCFIPLVCWIVCTGLKQQMESGKSLAQTSKTT TAVYVFFLSSLLQPRGGSQEHGLCAHLWGLCSLAADGIWNQKILFEESDLRNHGL QKADVSAFLRMNLFQKEVDCEKFYSFIHMTFQEFFAAMYYLLEEEKEGRTNVPG SRLKLPSRDVTVLLENYGKFEKGYLIFVVRFLFGLVNQERTSYLEKKLSCKISQQI RLELLKWIEVKAKAKKLQIQPSQLELFYCLYEMQEEDFVQRAMDYFPKIEINLST RMDHMVSSFCIENCHRVESLSLGFLHNMPKEEEEEEKEGRHLDMVQCVLPSSSH AACSHGLVNSHLTSSFCRGLFSVLSTSQSLTELDLSDNSLGDPGMRVLCETLQHP GCNIRRLWLGRCGLSHECCFDISLVLSSNQKLVELDLSDNALGDFGIRLLCVGLK HLLCNLKKLWLVSCCLTSACCQDLASVLSTSHSLTRLYVGENALGDSGVAILCEK AKNPQCNLQKLGLVNSGLTSVCCSALSSVLSTNQNLTHLYLRGNTLGDKGIKLLC EGLLHPDCKLQVLELDNCNLTSHCCWDLSTLLTSSQSLRKLSLGNNDLGDLGVM MFCEVLKQQSCLLQNLGLSEMYFNYETKSALETLQEEKPELTVVFEPSW | Homo sapiens |

LIST OF SEQUENCES:

| SEQ ID | SEQUENCE | organism |
|---|---|---|
| 3 | GTCGGGGAAGGTTTTGAGAAAGAAGGGTCCCTGGACAAGAACCTTGTCATTT TCTGAGTGGCCGGTACCGAAAAGAGAGGAGGGAAGAACACACTGACTTTGAC TTTCATACGAAGCGGAAG | Homo sapiens |
| 4 | CTCCTTTGACTTCAACTCCTTATCACTTCTCAAACAGGTTACAGTATCGGGGC ATTAGTTGCCCTGTTTTTAAAAGAACGACTACCCAGTTCTACCGTAGCACTTC ACCAACAAGTGGCATT | Homo sapiens |
| 5 | CCTTGGAGATCAGACCTGTTGATAGCTGAAAACTGTTTGCTTTC | synthetic |
| 6 | GAAAGCAAACAGTTTTCAGCTATCAACAGGTCTGATCTCCAAGG | synthetic |
| 7 | CCTTGGAGATCAGACCTGTTGGCAGCTGAAAACTGTTTGCTTTC | synthetic |
| 8 | GAAAGCAAACAGTTTTCAGCTGCCAACAGGTCTGATCTCCAAGG | synthetic |
| 9 | CCTTGGAGATCAGACCTGGCGGCAGCTGAAAACTGTTTGCTTTC | synthetic |
| 10 | GAAAGCAAACAGTTTTCAGCTGCCGCCAGGTCTGATCTCCAAGG | synthetic |
| 11 | CCTTGGAGATCAGACGCGGCGGCAGCTGAAAACTGTTTGCTTTC | synthetic |
| 12 | GAAAGCAAACAGTTTTCAGCTGCCGCCGCGTCTGATCTCCAAGG | synthetic |
| 13 | CCGGCAACAAGATGAAGAGCACCAACTCGAGTTGGTGCTCTTCATCTTGTTGT TTTT | synthetic |
| 14 | CCGGCTACAACTCAATGCAATCTTTCTCGAGAAAGATTGCATTGAGTTGTAGT TTTT | synthetic |
| 15 | ATGGATATCTTCAGGGAAATCGCATCTTCTATGAAAGGAGAGAATGTATTCAT TTCTCCACCGTCAATCTCG TCAGTATTGACAATACTGTATTATGGAGCTAATGGATCCACTGCTGAACAGCT ATCAAAATATGTAGAAAAGGAGGCGGA CAAGAATAAGGATGATATCTCATTCAAGTCCATGAATAAAGTATATGGGCGA TATTCTGCAGTGTTTAAAGATTCCTTTT TGAGAAAAATTGGAGATAATTTCCAAACTGTTGACTTCACTGATTGTCGCACT GTAGATGCGATCAACAAGTGTGTTGAT ATCTTCACTGAGGGGAAAATTAATCCACTATTGGATGAACCATTGTCTCCAGA TACCTGTCTCCTAGCAATTAGTGCCGT ATACTTTAAAGCAAAATGGTTGATGCCATTTGAAAAGGAATTTACCAGTGATT ATCCCTTTTACGTATCTCCAACGGAAA TGGTAGATGTAAGTATGATGTCTATGTACGGCGAGGCATTTAATCACGCATCT GTAAAAGAATCATTCGGCAACTTTTCA ATCATAGAACTGCCATATGTTGGAGATACTAGTATGGTGGTAATTCTTCCAGA CAATATTGATGGACTAGAATCCATAGA ACAAAATCTAACAGATACAAATTTTAAGAAATGGTGTGACTCTATGGATGCT ATGTTTATCGATGTGCACATTCCCAAGT TTAAGGTAACAGGCTCGTATAATCTGGTGATGCGCTAGTAAAGTTGGGACT GACAGAGGTGTTCGGTTCAACTGGAGAT TATAGCAATATGTGTAATTCAGATGTGAGTGTCGACGCTATGATCCACAAAAC GTATATAGATGTCAATGAAGAGTATAC AGAAGCAGCTGCAGCAACTTGTGCGCTGGTGGCAGACTGTGCATCAACAGTT ACAAATGAGTTCTGTGCAGATCATCCGT TCATCTATGTGATTAGGCATGTCGATGGCAAAATTCTTTTCGTTGGTAGATAT TGCTCTCCAACAACTAATTAA | Orthopox virus vaccinia |
| 16 | MDSKES

LIST OF SEQUENCES:

| SEQ ID | SEQUENCE | organism |
|---|---|---|
| 17 | MDSKESLTPGREENPSSVLAQERGDVMDFYKTLRGGATVKVSASSPSLAVASQS DSKQRRLLVDFPKGSVSNAQQPDLSKAVSLSMGLYMGETETKVMGNDLGFPQQ GQISLSSGETDLKLLEESIANLNRSTSVPENPKSSASTAVSAAPIEKEFPKTHSDVS SEQQHLKGQTGTNGGNVKLYTTDQSTFDILQDLEFSSGSPGKETNESPWRSDAAA AENCLLSPLAGEDDSFLLEGNSNEDCKPLILPDTKPKIKDNGDLVLSSPSNVTLPQ VKTEKEDFIELCTPGVAAAAKLGTVYCQASFPGANIIGNKMSAISVHGVSTSGGQ MYHYDMNTASLSQQQDQKPIFNVIPPIPVGSENWNRCQGSGDDNLTSLGTLNFPG RTVFSNGYSSPSMRPDVSSPPSSSSTATTGPPPKLCLVCSDEASGCHYGVLTCGSC KVFFKRAVEGQHNYLCAGRNDCIIDKIRRKNCPACRYRKCLQAGMNLEARKTK KKIKGIQQATTGVSQETSENPGNKTIVPATLPQLTPTLVSLLEVIEPEVLYAGYDSS VPDSTWRIMTTLNMLGGRQVIAAVKWAKAIPGFRNLHLDDQMTLLQYSWMFL MAFALGWRSYRQSSANLLCFAPDLIINEQRMTLPCMYDQCKHMLYVSSELHRLQ VSYEEYLCMKTLLLLSSVPKDGLKSQELFDEIRMTYIKELGKAIVKREGNSSQNW QRFYQLTKLLDSMHEVVENLLNYCFQTFLDKTMSIEFPEMLAEIITNQIPKYSNGN IKKLLFHQK | Synthetic |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for treating glucocorticoid resistance or increasing glucocorticoid sensitivity in a subject in need thereof, wherein the expression level of CASP1 gene and/or NLRP3 gene in cells of the subject is increased as compared to a corresponding glucocorticoid-sensitive control, which method comprises administering to the subject a therapeutically effective amount of an inhibitor of CASP1.

2. The method of claim 1, wherein the method further comprises (i) determining the expression level of CASP1 gene and/or NLRP3 gene in the cells from the subject or (ii) determining the methylation level of CASP1 gene promoter and/or NLRP3 gene promoter in the cells from the subject.

3. The method of claim 1, wherein the expression level of CASP1 gene and/or NLRP3 gene in said cells is increased by at least 1.5-fold as compared to the corresponding expression level in the glucocorticoid-sensitive control.

4. The method of claim 1, wherein the inhibitor of CASP1 directly inhibits expression or function of CASP1.

5. The method of claim 1, wherein the inhibitor of CASP1 directly inhibits expression or function of NLRP3.

6. The method of claim 1, wherein the inhibitor of CASP1 inhibits NLRP3 inflammasome formation or NLRP3 inflammasome activity.

7. The method of claim 1, wherein the administration of the inhibitor of CASP1 results in an increased glucocorticoid sensitivity.

8. The method of claim 1, wherein the subject is human.

9. A method of treating a disease in a subject in need thereof, wherein the disease is treated with glucocorticoids and can acquire glucocorticoid resistance accompanied by an increased expression level of CASP1 gene and/or NLRP3 gene in cells of the subject as compared to a corresponding glucocorticoid-sensitive control, which method comprises administering to the subject (i) a therapeutically effective amount of an inhibitor of CASP1 and (ii) a therapeutically effective amount of a glucocorticoid.

10. The method of claim 9, wherein the disease is an inflammatory or an autoimmune disease.

11. The method of claim 9, wherein the disease is a glucocorticoid-resistant asthma.

12. The method of claim 9, wherein the method further comprises (i) determining the expression level of CASP1 gene and/or NLRP3 gene in the cells from the subject or (ii) determining the methylation level of CASP1 gene promoter and/or NLRP3 gene promoter in the cells from the subject.

13. The method of claim 9, wherein the expression level of CASP1 gene and/or NLRP3 gene in said cells is increased by at least 1.5-fold as compared to the corresponding expression level in the glucocorticoid-sensitive control.

14. The method of claim 9, wherein the inhibitor of CASP1 directly inhibits expression or function of CASP1.

15. The method of claim 9, wherein the inhibitor of CASP1 directly inhibits expression or function of NLRP3.

16. The method of claim 9, wherein the inhibitor of CASP1 inhibits NLRP3 inflammasome formation or NLRP3 inflammasome activity.

17. The method of claim 9, wherein the administration of the inhibitor of CASP1 results in an increased glucocorticoid sensitivity.

18. The method of claim 9, wherein the subject is human.

19. The method of claim 1, wherein the inhibitor of CASP1 is selected from interfering RNA, dsRNA, RNA polymerase III transcribed DNAs, ribozymes, and antisense nucleic acids.

20. The method of claim 19, wherein the interfering RNA is siRNA or shRNA.

21. The method of claim 9, wherein the inhibitor of CASP1 is selected from interfering RNA, dsRNA, RNA polymerase III transcribed DNAs, ribozymes, and antisense nucleic acids.

22. The method of claim 21, wherein the interfering RNA is siRNA or shRNA.

* * * * *

SEQUENCE LISTING

<160> NUMBER OF SEQ ID NOS: 27

<210> SEQ ID NO 1
<211> LENGTH: 404
<212> TYPE: PRT
<213> ORGANISM: Homo sapiens

<400> SEQUENCE: 1

Met Ala Asp Lys Val Leu Lys Glu Lys Arg Lys Leu Phe Ile Arg Ser
1               5                   10                  15

Met Gly Glu Gly Thr Ile Asn Gly Leu Leu Asp Glu Leu Leu Gln Thr
            20                  25                  30

Arg Val Leu Asn Lys Glu Glu Met Glu Lys Val Lys Arg Glu Asn Ala
        35                  40                  45

Thr Val Met Asp Lys Thr Arg Ala Leu Ile Asp Ser Val Ile Pro Lys
    50                  55                  60

Gly Ala Gln Ala Cys Gln Ile Cys Ile Thr Tyr Ile Cys Glu Glu Asp
65                  70                  75                  80

Ser Tyr Leu Ala Gly Thr Leu Gly Leu Ser Ala Asp Gln Thr Ser Gly
                85                  90                  95

Asn Tyr Leu Asn Met Gln Asp Ser Gln Gly Val Leu Ser Ser Phe Pro
            100                 105                 110

Ala Pro Gln Ala Val Gln Asp Asn Pro Ala Met Pro Thr Ser Ser Gly
        115                 120                 125

Ser Glu Gly Asn Val Lys Leu Cys Ser Leu Glu Glu Ala Gln Arg Ile
    130                 135                 140

Trp Lys Gln Lys Ser Ala Glu Ile Tyr Pro Ile Met Asp Lys Ser Ser
145                 150                 155                 160

```
Arg Thr Arg Leu Ala Leu Ile Ile Cys Asn Glu Glu Phe Asp Ser Ile
            165                 170                 175

Pro Arg Arg Thr Gly Ala Glu Val Asp Ile Thr Gly Met Thr Met Leu
        180                 185                 190

Leu Gln Asn Leu Gly Tyr Ser Val Asp Val Lys Lys Asn Leu Thr Ala
        195                 200                 205

Ser Asp Met Thr Thr Glu Leu Glu Ala Phe Ala His Arg Pro Glu His
    210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Asn Ala Ile Phe Asn Met Leu Asn Thr Lys Asn Cys Pro Ser
            260                 265                 270

Leu Lys Asp Lys Pro Lys Val Ile Ile Gln Ala Cys Arg Gly Asp
        275                 280                 285

Ser Pro Gly Val Val Trp Phe Lys Asp Ser Val Gly Val Ser Gly Asn
    290                 295                 300

Leu Ser Leu Pro Thr Thr Glu Glu Phe Glu Asp Asp Ala Ile Lys Lys
305                 310                 315                 320

Ala His Ile Glu Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
            340                 345                 350

Leu Ile Glu His Met Gln Glu Tyr Ala Cys Ser Cys Asp Val Glu Glu
        355                 360                 365

Ile Phe Arg Lys Val Arg Phe Ser Phe Glu Gln Pro Asp Gly Arg Ala
    370                 375                 380

Gln Met Pro Thr Thr Glu Arg Val Thr Leu Thr Arg Cys Phe Tyr Leu
385                 390                 395                 400

Phe Pro Gly His

<210> SEQ ID NO 2
<211> LENGTH: 1036
<212> TYPE: PRT
<213> ORGANISM: Homo sapiens

<400> SEQUENCE: 2

Met Lys Met Ala Ser Thr Arg Cys Lys Leu Ala Arg Tyr Leu Glu Asp
1               5                   10                  15

Leu Glu Asp Val Asp Leu Lys Lys Phe Lys Met His Leu Glu Asp Tyr
            20                  25                  30

Pro Pro Gln Lys Gly Cys Ile Pro Leu Pro Arg Gly Gln Thr Glu Lys
        35                  40                  45

Ala Asp His Val Asp Leu Ala Thr Leu Met Ile Asp Phe Asn Gly Glu
    50                  55                  60

Glu Lys Ala Trp Ala Met Ala Val Trp Ile Phe Ala Ala Ile Asn Arg
65                  70                  75                  80

Arg Asp Leu Tyr Glu Lys Ala Lys Arg Asp Glu Pro Lys Trp Gly Ser
                85                  90                  95

Asp Asn Ala Arg Val Ser Asn Pro Thr Val Ile Cys Gln Glu Asp Ser
            100                 105                 110

Ile Glu Glu Glu Trp Met Gly Leu Leu Glu Tyr Leu Ser Arg Ile Ser
        115                 120                 125
```

```
Ile Cys Lys Met Lys Lys Asp Tyr Arg Lys Lys Tyr Arg Lys Tyr Val
130                 135                 140

Arg Ser Arg Phe Gln Cys Ile Glu Asp Arg Asn Ala Arg Leu Gly Glu
145                 150                 155                 160

Ser Val Ser Leu Asn Lys Arg Tyr Thr Arg Leu Arg Leu Ile Lys Glu
                165                 170                 175

His Arg Ser Gln Gln Glu Arg Glu Gln Glu Leu Leu Ala Ile Gly Lys
            180                 185                 190

Thr Lys Thr Cys Glu Ser Pro Val Ser Pro Ile Lys Met Glu Leu Leu
            195                 200                 205

Phe Asp Pro Asp Asp Glu His Ser Glu Pro Val His Thr Val Val Phe
210                 215                 220

Gln Gly Ala Ala Gly Ile Gly Lys Thr Ile Leu Ala Arg Lys Met Met
225                 230                 235                 240

Leu Asp Trp Ala Ser Gly Thr Leu Tyr Gln Asp Arg Phe Asp Tyr Leu
                245                 250                 255

Phe Tyr Ile His Cys Arg Glu Val Ser Leu Val Thr Gln Arg Ser Leu
                260                 265                 270

Gly Asp Leu Ile Met Ser Cys Cys Pro Asp Pro Asn Pro Ile His
            275                 280                 285

Lys Ile Val Arg Lys Pro Ser Arg Ile Leu Phe Leu Met Asp Gly Phe
290                 295                 300

Asp Glu Leu Gln Gly Ala Phe Asp Glu His Ile Gly Pro Leu Cys Thr
305                 310                 315                 320

Asp Trp Gln Lys Ala Glu Arg Gly Asp Ile Leu Leu Ser Ser Leu Ile
                325                 330                 335

Arg Lys Lys Leu Leu Pro Glu Ala Ser Leu Leu Ile Thr Thr Arg Pro
            340                 345                 350

Val Ala Leu Glu Lys Leu Gln His Leu Leu Asp His Pro Arg His Val
            355                 360                 365

Glu Ile Leu Gly Phe Ser Glu Ala Lys Arg Lys Glu Tyr Phe Phe Lys
370                 375                 380

Tyr Phe Ser Asp Glu Ala Gln Ala Arg Ala Ala Phe Ser Leu Ile Gln
385                 390                 395                 400

Glu Asn Glu Val Leu Phe Thr Met Cys Phe Ile Pro Leu Val Cys Trp
                405                 410                 415

Ile Val Cys Thr Gly Leu Lys Gln Gln Met Glu Ser Gly Lys Ser Leu
            420                 425                 430

Ala Gln Thr Ser Lys Thr Thr Ala Val Tyr Val Phe Phe Leu Ser
            435                 440                 445

Ser Leu Leu Gln Pro Arg Gly Gly Ser Gln Glu His Gly Leu Cys Ala
450                 455                 460

His Leu Trp Gly Leu Cys Ser Leu Ala Ala Asp Gly Ile Trp Asn Gln
465                 470                 475                 480

Lys Ile Leu Phe Glu Glu Ser Asp Leu Arg Asn His Gly Leu Gln Lys
                485                 490                 495

Ala Asp Val Ser Ala Phe Leu Arg Met Asn Leu Phe Gln Lys Glu Val
            500                 505                 510

Asp Cys Glu Lys Phe Tyr Ser Phe Ile His Met Thr Phe Gln Glu Phe
            515                 520                 525

Phe Ala Ala Met Tyr Tyr Leu Leu Glu Glu Lys Glu Gly Arg Thr
530                 535                 540

Asn Val Pro Gly Ser Arg Leu Lys Leu Pro Ser Arg Asp Val Thr Val
```

```
                545                 550                 555                 560
Leu Leu Glu Asn Tyr Gly Lys Phe Glu Lys Gly Tyr Leu Ile Phe Val
                    565                 570                 575
Val Arg Phe Leu Phe Gly Leu Val Asn Gln Glu Arg Thr Ser Tyr Leu
                580                 585                 590
Glu Lys Lys Leu Ser Cys Lys Ile Ser Gln Gln Ile Arg Leu Glu Leu
                595                 600                 605
Leu Lys Trp Ile Glu Val Lys Ala Lys Ala Lys Lys Leu Gln Ile Gln
                610                 615                 620
Pro Ser Gln Leu Glu Leu Phe Tyr Cys Leu Tyr Glu Met Gln Glu Glu
625                 630                 635                 640
Asp Phe Val Gln Arg Ala Met Asp Tyr Phe Pro Lys Ile Glu Ile Asn
                    645                 650                 655
Leu Ser Thr Arg Met Asp His Met Val Ser Ser Phe Cys Ile Glu Asn
                660                 665                 670
Cys His Arg Val Glu Ser Leu Ser Leu Gly Phe Leu His Asn Met Pro
            675                 680                 685
Lys Glu Glu Glu Glu Glu Lys Glu Gly Arg His Leu Asp Met Val
            690                 695                 700
Gln Cys Val Leu Pro Ser Ser His Ala Ala Cys Ser His Gly Leu
705                 710                 715                 720
Val Asn Ser His Leu Thr Ser Ser Phe Cys Arg Gly Leu Phe Ser Val
                    725                 730                 735
Leu Ser Thr Ser Gln Ser Leu Thr Glu Leu Asp Leu Ser Asp Asn Ser
                740                 745                 750
Leu Gly Asp Pro Gly Met Arg Val Leu Cys Glu Thr Leu Gln His Pro
                755                 760                 765
Gly Cys Asn Ile Arg Arg Leu Trp Leu Gly Arg Cys Gly Leu Ser His
            770                 775                 780
Glu Cys Cys Phe Asp Ile Ser Leu Val Leu Ser Ser Asn Gln Lys Leu
785                 790                 795                 800
Val Glu Leu Asp Leu Ser Asp Asn Ala Leu Gly Asp Phe Gly Ile Arg
                    805                 810                 815
Leu Leu Cys Val Gly Leu Lys His Leu Leu Cys Asn Leu Lys Lys Leu
                820                 825                 830
Trp Leu Val Ser Cys Cys Leu Thr Ser Ala Cys Gln Asp Leu Ala
                835                 840                 845
Ser Val Leu Ser Thr Ser His Ser Leu Thr Arg Leu Tyr Val Gly Glu
            850                 855                 860
Asn Ala Leu Gly Asp Ser Gly Val Ala Ile Leu Cys Glu Lys Ala Lys
865                 870                 875                 880
Asn Pro Gln Cys Asn Leu Gln Lys Leu Gly Leu Val Asn Ser Gly Leu
                    885                 890                 895
Thr Ser Val Cys Cys Ser Ala Leu Ser Ser Val Leu Ser Thr Asn Gln
                900                 905                 910
Asn Leu Thr His Leu Tyr Leu Arg Gly Asn Thr Leu Gly Asp Lys Gly
                915                 920                 925
Ile Lys Leu Leu Cys Glu Gly Leu Leu His Pro Asp Cys Lys Leu Gln
            930                 935                 940
Val Leu Glu Leu Asp Asn Cys Asn Leu Thr Ser His Cys Cys Trp Asp
945                 950                 955                 960
Leu Ser Thr Leu Leu Thr Ser Ser Gln Ser Leu Arg Lys Leu Ser Leu
                    965                 970                 975
```

```
Gly Asn Asn Asp Leu Gly Asp Leu Gly Val Met Met Phe Cys Glu Val
            980                 985                 990

Leu Lys Gln Gln Ser Cys Leu Leu  Gln Asn Leu Gly Leu  Ser Glu Met
        995                 1000                 1005

Tyr Phe Asn Tyr Glu Thr Lys  Ser Ala Leu Glu Thr  Leu Gln Glu
        1010                1015                1020

Glu Lys  Pro Glu Leu Thr Val  Val Phe Glu Pro Ser  Trp
        1025                1030                1035

<210> SEQ ID NO 3
<211> LENGTH: 122
<212> TYPE: DNA
<213> ORGANISM: Homo sapiens

<400> SEQUENCE: 3
gtcggggaag gttttgagaa agaagggtcc ctggacaaga accttgtcat tttctgagtg    60
gccggtaccg aaaagagagg agggaagaac acactgactt tgactttcat acgaagcgga   120
ag                                                                 122

<210> SEQ ID NO 4
<211> LENGTH: 122
<212> TYPE: DNA
<213> ORGANISM: Homo sapiens

<400> SEQUENCE: 4
ctcctttgac ttcaactcct tatcacttct caaacaggtt acagtatcgg ggcattagtt    60
gccctgtttt taaaagaacg actacccagt tctaccgtag cacttcacca acaagtggca   120
tt                                                                 122

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccttggagat cagacctgtt gatagctgaa aactgtttgc tttc                     44

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaaagcaaac agttttcagc tatcaacagg tctgatctcc aagg                     44

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccttggagat cagacctgtt ggcagctgaa aactgtttgc tttc                     44
```

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaaagcaaac agttttcagc tgccaacagg tctgatctcc aagg            44

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccttggagat cagacctggc ggcagctgaa aactgtttgc tttc            44

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaaagcaaac agttttcagc tgccgccagg tctgatctcc aagg            44

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccttggagat cagacgcggc ggcagctgaa aactgtttgc tttc            44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaaagcaaac agttttcagc tgccgccgcg tctgatctcc aagg            44

<210> SEQ ID NO 13
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccggcaacaa gatgaagagc accaactcga gttggtgctc ttcatcttgt tgttttt      57

<210> SEQ ID NO 14
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ccggctacaa ctcaatgcaa tctttctcga gaaagattgc attgagttgt agttttt        57

<210> SEQ ID NO 15
<211> LENGTH: 1026
<212> TYPE: DNA
<213> ORGANISM: Orthopoxvirus vaccinia

<400> SEQUENCE: 15
atggatatct tcagggaaat cgcatcttct atgaaaggag agaatgtatt catttctcca      60
ccgtcaatct cgtcagtatt gacaatactg tattatggag ctaatggatc cactgctgaa     120
cagctatcaa aatatgtaga aaaggaggcg acaagaata aggatgatat ctcattcaag      180
tccatgaata agtatatgg gcgatattct gcagtgttta agattccctt tttgagaaaa      240
attggagata atttccaaac tgttgacttc actgattgtc gcactgtaga tgcgatcaac     300
aagtgtgttg atatcttcac tgaggggaaa attaatccac tattggatga accattgtct     360
ccagatacct gtctcctagc aattagtgcc gtatacttta aagcaaaatg gttgatgcca     420
tttgaaaagg aatttaccag tgattatccc ttttacgtat ctccaacgga atggtagat      480 gtaagtatga tgtctatgta cggcgaggca tttaatcacg catctgtaaa agaatcattc     540
ggcaactttt caatcataga actgccatat gttggagata ctagtatggt ggtaattctt     600
ccagacaata ttgatggact agaatccata gaacaaaatc taacagatac aaattttaag     660
aaatggtgtg actctatgga tgctatgttt atcgatgtgc acattcccaa gtttaaggta     720
acaggctcgt ataatctggt ggatgcgcta gtaaagttgg gactgacaga ggtgttcggt     780
tcaactggag attatagcaa tatgtgtaat tcagatgtga gtgtcgacgc tatgatccac     840
aaaacgtata tagatgtcaa tgaagagtat acagaagcag ctgcagcaac ttgtgcgctg     900
gtggcagact gtgcatcaac agttacaaat gagttctgtg cagatcatcc gttcatctat     960
gtgattaggc atgtcgatgg caaaattctt ttcgttggta gatattgctc tccaacaact    1020
aattaa                                                                1026

<210> SEQ ID NO 16
<211> LENGTH: 777
<212> TYPE: PRT
<213> ORGANISM: Homo sapiens

<400> SEQUENCE: 16

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

```
Ala Val Ser Leu Ser Met Gly Leu Tyr Met Gly Glu Thr Glu Thr Lys
                85                  90                  95

Val Met Gly Asn Asp Leu Gly Phe Pro Gln Gly Gln Ile Ser Leu
            100                 105                 110

Ser Ser Gly Glu Thr Asp Leu Lys Leu Leu Glu Ser Ile Ala Asn
        115                 120                 125

Leu Asn Arg Ser Thr Ser Val Pro Glu Asn Pro Lys Ser Ser Ala Ser
130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
    290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
        355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495
```

```
Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
    530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
                580                 585                 590

Met Thr Leu Leu Gln Tyr Ser Trp Met Phe Leu Met Ala Phe Ala Leu
                595                 600                 605

Gly Trp Arg Ser Tyr Arg Gln Ser Ser Ala Asn Leu Leu Cys Phe Ala
            610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
    770                 775

<210> SEQ ID NO 17
<211> LENGTH: 777
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80
```

```
Ala Val Ser Leu Ser Met Gly Leu Tyr Met Gly Glu Thr Glu Thr Lys
                85                  90                  95

Val Met Gly Asn Asp Leu Gly Phe Pro Gln Gly Gln Ile Ser Leu
            100                 105                 110

Ser Ser Gly Glu Thr Asp Leu Lys Leu Leu Glu Glu Ser Ile Ala Asn
            115                 120                 125

Leu Asn Arg Ser Thr Ser Val Pro Glu Asn Pro Lys Ser Ser Ala Ser
130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
            195                 200                 205

Asn Glu Ser Pro Trp Arg Ser Asp Ala Ala Ala Glu Asn Cys Leu
210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Pro Ser Asn Val Thr
            260                 265                 270

Leu Pro Gln Val Lys Thr Glu Lys Glu Asp Phe Ile Glu Leu Cys Thr
            275                 280                 285

Pro Gly Val Ala Ala Ala Lys Leu Gly Thr Val Tyr Cys Gln Ala
            290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
            355                 360                 365

Gly Ser Gly Asp Asp Asn Leu Thr Ser Leu Gly Thr Leu Asn Phe Pro
    370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
            435                 440                 445

Val Glu Gly Gln His Asn Tyr Leu Cys Ala Gly Arg Asn Asp Cys Ile
450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495
```

```
Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
                580                 585                 590

Met Thr Leu Leu Gln Tyr Ser Trp Met Phe Leu Met Ala Phe Ala Leu
                595                 600                 605

Gly Trp Arg Ser Tyr Arg Gln Ser Ser Ala Asn Leu Leu Cys Phe Ala
            610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
            675                 680                 685

Ile Arg Met Thr Tyr Ile Lys Glu Leu Gly Lys Ala Ile Val Lys Arg
            690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
            755                 760                 765

Ile Lys Lys Leu Leu Phe His Gln Lys
            770                 775

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CHO

<400> SEQUENCE: 18

Tyr Val Ala Asp
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
    peptide
<220> FEATURE:
<223> OTHER INFORMATION: N-term Ac
<220> FEATURE:
<223> OTHER INFORMATION: C-term chloromethylketone

<400> SEQUENCE: 19

Tyr Val Ala Asp
1

<210> SEQ ID NO 20
<211> LENGTH: 4
<212> TYPE: PRT
<213> ORGANISM: Homo sapiens

<400> SEQUENCE: 20

Leu Leu Ile Asp
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term pNA

<400> SEQUENCE: 21

Tyr Val Ala Asp
1

<210> SEQ ID NO 22
<211> LENGTH: 4
<212> TYPE: PRT
<213> ORGANISM: Homo sapiens

<400> SEQUENCE: 22

Ile Lys Gln Glu
1

<210> SEQ ID NO 23
<211> LENGTH: 20
<212> TYPE: PRT
<213> ORGANISM: Homo sapiens

<400> SEQUENCE: 23

Asn Glu Ser Pro Trp Arg Ser Asp Leu Leu Ile Asp Glu Asn Cys Leu
1               5                   10                  15
Leu Ser Pro Leu
            20

<210> SEQ ID NO 24
<211> LENGTH: 20
<212> TYPE: PRT
<213> ORGANISM: Homo sapiens

<400> SEQUENCE: 24

Ile Glu Leu Cys Thr Pro Gly Val Ile Lys Gln Glu Lys Leu Gly Thr
1               5                   10                  15
Val Tyr Cys Gln
            20

<210> SEQ ID NO 25
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Ala Ala
1

<210> SEQ ID NO 26
<211> LENGTH: 19
<212> TYPE: DNA
<213> ORGANISM: Homo sapiens

<400> SEQUENCE: 26
tctgagtggc cggtaccga                                                19

<210> SEQ ID NO 27
<211> LENGTH: 19
<212> TYPE: DNA
<213> ORGANISM: Homo sapiens

<400> SEQUENCE: 27
cattagttgc cctgttttt                                                19
```